(12) United States Patent
Lau et al.

(10) Patent No.: US 8,772,571 B2
(45) Date of Patent: Jul. 8, 2014

(54) COMPOSITIONS AND METHODS FOR OSTEOGENIC GENE THERAPY

(75) Inventors: Kin-Hing William Lau, Redlands, CA (US); David J. Baylink, Loma Linda, CA (US); Susan L. Hall, San Bernardino, CA (US); Shin-Tai Chen, Colton, CA (US); Subburaman Mohan, Redlands, CA (US)

(73) Assignees: The United States of America as represented by the Department of Veterans Affairs, Washington, DC (US); Loma Linda University, Loma Linda, CA (US)

( * ) Notice: Subject to any disclaimer, the term of this patent is extended or adjusted under 35 U.S.C. 154(b) by 540 days.

(21) Appl. No.: 12/879,842

(22) Filed: Sep. 10, 2010

(65) Prior Publication Data

US 2011/0004947 A1 Jan. 6, 2011

Related U.S. Application Data

(62) Division of application No. 11/452,873, filed on Jun. 13, 2006, now Pat. No. 7,816,140.

(60) Provisional application No. 60/690,696, filed on Jun. 14, 2005.

(51) Int. Cl.
| | |
|---|---|
| A01K 67/00 | (2006.01) |
| A61K 48/00 | (2006.01) |
| C12N 5/00 | (2006.01) |
| C12N 15/63 | (2006.01) |

(52) U.S. Cl.
USPC ............... 800/8; 514/44; 435/455; 435/372; 435/383; 424/93.7

(58) Field of Classification Search
CPC ............ A01K 2207/12; A01K 2267/035; A01K 38/1825; C12N 2799/027
USPC ............... 800/8; 514/44; 435/455, 372, 383; 424/93.21
See application file for complete search history.

(56) References Cited

U.S. PATENT DOCUMENTS

2004/0223953 A1  11/2004  Kung et al.

FOREIGN PATENT DOCUMENTS

| WO | WO 89/00198 | 1/1989 |
|---|---|---|
| WO | WO 2006/116678 | 11/2006 |

OTHER PUBLICATIONS

Hall et al., J Gene Med. Oct. 2009;11(10):877-88. Stem cell antigen-1+ cell-based bone morphogenetic protein-4 gene transfer strategy in mice failed to promote endosteal bone formation.*

Derner, et al. (2005) Clin. Podiatr. Med. Surg., 22:607-18 The Bone Mophogenic Protein.*
Gafni et al .,Gene therapy platform for bone regeneration using an exogenously regulated, AAV-2-based gene expression system Mol Ther. Apr. 2004;9(4):587-95.*
Moutsatsos IK et al., Exogenously regulated stem cell-mediated gene therapy for bone regeneration Mol Ther. Apr. 2001;3(4):449-61-Abstract.*
Wikipedia Bone morphogenetic protein From Wikipedia, the free encyclopedia Last visited Jul. 24, 2013.*
Chen et al., "Osteoblast precursor cells are found in CD34$^+$ cells from human bone marrow," Stem Cells, 15(5):368-377, 1997.
D'Ippolito et al., "Marrow-isolated adult multilineage inducible (MIAMI) cells, a unique population of postnatal young and old human cells with extensive expansion and differentiation potential," J. Cell Science, 117:2971-2981, 2004.
Gysin et al., "Ex vivo gene therapy with stromal cells transduced with a retroviral vector containing the BMP4 gene completely heals critical size calvarial defect in rats," Gene Ther., 9(15):991-999, 2002.
Hall et al., "Sca-1$^+$ Hematopoietic Cell-based Gene Therapy with a Modified FGF-2 Increased Endosteal/Trabecular Bone Formation in Mice," Molecular Therapy, 15(10):1881-1889, 2007.
Ishii et al., "Appropriate control of ex vivo gene therapy delivering basic fibroblast growth factor promotes successful and safe development of collateral vessels in rabbit model of hind limb ischemia," J. Vasc. Surg., 39(3):629-638, 2004.
Kawaguchi et al., "Acceleration of fracture healing in nonhuman primates by fibroblast growth factor-2," J. Clin. Endocrinol. Metab., 86(2):875-880, 2001.
Klamut et al., "Progress toward skeletal gene therapy," Crit. Rev. Eukaryot. Gene Expr., 14(1-2):89-136, 2004.
Kucia et al., "Bone marrow as a home of heterogenous populations of nonhematopoietic stem cells," Leukemia, 19:1118-1127, 2005.
Kucia et al., "Bone marrow as a source of circulating CXCR4$^+$ tissue-committed stem cells," Biol. Cell, 97:133-146, 2005.
Martin et al., "Fibroblast growth factor-2 supports ex vivo expansion and maintenance of osteogenic precursors from human bone marrow," Endocrinology, 138(10):4456-4462, 1997.

(Continued)

Primary Examiner — Maria Leavitt
(74) Attorney, Agent, or Firm — Klarquist Sparkman, LLP

(57) ABSTRACT

The present disclosure provides compositions and methods for increasing bone growth and/or enhancing wound healing, for example, fracture repair. The disclosure provides recombinant nucleic acids useful for promoting bone growth. For example, the disclosure provides recombinant nucleic acids that encode a fibroblast growth factor-2 (FGF-2) analog. The disclosure also provides vectors and cells incorporating these nucleic acids, as well as FGF-2 analogs encode by them. The disclosure also provides a mouse system of bone marrow transplantation and methods for producing as well as methods for using the system. Methods for inducing division and/or inducing differentiation of a hematopoietic stem cell are also provided, as are methods for enhancing bone growth and/or wound repair (for example, fracture repair).

9 Claims, 10 Drawing Sheets

(56) References Cited

OTHER PUBLICATIONS

Mayahara et al., "In Vivo Stimulation of Endosteal bone Formation by Basic Fibroblast Growth Factor in Rats," *Growth Factors*, 9:73-80, 1993.

Oakes and Lieberman, "Osteoinductive applications of regional gene therapy: ex vivo gene transfer," *Clin. Orthop. Relat. Res.*, 379S:S101-S112, 2000.

Olmsted-Davis et al., "Primitive adult hematopoietic stem cells can function as osteoblast precursors," *Proc. Natl. Acad. Sci. USA*, 100(26):15877-15882, 2003.

Persons et al., "Retroviral-Mediated Transfer of the Green Fluorescent Protein Gene Into Murine Hematopoietic Cells Facilities Scoring and Selection of Transduced Progenitors In Vitro and Identification of Genetically Modified Cells In Vivo," *Blood*, 90(5):1777-1786, 1997.

Pierelli et al., "Erythropoietin Addition to Granulocyte Colony-Stimulating Factor Abrogates Life-Threatening Neutropenia and Increases Peripheral-Blood Progenitor-Cell Mobilization After Epirubicin, Paclitaxel, and Cisplatin Combination Chemotherapy: Results of a Randomized Comparison," *Journal of Clinical Oncology*, 17(4):1288-1295, 1999.

Sasada et al., "Expression of Modified bFGF cDNAs in Mammalian Cells," *Ann. NY Science Acadamy*, pp. 149-160 and Abstract, 1991.

Seno et al., "Stabilizing Basic Fibroblast Growth Factor Using Protein Engineering," *Biochem. Biophys. Res. Comm.*, 151(2):701-708, 1988.

Stryer, *Biochemistry*, 3$^{rd}$ Edition:18-19, 1975.

Trevisan et al., "Cycle Initiation and Colony Formation in Culture by Murine Marrow Cells With Long-Term Reconstituting Potential In Vivo," *Blood*, 88(11):4149-4158, 1996.

Tuli et al., "Characterization of Multipotential Mesenchymal Progenitor Cells Derived from Human Trabecular Bone," *Stem Cells*, 21:681-693, 2003.

Watson et al., *Recombinant DNA*, 2$^{nd}$ Edition:153-155, 2001.

\* cited by examiner

☐ 284 amino acids of BMP2/4 secretion signaling peptide

▓ 8 amino acids propeptide of FGF-2 gene

▨ 146 amino acids mature peptide of FGF-2 gene

BMP2/4 secretion signal junction
↓
---LVTFG*HDGRGHALTRRRRAKR*SPK-----

BMP2/4FGF secretion signal junction
↓
---LVTFG*HDGRGHALTRRRRAKR*AAGSITTLPALPE-----

FIG. 2A
FIG. 2B.
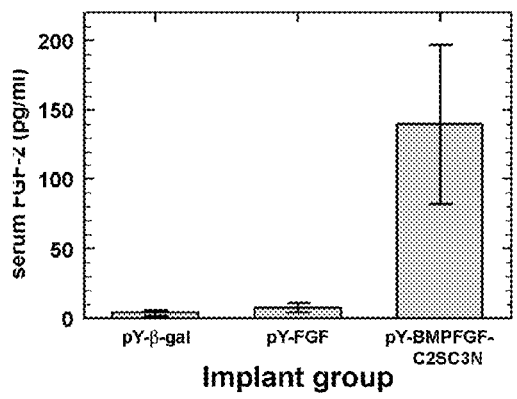
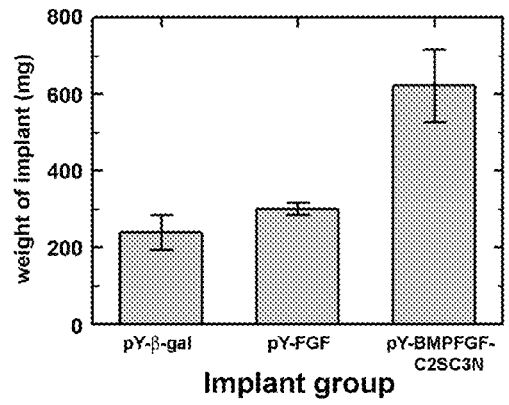

FIG. 4A      FIG. 4B
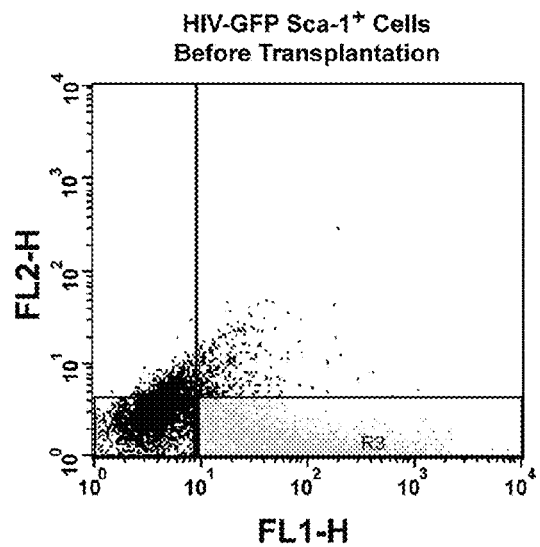
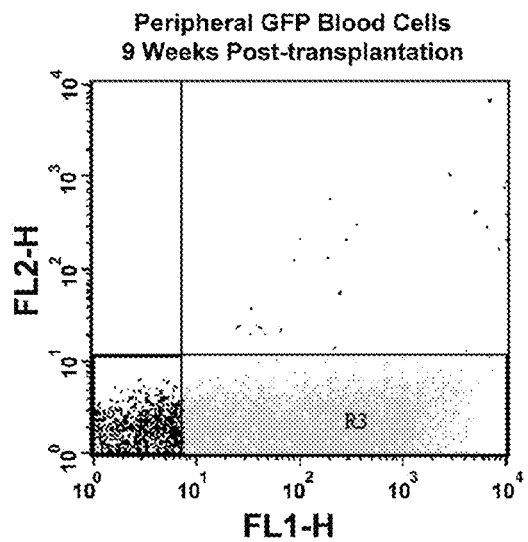
FIG. 4C
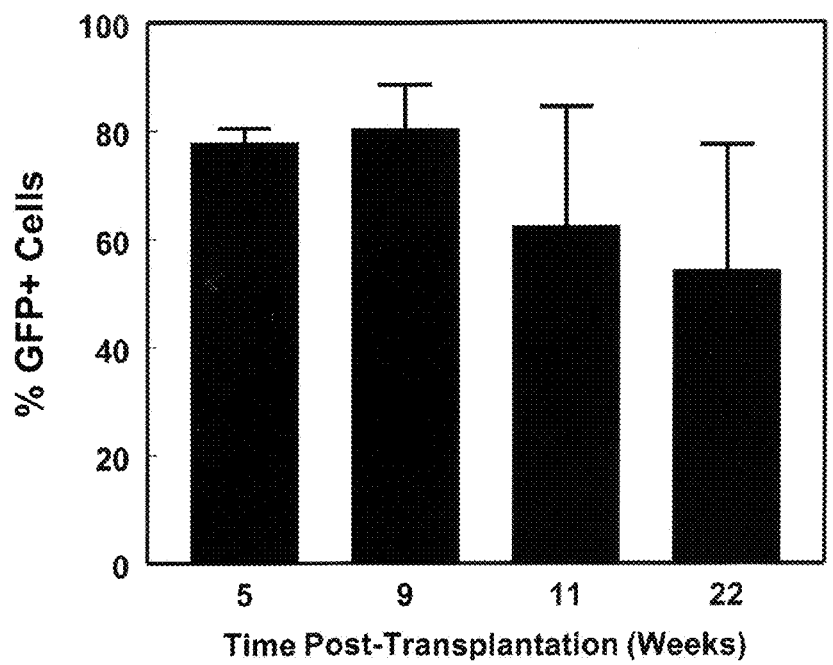

COMPOSITIONS AND METHODS FOR OSTEOGENIC GENE THERAPY

CROSS REFERENCE TO RELATED APPLICATION

This is a divisional of U.S. patent application Ser. No. 11/452,873, filed Jun. 13, 2006, now U.S. Pat. No. 7,816,140, issued Oct. 19, 2010, which claims benefit of priority to U.S. Patent Application No. 60/690,696, filed Jun. 14, 2005. The entire disclosures of each of these applications are hereby expressly incorporated by reference in their entirety.

ACKNOWLEDGMENT OF GOVERNMENT SUPPORT

This invention was made while one or more of the inventors were employed by the United States government (Department of Veterans Affairs) and with United States government support: Assistance Award DAMD 17-03-2-0021 from the United Sates Army Medical Research Acquisition Activity and National Research Service Award NIAMSD Grant No. AR07543-14. The United States government has certain rights in the invention.

FIELD

The present disclosure relates to the field of osteogenic therapy. In particular, the disclosure relates to methods of treating skeletal disorders, such as osteoporosis and skeletal fractures with osteogenic growth factors, such as Fibroblast Growth Factor-2 and analogs thereof.

BACKGROUND

Growth factors, including members of the FGF and Wnt families, are pleiotropic regulators of proliferation, differentiation, migration, and survival in a variety of cell types. For example, basic fibroblast growth factor (bFGF or FGF-2) has been used to influence cellular growth, differentiation and migration (Bikfalvi et al., *Endocrine Rev.* 18:26-45, 1997; Friesel et al., *FASEB J.* 9:919-925, 1995; Moyamoto et al., *J. Cell. Physiol.* 177:58-67, 1998; D'Amore et al., *Growth Factors* 8:61-75, 1993) and is also a potent stimulator of angiogenesis (Moyamoto et al., *J. Cell. Physiol.* 177:58-67, 1998; D'Amore et al., *Growth Factors* 8:61-75, 1993) and hematopoiesis in vivo (Allouche et al., *Prog. Growth Factor* 6:35-48, 1995). FGF-2 is involved in organogenesis (Martin, *Genes Dev.* 12:1571-1586, 1998), vascularization (D'Amore et al., *Growth Factors* 8:61-75, 1993), and wound healing (Ortega et al., *Proc. Natl. Acad. Sci. USA,* 95:5672-5677, 1998), and plays an important role in the differentiation and/or function of various organs, including the nervous system (Ortega et al., *Proc. Natl. Acad. Sci. USA,* 95:5672-5677, 1998), the skeleton (Montero et al., *J. Clin. Invest.* 105:1085-1093, 2000), and several other organs (Bikfalvi et al., *Endocrine Rev.* 18:26-45, 1997). Because of its angiogenic and anabolic properties, FGF-2 has received considerable attention for potential clinical applications, including wound healing and tissue repair.

The therapeutic utility of the FGF-2 protein therapy has been assessed in various animal models with promising results. Accordingly, administration of recombinant human FGF-2 protein improved the healing of ischemic wounds in rats (Quirinia et al., *J. Plast. Reconstr. Surg. Hand Surg.* 32:9-18, 1998), promoted scar-less healing of skin incisional wounds in normal rats (Akasaka et al., *J. Pathol.,* 203:710- 720, 2004; Spyrou et al., *Br. J. Plast. Surg.* 55:275-282, 2002), enhanced wound healing in healing-impaired diabetic rats (Takeuchi et al., *J. Pharmacol. Exp. Ther.* 281:200-207, 1997), and accelerated the wound healing of chick embryo chorioallantoic membrane (Ribatti et al., *Angiogenesis* 3:89-95, 1999). Administration of human recombinant FGF-2 protein also promoted fracture healing in the monkey (Kawaguchi et al., *J. Clin. Endorinol. Metab.* 86:875-880, 2001), improved cartilage repair in the rabbit (Tanaka et al., *Tissue Engineering* 10:633-641, 2004), stimulated early stages of tendon healing in the rat (Chan et al., *Acta Orthop. Scand.* 71:513-518, 2000), and led to formation of new trabeculae that physically connect with pre-existing trabeculae in osteopenic rats (Lane et al., *J. Bone Miner Res.* 18:2105-2115, 2003; Lane et al., *Osteoporos Int.* 14:374-382, 2003). Subcutaneous implantation of controlled-release FGF-2 protein into the back of mice resulted in de novo formation of adipose tissue (Tabata et al., *Tissue Engineering* 6:279-289, 2000).

Nonetheless, attempts to use FGF-2 in gene transfer approaches have led to inconsistent results. While ex vivo FGF-2 promoted collateral vessel development in a rabbit hind limb ischemia model (Ishii et al., *J. Vasc. Surg.* 39:629-638, 2004) and improved blood flow and cardiac function in a swine myocardial ischemia model (Ninomiya et al., *Gene Ther.* 10:1152-1160, 2003), in vivo expression of FGF-2 from a plasmid vector did not significantly improve survival of rat ischemic myocutaneous flaps (Hijjawi et al., *Arch. Surg.* 139: 142-147, 2004). Similarly, the in vivo FGF-2 expression failed to preserve functional responses to photoreceptor in a rat retinal degeneration model (Spencer et al., *Mol. Ther.* 3:746-756, 2001).

Thus, there exists a need for compositions and methods for increasing the efficacy of treatment using osteogenic growth factors, such as FGF-2, to enhance bone growth and repair for the treatment of a wide variety of skeletal disorders. The compositions and methods disclosed herein address this need, providing numerous benefits, which will become apparent upon review of the specification.

SUMMARY

The present disclosure relates to compositions and methods for increasing bone growth and/or enhancing wound healing, for example, fracture repair. Thus, a first aspect of the disclosure relates to methods of inducing division and/or inducing differentiation of a hematopoietic stem cell. These methods involve expressing a heterologous nucleic acid that encodes an osteogenic growth factor in a stem cell, such as a hematopoietic stem cell. The growth factor is selected to i) promote self-renewal by the stem cell and ii) enhance bone growth in vivo. Optionally, the growth factor increases angiogenesis in vivo. Examples of osteogenic growth factors include members of the fibroblast growth factor (FGF) family (for example, those FGF homologues that act via FGF-receptors 1, 2 and/or 3, such as FF-1, FGF-2 and FGF-4), members of the Wnt family, growth hormone, members of the angiopoietin family and analogs thereof. Cells can be expanded in vitro, ex vivo or in vivo, for example, to enhance bone growth and/or wound repair.

In a particular example, hematopoietic stem cells or hematopoietic progenitor cells are used as vehicles for delivering and expressing therapeutic proteins that are osteogenic growth factors (such as FGF-2 or therapeutic analogs thereof) to bone tissue. In certain embodiments, applicable to humans, the donor cells are CD34$^+$ cells, which can be isolated from bone marrow, cord blood or peripheral blood. The selected hematopoietic stems cells express CXCR4 receptors and have the ability to home to, and to reside and engraft in the bone marrow space. These cells can be transduced with a therapeutic gene to target delivery of a therapeutic protein, such as a member of the FGF family, the Wnt family or growth hormone, that promotes systemic and/or local bone formation and fracture healing. In a particular example, the therapeutic agent is an FGF-2 analog that promotes both bone formation and angiogenesis to assist in bone healing. This delivery system can be used to treat many types of systemic or local bone defects, such as bony defects from injuries, fractures, or diseases like osteoporosis, osteomyelitis or cancer. Additional stem cells that express CXCR4 and that can target the bone marrow include endothelial stem cells and subsets of mesenchymal stem cells.

In disclosed embodiments, the therapeutic protein is expressed from a nucleic acid construct delivered into the hematopoietic stem cell or hematopoietic progenitor cell. The cells are then delivered to target sites, such as the endosteal bone surface of the bone marrow cavity, where they engraft and continue to produce progeny cells. Any suitable vector is used to deliver the nucleic acid construct into the cell. Promoters are chosen to drive the expression of the therapeutic protein, such as promoters that selectively drive expression in target tissue where expression is desired. For example, tissue-specific promoters are used that operate only in the presence of differentiated or undifferentiated osteoblasts. Inducible or suppressible promoters are also used to regulate expression of the therapeutic protein in the target bone tissue.

The hematopoietic stem cells or progenitor cells that act as delivery cell vehicles can be isolated either from the bone marrow, peripheral blood, or umbilical cord blood of a subject or a donor (such as the subject into whom the transduced cells will be transplanted), or they can be derived from embryonic stem cells. In disclosed examples they are exposed to a nucleic acid construct carrying the nucleic acid sequence for expressing the therapeutic protein which is constructed in a manner that it can enter the hematopoietic stem cells or progenitor cells (for example using a viral vector or a nuclear localization sequence). In particular examples, the subject is pretreated in a manner that enhances homing of the delivery cells to the bone marrow. For instance, the subject can be pre-treated with erythropoietin to induce the formation of red marrow throughout the skeleton, which leads to increased homing of the delivery cells to the skeleton. The transduced delivery cells can be injected intravenously into the subject, and the cells then home to the bone marrow and engraft there where they produce progeny cells that in turn express the therapeutic protein. In particular examples, the therapeutic protein is expressed in the endosteal bone niche of the bone marrow site to induce bone formation by stimulating and recruiting nearby stromal cells in the marrow space to mature into osteoblasts, resulting in increased targeted bone formation.

Targeted delivery of the therapeutic protein, and/or therapeutic induction of bone formation, can be more specifically directed by selecting a suitable promoter. For example when a promoter specific for erythroblasts is used, expression of the therapeutic protein is concentrated in red marrow areas. Expression of the therapeutic protein can be restricted to areas enriched with osteoblasts and/or its precursors by selecting a tissue specific promoter, such as an erythroid promoter or an osteoblast promoter. Regulatable promoters (such as a tetracycline regulatable system, e.g., Tet/on or Tet/off) can be used to permit therapy to be regulated by initiating or discontinuing administration of tetracycline (or an analog thereof).

Another aspect of the disclosure relates to recombinant nucleic acids useful for promoting bone growth. For example, the disclosure provides recombinant nucleic acids that encode a fibroblast growth factor-2 (FGF-2) analog. The disclosure also provides vectors and cells incorporating these nucleic acids, as well as FGF-2 analogs encoded by them.

Another aspect of the disclosure relates to methods of producing a mouse system of bone marrow transplantation involving transplanting hematopoietic stem cells or progenitor cells into sublethally irradiated, myelosuppressed recipients. In one embodiment the donor cells are Sca-1$^+$ cells isolated from bone marrow, cord blood or peripheral blood. Methods for identifying agents that modulate bone growth using the mouse bone marrow model are also disclosed.

The foregoing and other features and advantages will become more apparent from the following detailed description of several embodiments, which proceeds with reference to the accompanying figures.

BRIEF DESCRIPTION OF THE DRAWINGS

FIG. 1A shows an exemplary chimeric (recombinant) human FGF-2 analog. The FGF-2 analog was constructed by adding the BVP2/3 secretion signal sequence to the 5' end of the FGF gene. The positions of the four cysteines within the FGF-2 protein are indicated by inverted triangles.

FIGS. 2A and B are bar graphs demonstrating the effects of ex vivo administration of pY-BMPFGFC2SC3N-transduced rat skin fibroblasts on the serum FGF-2 level (A) and the growth of implants (B) in a dorsal back implant rat model. Gel-foam squares impregnated overnight with 4 million primary rat skin fibroblasts transduced with pY-β-gal, pY-FGF or pY-BMPFGFC2SC3N vectors were implanted subcutaneously into the dorsal back of syngeneic rats. Serum FGF-2 levels and size were evaluated 14 days after implantation.

FIG. 3A illustrates a comparison of engraftment efficiency by the tail vein injection route and the retro-orbital injection route of transplantation. The engraftment efficiency was assessed by measuring the mean percent eGFP-positive cells in host mice peripheral blood over time. Mice were transplanted with 400,000 Sca-1$^+$ cells from eGFP-transgenic donor mice through either the tail vein injection route or the retro-orbital injection route. At indicated time points, peripheral blood was collected and assayed for percent eGFP cells by flow cytometry. FIG. 3B illustrates a comparison of the engraftment efficiency irr wild type C57BL/6J or $W^{41}/W^{41}$ recipient mice with or without sublethal irradiation. Engraftment was determined by measuring mean percent eGFP-positive cells in peripheral blood over time. Five hundred thousand Sca-$1^+$ cells from eGFP-transgenic donor mice were transplanted into non-irradiated wild type (non-irr wild), non-irradiated $W^{41}/W^{41}$ (non-irr W41/W41), irradiated wild type (irr wild) or irradiated $W^{41}/W^{41}$ (irr W41/W41) recipient mice At indicated time points, peripheral blood was collected and assayed for percent GFP cells by flow cytometry. FIG. 3C illustrates a comparison of the mean percent eGFP-positive cells in peripheral blood of recipient mice preconditioned by sublethal irradiation either 4 hours or 24 hours prior to transplantation with Sca-$1^+$ cells from TgN-eGFP donors. Six $W^{41}/W^{41}$ recipient mice were subjected to a single 500 cGy-dose of irradiation. Twenty hours later, another group of 6 $W^{41}/W^{41}$ recipient mice received an identical dose of radiation. Four hours later, both groups were injected with $2\times10^6$ Sca-$1^+$-enriched cells via retroorbital injection. At 12, 24, 36 and 52 weeks post-transplantation, peripheral blood was collected and assayed for percent GFP cells by flow cytometry (as an index of engraftment). All 12 mice were successfully engrafted.

FIGS. 4A and B are flow cytometry scatter plots. Percentage of GFP-expressing donor cells in C57BL/6J Sca-$1^+$ cells transduced with an HIV-based vector expressing the GFP marker gene five days post-transduction (left panel) and in peripheral blood of a representative recipient mouse nine weeks post transplantation (right panel). Percentage of GFP-expressing cells (GFP+ cells) was analyzed by FACS. FIG. 4C is a bar graph comparing the mean percent eGFP-positive cells peripheral blood of host mice transplanted with Sca-$1^+$ cells transduced with an HIV-based viral vector expressing the eGFP marker gene at 5, 9, 11, and 22 weeks post transplantation.

FIG. 5A illustrates serum FGF-2 levels at week 8, 10, 12, and 14 post-transplantation were measured by ELISA according to Methods. Results are shown as mean±SEM (n=8 each). The FGF-2 group was the group of mice receiving transplantation with pY-BMPFGFC2SC3N-transduced Sca-1+ cells, whereas the GFP group was the group of recipient mice receiving transplantation with pY-GFP-transduced Sca-1+ cells. *p<0.05 compared to the GFP group.

FIG. 7A schematically illustrates a set of tet-on MLV-based vectors expressing either eGFP or the modified FGF-2 gene, with or without the tet regulatable promoter. The MLV.FGF2* is the pY-modified FGF-2 vector. The expression of the modified FGF2 is driven by the viral MLV-LTR promoter. The MLV.tet.eGFP and MLV.tet.FGF2* are doxycycline inducible retroviral vectors expressing the eGFP or modified FGF-2 gene, respectively. In these two vectors, the expression of eGFP or FGF2 gene was driven by the TetO promoter, which is inducible doxycycline (a tetracycline analog). The arrows indicate the direction of the transcription.

SEQUENCE LISTING

Figures 1A, 1B:
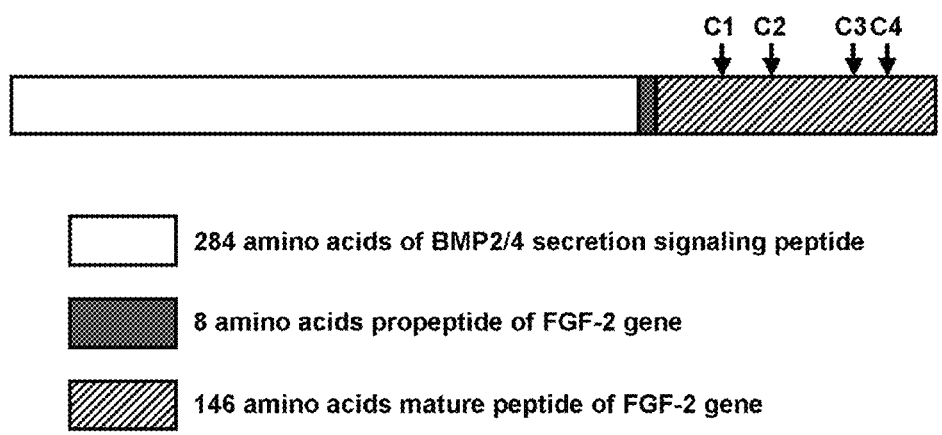
FIGS. 1A and B are a schematic illustrations of a chimeric FGF-2 protein including a BVP2/4 secretion signal sequence (FIG. 1A) and the amino acid sequence surrounding the mature peptide cleavage site within the chimeric protein (FIG. 1B).
FIG. 1B represents the amino acid sequence surrounding the mature peptide cleavage site of the BMP2/4 chimera (top; SEQ ID NO: 22) and that surrounding the mature peptide cleavage site of the BMP2/4-FGF-2 chimera (bottom; SEQ ID NO: 23). The last 5 amino acid residues of the C-terminus of the 284-residue BMP-2 secretion signal sequence are shown in bold letters in FIG. 1B. The last 16 residues of the C-terminal end of the BMP-4 secretion signal sequence that had been incorporated in the BMP2/4 hybrid sequence are shown as italic letters in FIG. 1B. The entire 8-residue propeptide of FGF-2 (minus the start codon for methionine) was underlined in FIG. 1B. The respective arrow denotes the cleavage site for mature BMP-4 and FGF-2 protein, respectively. In the design of the BMP2/4-FGF-2 chimeric gene, the start codon for methionine of the FGF-2 gene was deleted and replaced with the BMP2/4 secretion signal sequence.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, Annex C/St.25 text file, created on Sep. 10, 2010, 14,816 bytes, which is incorporated by reference herein. In the accompanying sequence listing:

SEQ ID NO:1 is the nucleotide sequence of human FGF-2.
SEQ ID NO:2 is the amino acid sequence of human FGF-2.
SEQ ID NO:3 is the nucleotide sequence of an exemplary human FGF-2 analog.
SEQ ID NO:4 is the amino acid sequence of an exemplary human FGF-2 analog including a signal peptide (amino acid positions 1-284), an eight amino acid propeptide (italicized) and cysteine to serine substitution at position 70 and a cysteine to arginine substitution at position 88 of the mature FGF-2 polypeptide.
SEQ ID NO:5 is the nucleotide sequence of the BMP2/4 signal sequence.
SEQ ID NO:6 is the amino acid sequence of the BMP2/4 signal sequence.
SEQ ID NOS:7-20 are the nucleotide sequence of oligonucleotide primers.
SEQ ID NO:21 is the nucleotide sequence of a Kozak initiation sequence.

DETAILED DESCRIPTION

Introduction

An important goal in the field of osteoporosis therapy is an osteogenic therapy which corrects the bone mineral deficit in patients with osteoporosis. One approach to developing osteogenic therapies has focused on gene therapy. However, such efforts have achieved only limited experimental success. To develop a successful therapy for treating and inhibiting the development of osteoporosis and other bone disorders, it is helpful to identify candidate genes that express proteins to promote bone growth within bone tissue, and suitable cells for expressing them.

Factors to be considered in selecting a candidate gene include: the ability to promote stem cell renewal; the ability to enhance bone growth. Additionally, the factors can promote angiogenesis. For example, bone morphogenetic proteins (BMPs) are able to promote enhanced bone growth in the short term, but cause stem cell differentiation that makes them unsuitable for systemic therapies aimed at promoting growth and maintenance of bone tissue over time. Rather, an osteogenic growth factor that both promotes stem cell renewal and enhances bone growth provides optimal therapeutic results, especially when systemic effects are desirable. This disclosure provides methods for delivering such osteogenic growth factors in vitro, ex vivo, and in vitro, to induce division and/or differentiation of stem cells, such as hematopoietic stem cells. In certain embodiments, the disclosed methods are used to promote localized and/or systemic bone formation, for example, to enhance bone strength and/or promote fracture repair.

Thus, one aspect of this disclosure concerns methods for inducing division and/or differentiation of stem cells, such as hematopoietic stem cells. The methods involve expressing a heterologous nucleic acid that includes a polynucleotide sequence that encodes an osteogenic growth factor in a stem cell (and/or progenitor cell). In one aspect, these methods are useful for inducing bone formation in vitro, ex vivo, and in vivo. The selected cells are stem cells that are capable of expressing the therapeutic nucleic acid (or transgene), as well as homing to and stably engrafting the bone marrow. Suitable donor cells for administration to a subject to promote increased bone growth are pluripotent stem cells, which are capable of self renewal, and differentiation along multiple lineage pathways. In specific examples, the stem cells are hematopoietic stem cells, such as embryonic stem cells or pluripotent hematopoietic stem cells. Various cells have been referred to as hematopoietic stem cells, including CD34 positive cells isolated from the umbilical cord blood, the bone marrow, and the peripheral blood. Any one of these tissues provides a source of stem cells for use in the compositions and methods described herein, and such stem cells can be isolated from these tissues using isolation procedures known in the art. One significant feature of these cells is that they are able to home to, engraft, continue to produce progeny cells (including additional stem cells), and reside in the bone marrow cavity. The cells can also be any fraction of marrow stem cells, osteoblast cells and embryonic stem cells, so long as they are able to home to, reside and engraft in the bone marrow cavity. For example, endothelial stem cells and mesenchymal stem cells that express CXCR4 can be substituted for hematopoietic stem cells in the methods disclosed herein.

A non-limiting example of such a stem cell is the Sca-1$^+$ stem cell population described below. For applications involving human subjects, it is useful to use a human hematopoietic stem cell, such as a human bone marrow derived stem cell. Such stem cells can be isolated from the bone marrow, from umbilical cord vein blood or from the peripheral blood, for example, following treatment with Granulocyte-macrophage colony-stimulating factor (GM-CSF) and or erythropoietin (EPO). For example, human bone marrow derived stem cells capable of homing to the bone marrow and giving rise to osteoblast lineage cells are characterized as CD34$^+$, lin$^-$ cells, more specifically CD34$^+$, AC133$^+$, lin$^-$, CD45$^-$, CXCR4$^+$ (Kucia et al., *Leukemia* 19:1118-1177, 2005). Additionally, hematopoietic stem cells characterized as CD34$^+$/CD38$^+$ cells (Chen et al., *Stem Cells* 15:368-377, 1997); CD73$^+$, STRO-1$^+$, CD105$^+$, CD34$^-$, CD45$^-$, CD144$^-$ cells (Tuli et al., *Stem Cells* 21:681-693); and CD29$^+$, CD63$^+$, CD81$^+$, CD122$^+$, CD164$^+$, cMet$^+$, bone morphogenetic protein receptor 1B$^+$, and neurotrophic tyrosine kinase receptor 3$^+$ and CD34$^-$, CD36$^-$, CD45$^-$, CD117$^-$ (cKit$^-$), and HLA-DR$^-$ (D'Ippolito et al., *Journal of Cell Science* 117:2971-2981, 2004) are also human pluripotent hematopoietic stem cells. Such cells are capable of expressing therapeutic nucleic acids at appropriate levels, home to bone marrow throughout the entire skeleton, undergo stem cell renewal under appropriate conditions (e.g., exposure to FGF), and give rise to cells of the osteoblastic lineage. In certain embodiments, the hematopoietic stem cells express CXCR4, which facilitates homing to the bone marrow. Additionally, the stem cells can express one or more FGF receptors.

The hematopoietic stem cell can be a component of a population of cells enriched in hematopoietic stem cells. For example, the population can be enriched by treating a population of cells with a growth factor that promotes expansion of hematopoietic lineage cells, such as erythropoietin (EPO), granulocyte colony stimulating factor (GCSF), and/or granulocyte macrophage colony stimulating factor (GMCSF). The population of cells can be treated either before or after isolation from bone marrow, cord blood or peripheral blood. Thus, the population of cells can be enriched for hematopoietic stem cells by administering EPO, GCSF and/or GMCSF to a donor subject prior to isolating the population of cells from bone marrow or peripheral blood. In some embodiments, the hematopoietic stem cells are obtained from the same subject to whom the cells are to be administered.

The osteogenic growth factor is selected to promote self-renewal by the stem cell and enhance bone formation in vivo. Optionally, the growth factor also increases angiogenesis in vivo. Exemplary osteogenic growth factors that promote stem cell self-renewal and that enhance bone formation include members of the FGF family of growth factors. For example, FGF family members that bind to and act via FGF-receptors 1, 2 and/or 3, such as FGF-1, FGF-2, FGF-4, and analogs thereof, are used. In other embodiments, members of the Wnt family of growth factors (such as Wnts 1, 2, 2B, 3, 3B, 4, 5A, 5B, 6, 7A, 7B, 8A, 8B, 9A, 10A, 10B, 11 and 16) are used to promote bone formation. In alternative embodiments, the osteogenic growth factor is selected from among growth hormone, angiopoietins 1-7 (e.g., Angpt12, Angpt13), glial cell nerve factor, stem cell factor, parathyroid hormone (PTH), insulin like growth factor (IGF), platelet derived growth factor (PDGF), vascular endothelial growth factor (VEGF), Cox-2, and TGF-β. Alternatively, nucleic acids that encode protein factors that regulate one of these genes, such as transcription factors, e.g., zinc finger binding proteins, can be introduced into hematopoietic stem cells or progenitor cells and delivered to the bone marrow to enhance bone growth and/or promote healing of bone tissue.

The nucleic acids encoding osteogenic growth factors can be introduced into the stem cells or progenitor cells as isolated linear nucleic acids or incorporated into a wide variety of vectors, including plasmids, artificial chromosomes and viral vectors. The nucleic acids can be introduced into the cells by a variety of means known in the art, including, for example, electroporation, lipid or liposome mediated transformation, biolistic (particle bombardment) transformation, and transfection with a viral vector. The viral vector can be an integrating viral vector, such as a lentiviral vector, retroviral vector or an adeno-associated viral vector, or it can be a non-integrating viral vector, such as an adenoviral vector (e.g., a replication deficient adenovirus vector). Optionally, the nucleic acid can include a nuclear localization sequence. The nucleic acid typically includes a transcription regulatory sequence, including, for example, a promoter, to control expression of the nucleic acid (e.g., the therapeutic gene) to be expressed. The promoter can be a non-specific viral or non-viral promoter, or it can be a tissue-specific promoter that operates in a selected subset of cells, such as erythroid precursors or undifferentiated or differentiated osteoblast lineage cells. Exemplary promoters include erythroid specific promoters, such as the ankyrin-1 promoter, an α-spectrin promoter, a ξ-globin enhancer and/or sequences derived from the β-globin locus control region (LCR). Inducible or suppressible promoters can also be used to regulate expression of the heterologous nucleic acid. Such promoters are typically ligand-dependent transcription regulators and include, for example, such systems as the Tet/on and Tet/off systems.

For ex vivo application, following introduction of the heterologous nucleic acid that encodes the osteogenic growth factor, the hematopoietic stem cell(s) and/or progeny thereof are introduced into a subject in need of bone formation. For example, subjects that can achieve improved health outcomes by increased bone formation include subjects with osteoporosis and/or osteogenesis imperfecta, as well as subjects with bone fractures, including multiple severe fractures. The transduced cells can be introduced using any means available in the art for transplanting bone marrow cells into a subject for the purpose of subsequent engraftment. For example, the transduced hematopoietic stem cells can be introduced into the peripheral circulation of a subject by injection or transfusion. In the case of in vivo applications, nucleic acids encoding osteogenic growth factors can be introduced directly, either locally or systemically, into cells of a subject without any intermediate step that involves isolation of the hematopoietic stem cells from a subject.

Thus, one aspect of the present disclosure relates to the use of hematopoietic stem cells or hematopoietic progenitor cells expressing osteogenic growth factors for systemic or local skeletal administration, e.g., to the endosteal bone surface of the bone marrow cavity. Hematopoietic stem cells or progenitor cells have the unique property to home to, reside, and engraft in the bone marrow space. Thus, hematopoietic stem or progenitor cells can be used to target delivery of one or more therapeutic genes in the bone marrow to promote systemic and/or local bone formation and fracture healing. The methods described herein can be used to treat bone diseases by expressing osteogenic growth factors in hematopoietic stem cells or hematopoietic progenitor cells, which are administered to a subject where they target bone tissue and promote skeletal growth and/or repair.

For example, one specific osteogenic growth factor for use in the disclosed methods is FGF-2 (and analogs thereof). FGF-2 is known to promote stem cell renewal and is osteogenic. In addition, FGF-2 increases angiogenesis, which is desirable to increase blood supply to new bone. Thus, in one exemplary embodiment, the present disclosure relates to compositions and methods employing FGF-2 and analogs thereof to promote systemic and/or local bone growth. Typically, the secretable analog is selected to have increased stability of the FGF-2 polypeptide as compared to a wild-type FGF-2 polypeptide. Such analogs can include at least one amino acid substitution that confers increased stability in vitro, in vivo, or both in vitro and in vivo. For example, the FGF-2 analog can include amino acid substitutions for cysteines at one or more of amino acid positions 70 (C2) and/or 88 (C3). The substituted amino acids can be nonglycosylatable or glycosylatable amino acids. Examples of suitable substitutions for cysteines at positions 70 and/or 88 include serine, asparagine and alanine. In one embodiment, the secretable analog of FGF-2 is encoded by a nucleic acid that includes in a 5' to 3' direction: a polynucleotide that encodes a secretion signal sequence and a polynucleotide sequence that encodes a mature FGF-2 polypeptide. For example, the secretion signal sequence can be a BMP2/4 hybrid secreation signal sequence. The polynucleotide that encodes the FGF-2 analog can be operably linked to a constitutive (such as a non-viral or viral, e.g., CMV, promoter), tissue specific (including erythroid specific and osteoblast specific promoters) or regulatable promoter (for example, Tet-on and Tet-off). Optionally, the nucleic acid can include additional polynucleotide sequences such vector sequences, and or additional sequences that facilitate secretion and/or processing, such as an FGF-2 propeptide encoding sequence. Such FGF-2 analogs and nucleic acids that encode them are also features of this disclosure.

Another aspect of the present disclosure relates to a new animal model of bone marrow transplantation. The transgenic model system presented herein overcomes many of the difficulties inherent in previous animal bone marrow transplantation models. The model system involves transplantation and engraftment of donor hematopoietic stem cells and/or hematopoietic progenitor cells into an immunologically compatible, sublethally irradiated, myelosuppressed recipient mouse. The methods involve transplanting at least about 100,000 donor cells, such as about 400,000 donor cells per recipient.

For example, the donor cells can be pluripotent hematopoietic stem cells or embryonic stem cells, such as Sca-1$^+$ hematopoietic stem cells, isolated from bone marrow, spleen and/or peripheral blood of a donor mouse. In some embodiments, the Sca-1$^+$ hematopoietic stem cells are constituents of a population of cells enriched for Sca-1$^+$ cells. The population of cells can, for example, be enriched using magnetic beads conjugated with an antibody specific for Sca-1.

The donor cells are genetically and/or phenotypically distinguishable from the recipient's cells. In certain embodiments, the donor cells are phenotypically distinguishable from the cells of the recipient. For example, the donor cells can express a transgene that encodes a detectable product or an enzyme that is capable of converting a substrate into a detectable product. The detectable product can be optically detectable, for example the optically detectable product can be a green fluorescent protein (GFP), such as an enhanced GFP.

Typically, donor(s) and recipient(s) are immunologically compatible. For example, the donor and recipient mice can be syngeneic. To enhance engraftment, the recipient mouse is genetically myelosuppressed. In an embodiment, the recipient mice have a mutation at the W locus (for example, the recipient mice can be $W^{41}/W^{41}$ homozygous mice). The recipient mice are typically conditioned with low levels of radiation of between 50 and 1000 cGy, such as at least about 100 cGy, or at least about 200 cGy. In a specific example, the dose of irradiation is approximately 500 cGy. For example the recipient mouse can be irradiated using a $^{60}$Cobalt source and delivering from about 50 cGy to about 100 cGy per minute (e.g., approximately 80 cGy) until the desired dose of irradiation is obtained. Typically, the donor cells are transplanted after a period of recovery. For example, the donor cells can be transplanted at least 2 hours, or at least 4 hours or up to about 24 hours after sublethally irradiating the recipient mouse.

Engraftment is obtained by transplanting the donor cells into the recipient, e.g., via retroorbital injection. This approach yields chimeric mice. When eGFP transgenic donor mice are utilized, GFP expression can be used to monitor engraftment and to follow cell fate of donor cells, enabling monitoring and evaluation of stem cell expansion in recipient mice. Thus, in one specific embodiment, the disclosure provides a $W^{41}/W^{41}$ mouse with a chimeric bone marrow that includes hematopoietic stem cells, hematopoietic progenitor cells and/or osteoblast lineage cells derived by descent from a donor cell that expresses an enhanced green fluorescent protein (eGFP).

Accordingly, this animal model provides an improved means of screening for genes, proteins, and/or other agents that stimulate stem cell renewal and bone and other tissue regeneration. For example, methods for identifying agents that modulate bone growth are provided. For example, the methods involve contacting one or more cells of a recipient mouse with a chimeric bone marrow with an agent, and detecting a change in one or more indicator of bone growth. Exemplary indicators of bone growth include: hematopoietic stem cell survival, hematopoietic progenitor cell survival, osteoblast lineage cell survival, bone marrow engraftment (e.g., by a hematopoietic stem cell, a hematopoietic progenitor cell, and/or an osteoblast lineage cell), expression of one or more genes (in at least one of a hematopoietic stem cell, a hematopoietic progenitor cell and an osteoblast lineage cell), activity of one or more gene product (in at least one of a hematopoietic stem cell, a hematopoietic progenitor cell and/ or an osteoblast lineage cell), angiogenesis, bone metabolism, bone mass, and bone density. By identifying a change in one or more of these parameters an agent is identified that modulates bone growth.

In an embodiment, the cell is contacted with the agent by expressing a transgene, such as a transgene that encodes the agent or a transgene that enzymatically produces the agent, in the cell. In another embodiment, the cell is contacted with a member of a library of compositions.

Additional details regarding the claimed compositions and methods are provided throughout the disclosure. To facilitate review of the various embodiments of this disclosure, the following explanations of specific terms are provided:

Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as a growth factor, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "gene" refers to a functional nucleic acid (e.g., DNA or RNA) sequence. A gene can include coding sequences necessary for the production of a functional RNA or polypeptide (e.g., a protein of interest). The polypeptide can be encoded by a full length coding sequence or by any portion of the coding sequence so long as the desired activity or functional properties (e.g., enzymatic activity, ligand binding, signal transduction) of the full-length polypeptide, or fragment, are retained. The term also encompasses sequences associated with (e.g., contiguous with or adjacent to) a coding region that are involved in regulation of expression of the coding sequence, such as 5' untranslated sequences including for example, a promoter, enhancers and other sequences which serve as the recognition sites for protein factors involved in expression of the polynucleotide sequence. The term gene encompasses both cDNA (complementary DNA) and genomic forms of a gene.

A "transgene" is a heterologous nucleic acid, e.g., a heterologous "gene" introduced into a recipient cell or organism. Such a recipient cell, into which a heterologous nucleic acid has been introduced is referred to as a "host" cell.

A "transformed" cell, or a "host" cell, is a cell into which a nucleic acid molecule (e.g., a transgene) has been introduced by molecular biology techniques. A transformed cell or a host cell can be a bacterial cell or a eukaryotic cell.

A "population" of cells includes any number of cells. Thus, a population of cells can include as few as one cell or can include many cells, for example hundreds, thousands, hundreds of thousands or millions of cells. A "therapeutically effective" population of cells is a population of cells sufficient to provide a desired effect following administration to a subject. The number of cells in a therapeutically effective population of cells is dependent on a number of factors, including the characteristics of the cells, the genetics and/or physiology of the subject to whom the cells are administered, the purpose of the administration and the desired effect.

The terms "transduction," "transfection" and "transformation" refer to the introduction of heterologous DNA/RNA into cells. These terms are used interchangeably to refer to the introduction of nucleic acids into host cells regardless of the methodology used. Common methods for introducing nucleic acids into cells include calcium phosphate-DNA coprecipitation, DEAE-dextran-mediated transfection, polybrene-mediated transfection, electroporation, microinjection, liposome fusion, lipofection, protoplast fusion, transfection with viral vectors, such as retroviral or adenoviral infection, and biolistics.

The term "nucleic acid" refers to a polymer of nucleotides of any length. The term includes single- and double-stranded forms of DNA (deoxyribonucleic acid) and RNA (ribonucleic acid), as well as DNA-RNA hybrids. Generally, the term "nucleic acid" is synonymous with "polynucleotide" or "polynucleotide sequence," unless clearly indicated to the contrary. The repeating units in DNA (RNA) polymers are four different nucleotides, each of which comprises one of the four bases, adenine, guanine, cytosine and thymine (uracyl)

bound to a deoxyribose (ribose) sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed. Unless otherwise specified, any reference to a DNA molecule is intended to include the reverse complement of that DNA molecule. Double-stranded DNA and RNA (dsDNA and dsRNA) have two strands, which can be defined with respect to the products that they encode: a 5'→3' strand, referred to as the plus or "sense" strand, and a 3'→5' strand (the reverse compliment), referred to as the minus or "antisense" strand. Because RNA polymerase adds nucleic acids in a 5'→3' direction, the minus strand of the DNA serves as the template for the RNA during transcription. Thus, the RNA formed has a sequence complementary to the minus strand and identical to the plus strand (except that U is substituted for T). Except where single strandedness is required by context, DNA molecules, although written to depict only a single strand, encompass both strands of a double-stranded DNA molecule.

For convenience, short polynucleotides, typically of less than about 100 nucleotides in length are often referred to as "oligonucleotides." Similarly, very short polymers of two, three, four, five, or up to about 10 nucleotides in length, can conveniently be referred to as dinucleotides, trinucleotides, tetranucleotides, pentanucleotides, etc. The nucleotides can be ribonucleotides, deoxyribonucleotides, or modified forms of either nucleotide.

A "cDNA" or "complementary DNA" is a piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

A "recombinant" polynucleotide includes a polynucleotide that is not immediately contiguous with one or both of the polynucleotide sequences with which it is immediately contiguous (one on the 5' end and one on the 3' end) in the naturally occurring genome of the organism from which it is derived. Thus, a recombinant nucleic acid can include polynucleotide sequences that are "heterologous" with respect to each other. A "heterologous" polynucleotide is a polynucleotide that is not normally (e.g., in the wild-type genomic sequence) found adjacent to a second polynucleotide sequence, or that is not normally found within a particular cell, as the reference indicates. A heterologous nucleic acid or a heterologous polynucleotide can be, but is not necessarily, transcribable and translatable. In some embodiments, a heterologous nucleic acid is a cDNA or a synthetic DNA. In other embodiments, the heterologous polynucleotide sequence is a genomic sequence that encodes an RNA transcript. In other embodiments, a heterologous polynucleotide encodes a marker. Similarly, a recombinant protein is a protein encoded by a recombinant nucleic acid molecule. A recombinant protein can be obtained by introducing a recombinant nucleic acid molecule into a host cell (such as a eukaryotic cell or cell line, such as a mammalian cell or yeast, or a prokaryotic cell, such as bacteria) and causing the host cell to produce the gene product. Methods of causing a host cell to express a recombinant protein are well known in the art (see, e.g., Sambrook et al., *Molecular Cloning: A Laboratory Manual*, 2nd edition, New York: Cold Spring Harbor Laboratory Press, 1989).

An "isolated" biological component (such as a nucleic acid or protein) has been substantially separated or purified away from other biological components in the cell of the organism in which the component naturally occurs, such as, other chromosomal and extrachromosomal DNA and RNA, and proteins. Isolated nucleic acids and proteins include nucleic acids and proteins purified by standard purification methods. The term also embraces nucleic acids and proteins prepared by recombinant expression in a host cell as well as chemically synthesized nucleic acids.

The term "purified" refers to the removal of one or more extraneous components from a sample. The term "purified" does not require absolute purity; rather, it is intended as a relative term. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample. Isolated polypeptides or nucleic acid molecules, typically, comprise at least 50%, at least 60%, at least 70%, at least 80%, at least 90%, at least 95% or even over 99% (w/w or w/v) of a sample.

Similarly, the term "enriched" is a relative term, referring to a proportional increase in a constituent of a sample. For example, a population of cells is enriched for a particular component cell when the number of component cells is increased relative to the total number of cells in a population. For example, the proportion of the component cell in a sample (e.g., as defined by a volume or total number of cells) can be increased by 50% (such as from 10% to 15%) of the total number of cells, or the increase can be more substantial. For example, the proportion of component cells can double or more than double (e.g., increase by 2×, 3×, 4×, 5×, 10×, 20×, 50×, or more). Indeed in some cases, especially when dealing with a component cell that is present at very low frequency in a starting sample, the proportion can increase hundreds of even thousands fold.

Cells, polypeptides and nucleic acid molecules are isolated by methods commonly known in the art and as described herein. Purity of cells, polypeptides or nucleic acid molecules can be determined by a number of well-known methods, such as flow cytometry for cells, polyacrylamide gel electrophoresis for polypeptides, or agarose gel electrophoresis for nucleic acid molecules.

A first polynucleotide sequence is "operably linked" to a second polynucleotide sequence when the first polynucleotide is in a functional relationship with the second polynucleotide. For instance, a coding sequence is operably linked to a transcription control sequence if the transcription control sequence affects (e.g., regulates or controls) the transcription or expression of the coding sequence. When recombinantly produced, operably linked polynucleotides are usually contiguous and, where necessary to join two protein-coding regions, are in the same reading frame. However, polynucleotides need not be contiguous to be operably linked.

A nucleic acid that regulates the expression of a heterologous polynucleotide sequence to which it is operably linked is referred to as an "expression control sequence" or a "transcription control sequence." A transcription control sequence is operably linked to a nucleic acid sequence when the regulatory control sequence controls and regulates the transcription and, as appropriate, translation of the nucleic acid sequence. Thus, transcription regulatory sequences can include appropriate promoters, enhancers, transcription terminators, a start codon (typically, ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences.

A "promoter" is a minimal sequence sufficient to direct transcription of a nucleic acid. Also included are those promoter elements which are sufficient to render promoter-dependent gene expression controllable for cell-type specific, tissue-specific, or inducible by external signals or agents; such elements can be located in the 5' or 3' regions of the gene. Both constitutive and inducible promoters are included (see, e.g., Bitter et al. *Methods in Enzymology* (1987) 153:516-544). For expression in mammalian cell systems, promoters derived from the genome of mammalian cells (for example, metallothionein promoter) or from mammalian viruses (for example, the cytomegalovirus immediate early promoter, the retrovirus long terminal repeat; the adenovirus late promoter; the vaccinia virus 7.5K promoter) can be used. Alternatively, promoters that direct transcription in a selected tissue or set of tissues (tissue specific promoters) can be used. In one example, erythroid specific promoters that direct transcription in cells giving rise to red blood cells are used. Additionally, the promoter can be a regulatable promoter, such as a promoter that is regulated by tetracycline and/or analogs thereof. Promoters produced by recombinant DNA or synthetic techniques can also be used to provide for transcription of the nucleic acid sequences.

"Expression" refers to transcription of a polynucleotide, and when used in reference to a polypeptide, to translation. Expression is the process by which the information encoded by polynucleotide sequence is converted into an operational, non-operational or structural component of a cell. The level or amount of expression is influenced by cis-acting elements and trans-acting binding factors, which are often subject to the influence of intra- and/or extra-cellular stimuli and signals. The response of a biological system, such as a cell, to a stimulus can include modulation of the expression of one or more polynucleotide sequences. Such modulation can include increased or decreased expression as compared to pre-stimulus levels. Expression can be regulated or modulated anywhere in the pathway from DNA to RNA to protein (and can include post-translations modifications, e.g., that increase or decrease stability of a protein).

A polynucleotide sequence is said to "encode" a polynucleotide or polypeptide if the information contained in the nucleotide sequence can be converted structurally or functionally into another form. For example, a DNA molecule is said to encode an RNA molecule, such as a messenger RNA (mRNA) or a functional RNA (such as an inhibitory RNA (iRNA), small inhibitory RNA (siRNA), double stranded RNA (dsRNA), small modulatory RNA (smRNA), antisense RNA (asRNA) or ribozyme, if the RNA molecule is transcribed from the DNA molecule, and contains at least a portion of the information content inherent in the DNA molecule. A DNA or RNA molecule is said to encode a polypeptide, e.g., a protein, if the protein is translated on the basis of a sequence of trinucleotide codons included within the DNA or RNA molecule. Where the coding molecule is a DNA, the polypeptide is typically translated from an RNA intermediary corresponding in sequence to the DNA molecule.

The term "polypeptide" refers to any chain of amino acids, regardless of length or post-translational modification (for example, glycosylation or phosphorylation), such as a protein or a fragment or subsequence of a protein. The term "peptide" is typically used to refer to a chain of amino acids of from about 3 to about 30 amino acids in length.

A "vector" is a nucleic acid as introduced into a host cell, thereby producing a transformed host cell. Exemplary vectors include plasmids, cosmids, phage, animal and plant viruses, artificial chromosomes, and the like. Vectors also include naked nucleic acids, liposomes, and various nucleic acid conjugates. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as, promoters) and are capable of directing the transcription of an expressible nucleic acid sequence that has been introduced into the vector. Such vectors are referred to as "expression vectors." A vector can also include one or more selectable marker genes and/or genetic elements known in the art.

A "marker" is a molecule that serves to distinguish one cell from another. In the context of the present disclosure, a marker serves as an indicator of cell origin unless otherwise indicated. Typically, a marker is selected for ease of detection, e.g., by optical means. Common markers include fluorescent proteins, such as green fluorescent protein (GFP) and numerous variants thereof. Other markers include proteins with enzymatic activities that convert a fluorogenic or chromogenic substrate into a fluorescent or visible product, or that convert an isotopically labeled substrate into a radioactive product. Examples of such enzymatic markers include firefly luciferase, chloramphenicol acetyltransferase (CAT), $\beta$-glucuronidase and $\beta$-galactosidase. A polynucleotide encoding a marker can be operably linked to a transcription control sequence and introduced into cells. Markers also include selectable markers, the activity of which can be measured as relative resistance or sensitivity to a selection agent, such as an antibiotic. Naturally occurring markers include readily detectable traits such as coat (fur) color, polymorphic antigens, and the like. Alternatively, the marker can be a genetic marker such as a nucleic acid polymorphism.

A "stem cell" is an undifferentiated cell, capable of indefinite proliferation and generation of differentiated progeny cells. The term "progeny" of a cell or "progeny cell" refers to a cell generated by one or more cycles of DNA replication and division of a parental cell. In mammalian cells, for example, a single cycle of replication and division typically gives rise to two progeny cells. Subsequent cycles of replication and division give rise to exponentially increasing numbers of progeny cells from a single parental or progenitor cell. The progeny of a stem cell can include additional stems cells. This process is referred to as "self-renewal." Progeny of a stem cell can also include cells of one or more cell lineages or differentiated phenotypes, e.g., hematopoietic cells or osteoblast lineage cells.

Stem cells can be divided into three broad categories on the basis of the variety of differentiated progeny generated by the stem cell. "Totipotent" stem cells, e.g., blastomeres, can give rise to every cell type of an organism. "Pluripotent" stem cells give rise to differentiated cells of any of the three germ layers. "Multipotent" (or "unipotent") stem cells give rise to a limited set of cell types, typically restricted to a single tissue or lineage. Stem cells can be derived or obtained from either embryonic or adult organisms. Embryonic stem ("ES") cells are cells obtained from the inner mass cells of a blastocyst. The term "adult" stem cell refers to undifferentiated cells within a specific tissue, which can be found in and obtained or derived from either adult or immature, including embryonic organisms that have undergone sufficient organogenesis that distinct multicellular tissues and organs can be identified. Such adult stem cells are often multipotent cells.

The term "hematopoietic stem cell" refers to a heterogenous class of cells typically isolated from bone marrow, cord blood, peripheral blood or embryonic liver. Hematopoietic stem cells can be either pluripotent or multipotent stem cell that gives rise to hematopoietic cells, that is, red and white blood cells. Additionally, certain pluripotent hematopoietic stem cells give rise to cells of various lineages and germ layers, including one or more of muscle lineage cells, neural lineage cells and osteoblast lineage cells.

The term "osteoblast" includes bone progenitor cells which have the capacity to form, or to contribute to the formation of, new bone tissue. Osteoblasts include osteocytes and more immature osteoblast lineage cells. The term "cell lineage" refers to the ancestry (that is, the progenitor cell and program of cell divisions) of a cell. Thus, an "osteoblast lineage cell" is any cell that arises by division of a committed osteoblast progenitor, such as a preosteoblast, osteoblast or osteocyte.

The term "osteogenic" in reference to an agent, indicates that the agent induces, promotes or otherwise facilitates bone growth (e.g., new bone formation), maintenance and/or repair. "Bone formation" is a measurable property of bone (skeletal) tissue. Thus, bone formation includes one or more of an increase in cellularity (e.g., increase in the number, survival and/or longevity of hematopoietic stem cells, hematopoietic progenitor cells and/or osteoblast lineage cells) of the bone marrow, an increase in bone mass, and/or an increase in bone density. Bone formation can be monitored or evaluated by measuring (directly or indirectly) one or more indicators of bone growth such as: hematopoietic stem cell survival, hematopoietic progenitor cell survival, osteoblast lineage cell survival, bone marrow engraftment by at least one of a hematopoietic stem cell, a hematopoietic progenitor cell, and an osteoblast lineage cell, expression of one or more genes in at least one of a hematopoietic stem cell, a hematopoietic progenitor cell and an osteoblast lineage cell, activity of one or more gene product (e.g., skeletal alkaline phosphatase) in at least one of a hematopoietic stem cell, a hematopoietic progenitor cell, angiogenesis, bone metabolism, bone mass, and bone density.

In the context of this disclosure, a growth factor is a peptide or polypeptide agent that promotes division (e.g., replication, proliferation) and or differentiation of one or more cells. An osteogenic growth factor is a growth factor that promotes division, differentiation or both division and differentiation, of a progenitor cell into progeny cells that contribute directly or indirectly to bone formation.

The term "mammal" includes both human and non-human mammals. Similarly, the term "subject" or "patient" includes both human and veterinary subjects or patients.

Therapeutic Nucleic Acids

In one aspect, the present disclosure relates to nucleic acids that encode therapeutic transgenes suitable for administration for promoting bone growth (for example, bone formation) in humans and other mammals. The nucleic acids encode osteogenic growth factors that are capable of promoting stem cell renewal, increasing bone formation and, in some cases, enhancing angiogenesis. Exemplary osteogenic growth factors that promote stem cell self-renewal and that enhance bone formation include members of the FGF family of growth factors. For example, FGF family members that bind to and act via FGF-receptors 1, 2 and/or 3, such as FGF-1, FGF-2, FGF-4, and analogs thereof, are osteogenic growth factors. Members of the Wnt family of growth factors (such as Wnts 1, 2, 2B, 3, 3B, 4, 5A, 5B, 6, 7A, 7B, 8A, 8B, 9A, 10A, 10B, 11 and 16) are also among the osteogenic growth factors suitable for use in the methods described herein. Additionally, growth hormone, angiopoietins 1-7 (e.g., Angpt12, Angpt13), glial cell nerve factor, stem cell factor, parathyroid hormone (PTH), insulin like growth factor (IGF), platelet derived growth factor (PDGF), vascular endothelial growth factor (VEGF), Cox-2, and TGF-β are exemplary osteogenic growth factors. Thus, the therapeutic nucleic acids include polynucleotide sequences that encode at least one osteogenic growth factors.

One specific example of an osteogenic growth factor is fibroblast growth factor-2 (FGF-2). The use of FGF-2 serves as an example throughout this disclosure. Nonetheless, one of skill in the art will recognize that any of the growth factors listed above, and indeed any growth factor that satisfies the criteria of promoting self-renewal of hematopoietic stem cells, enhancing bone formation in vivo, and optionally, promoting angiogenesis in vivo is a suitable osteogenic growth factor in the methods disclosed herein.

The nucleotide and amino acid sequences of human FGF-2 are represented by SEQ ID NO:1 and SEQ ID NO:2, respectively. While the compositions and methods are described with respect to the human FGF-2 homolog, which is particularly suited for administration to human subjects, the compositions and methods disclosed herein are equally applicable to other mammalian FGF-2 orthologs, which can be selected by one of skill to correspond to the subject to which the nucleic acid, protein or cell is to be administered. Thus, for example, if the subject is a domestic livestock animal, such as a cow, a pig or a sheep, the FGF-2 nucleic acid can be selected from nucleic acids represented by GENBANK® accession nos: AX085265, AJ577089, and NM_001009769, respectively. Similarly, suitable FGF-2 homologs can be selected, and analogs produced, corresponding to any species of interest.

Exemplary analogs include modified FGF-2 nucleic acids and proteins that have been modified to include a signal peptide that promotes secretion of the translated FGF-2 product. One suitable secretion signal sequence is a hybrid BMP2/4 secretion signal sequence as represented by SEQ ID NO: 5 (nucleotide) and SEQ ID NO:6 (amino acid), which facilitates secretion of the translated product. The nucleotide and amino acid sequences of an exemplary FGF-2 analog are provided in SEQ ID NO:3 and SEQ ID NO:4, respectively. A FGF-2 analog can include one or more amino acid substitutions (or additions or deletions) that increases stability of the secreted protein, typically without altering its activity. For example, one or more cysteine residues (up to all four of the cysteine residues) can be modified as shown in the analog schematically illustrated in FIG. 1A. Typically, the second and third cysteines, that is, cysteines at positions 70 and 88 are mutated. For example, suitable mutations include cysteine to serine substitutions and cysteine to asparagine substitutions.

Therapeutic nucleic acids encoding a growth factor suitable for increasing bone growth, such as FGF-2 or an analog thereof include deoxyribonucleotides (DNA, cDNA) or ribodeoxynucletides (RNA) sequences, or modified forms of either nucleotide, which encode the fusion polypeptides described herein. The term includes single and double stranded forms of DNA and/or RNA.

Polynucleotide sequences described herein include polynucleotide sequences, such as the sequences represented by SEQ ID NO:1 and 3, which encode FGF-2 and an exemplary analog, as well as polynucleotide sequences complementary thereto. For example, a polynucleotide that encodes a modified FGF-2 amino acid sequence represented by SEQ ID NO:4 is a feature of this disclosure.

In addition to the polynucleotide sequences represented by SEQ ID NOS:1 and 3, and the amino acid sequences represented by SEQ ID NOS:2 and 4, polynucleotide and amino acid sequences that are substantially identical to these polynucleotide sequences can be used in the compositions and methods of the disclosure. For example, a substantially identical sequence can have one or a small number of deletions, additions and/or substitutions. Such nucleotide and/or amino acid changes can be contiguous or can be distributed at different positions within the nucleic acid or protein. A substantially identical sequence can, for example, have 1, or 2, or 3, or 4, or even more nucleotide or amino acid deletions, additions and/or substitutions. Typically, the one or more deletions, additions and/or substitutions do not alter the reading frame encoded by a polynucleotide sequence, such that a modified ("mutant") but substantially identical polypeptide is produced upon expression of the nucleic acid.

The similarity between polynucleotide and/or amino acid sequences is expressed in terms of the similarity between the sequences, otherwise referred to as sequence identity. Sequence identity is frequently measured in terms of percentage identity (or similarity); the higher the percentage, the more similar are the primary structures of the two sequences. Thus, a polynucleotide that encodes FGF or an FGF-2 analog (or another osteogenic growth factor) can be at least about 95%, or at least 96%, frequently at least 97%, 98%, or 99% identical to SEQ ID NO:1 (or SEQ ID NO:3 or the corresponding growth factor encoding polynucleotide) or to at least one subsequence thereof. Methods of determining sequence identity are well known in the art. Various programs and alignment algorithms are described in: Smith and Waterman, *Adv. Appl. Math.* 2:482, 1981; Needleman and Wunsch *J. Mol. Biol.* 48:443, 1970; Higgins and Sharp *Gene* 73:237, 1988; Higgins and Sharp *CABIOS* 5:151, 1989; Corpet et al. *Nucleic Acids Research* 16:10881, 1988; and Pearson and Lipman *Proc. Natl. Acad. Sci. USA* 85:2444, 1988. Altschul et al. *Nature Genet.* 6:119, 1994 presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Thus, a sequence (that is a polynucleotide or polypeptide sequence) that is substantially identical, or substantially similar polynucleotide to a polynucleotide of SEQ ID NO:1, 3, or 5 (or to a polypeptide sequence of SEQ ID NO:2, 4 or 6) is encompassed within the present disclosure. Such polynucleotides can include, e.g., insertions, deletions, and substitutions relative to any of SEQ ID NOs:1, 3 and/or 5. For example, such polynucleotides are typically at least about 70% identical to a reference polynucleotide (or polypeptide) selected from among SEQ ID NO:1 through SEQ ID NO:5. That is, at least 7 out of 10 nucleotides (or amino acids) within a window of comparison are identical to the reference sequence selected SEQ ID NO:1-5. Frequently, such sequences are at least about 80%, usually at least about 90%, and often at least about 95%, or more identical to a reference sequence selected from SEQ ID NO:1 to SEQ ID NO:5. For example, the amino acid or polynucleotide sequence can be 96%, 97%, 98% or even 99% identical to the reference sequence, e.g., at least one of SEQ ID NO:1 to SEQ ID NO:5

Another indicia of sequence similarity between two nucleic acids is the ability to hybridize. The more similar are the sequences of the two nucleic acids, the more stringent the conditions at which they hybridize. Substantially similar or substantially identical nucleic acids to SEQ ID NO:1 and 3 (and to subsequences thereof) include nucleic acids that hybridize under stringent conditions to any of these reference polynucleotide sequences. Thus, a nucleic acid that hybridizes under stringent conditions to a reference polynucleotide sequence selected from among SEQ ID NOs:1 and 3 is substantially identical or substantially similar to the polynucleotides encoding FGF-2 and/or an analog thereof.

The stringency of hybridization conditions are sequence-dependent and are different under different environmental parameters. Thus, hybridization conditions resulting in particular degrees of stringency vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, 2001, NY; Tijssen, *Hybridization With Nucleic Acid Probes, Part I: Theory and Nucleic Acid Preparation*, Laboratory Techniques in Biochemistry and Molecular Biology, Elsevier Science Ltd., NY, 1993, and Ausubel et al. *Short Protocols in Molecular Biology*, 4$^{th}$ ed., John Wiley & Sons, Inc., 1999.

For purposes of the present disclosure, "stringent conditions" encompass conditions under which hybridization occurs only if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch do not hybridize; conditions of "medium stringency" are those under which molecules with more than 15% mismatch do not hybridize, and conditions of "high stringency" are those under which sequences with more than 10% mismatch do not hybridize. Conditions of "very high stringency" are those under which sequences with more than 6% mismatch do not hybridize. In contrast nucleic acids that hybridize under "low stringency conditions include those with much less sequence identity, or with sequence identity over only short subsequences of the nucleic acid.

For example, in nucleic acid hybridization reactions, the conditions used to achieve a particular level of stringency varies depending on the nature of the nucleic acids being hybridized. The length, degree of complementarity, nucleotide sequence composition (e.g., GC v. AT content), and nucleic acid type (e.g., RNA versus DNA) of the hybridizing regions of the nucleic acids all influence the selection of appropriate hybridization conditions. Additionally, whether one of the nucleic acids is immobilized, for example, on a filter can impact the conditions required to achieve the desired stringency.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of skill in the art can readily determine variations on these conditions (e.g., with reference to Sambrook, Tjissen and/or Ausubel, cited above). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions vary, depending on the particular hybridization reaction involved, and can be determined empirically.

Additionally, the nucleic acid encoding the osteogenic growth factor polypeptides can also include polynucleotide sequences, such as expression regulatory sequences and/or vector sequences that facilitate the expression or replication of the nucleic acids. Similarly, the nucleic acid encoding the growth factors can include additional coding sequences that confer functional attributes on the encoded polypeptide. Such sequences include secretion signal sequences (as shown in FIG. 1A and SEQ ID NO:3).

Nucleic acids encoding growth factors that enhance bone growth can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification. These procedures are well known to those of ordinary skill in the art, and exemplary protocols can be found, e.g., in Sambrook and Ausubel (supra).

A polynucleotide sequence (or portions derived from it) such as a cDNA encoding an osteogenic growth factor can be introduced into a vector, such as a eukaryotic expression vector, by conventional techniques. An expression vector is designed to permit the transcription of the polynucleotide sequence encoding the growth factor in cells by providing regulatory sequences that initiate and enhance the transcription of the cDNA and ensure its proper splicing and polyadenylation. Numerous expression vectors are known to those of skill in the art, and are available commercially, or can be assembled from individual components according to conventional molecular biology procedures, such as those described in, e.g., Sambrook and Ausubel, cited above. The pY vectors (MLV-based vectors) described in the Examples is one such suitable expression vector. Numerous other suitable vectors can be selected by those of ordinary skill in the art.

The location of expression of the heterologus nucleic acid, e.g., FGF-2 or an analog thereof, or another bone promoting factor, is dependent (at least in part) on the promoter used to regulate expression of the encoded product. When a non-tissue specific promoter is used, the expression occurs predominantly in the red marrow-rich regions, and at low levels in circulating blood. Similarly, when an erythroid (e.g., erythroblast) specific promoter is employed, expression of the nucleic acid is concentrated in the red marrow areas. In contrast, when an osteoblast specific promoter is employed, expression is restricted to the areas enriched with osteoblasts and/or their precursors. In specific embodiments, the promoters used to direct expression of a polynucleotide that encodes an osteogenic growth factor is an erythroid specific promoter that effectively directs expression in hematopoietic stem cells, such as the ankyrin-1 promoter, an α-spectrin promoter, a ξ-globin enhancer and/or sequences derived from the β-globin locus control region (LCR).

For example, the cytomegalovirus ("CMV") immediate early promoter is a strong constitutive promoter, which can be utilized to control transcription of an osteogenic growth factor upon introduction of an expression vector containing a nucleic acid encoding the osteogenic growth factor operably linked to the CMV promoter. Additionally, vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci. USA* 78:6777-6781, 1982). Alternatively, the level of expression of the polynucleotide that encodes the growth factor can be manipulated by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, 1985, CSHL Press, Cold Spring Harbor, N.Y.).

Optionally, an inducible or otherwise regulatable promoter is utilized. For example, when the goal is fracture repair, the therapeutic gene is introduced into the host cells operably linked to a transcription control sequence that can be "turned on" upon administration of an inducing agent. One exemplary inducible promoter includes a Tetracycline inducible element (e.g., a Tet/on transcription control sequence). Following introduction of the cells, tetracycline is administered, which results in the induction of expression. Once the therapeutic goal is obtained, e.g., fracture repair, attainment of a desired bone mass, the administration of the inducing agent stops (for example, the subject ceases to take tetracycline), and expression of the heterologous nucleic acid ceases. Optionally, where even tighter regulation of expression is desired, a suicide gene can be introduced into the host cells along with the therapeutic nucleic acid. Expression of the suicide gene can be induced once the therapeutic goal is reached, and the host cells are thereby eliminated.

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell. Biol.* 1:486, 1981) or Epstein-Barr (Sugden et al., *Mol. Cell. Biol.* 5:410, 1985). Alternatively, the vector can be selected to be integrated into genomic DNA. In either case, the introduced nucleic acid can be expressed on a continuous basis.

Vector systems suitable for the expression of polynucleotides encoding osteogenic growth factors include, in addition to the specific vectors described in the examples, the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). The present disclosure, thus, encompasses recombinant vectors that comprise all or part of the polynucleotides encoding osteogenic growth factors, for expression in a suitable host, either alone or as a labeled or otherwise detectable protein.

Osteogenic Growth Factors

Another aspect of the disclosure relates to osteogenic growth factors and methods for delivering them to the bone marrow of a subject to increase bone formation. The disclosed osteogenic growth factors promote stem cell self-renewal and enhance bone formation in vivo. Optionally, such growth factors promote angiogenesis in vivo. Exemplary osteogenic growth factors include members of the FGF family of growth factors. For example, FGF family members that bind to and act via FGF-receptors 1, 2 and/or 3, such as FGF-1, FGF-2, FGF-4, and analogs thereof, are used. In other embodiments, the osteogenic growth factors are members of the Wnt family of growth factors (such as Wnts 1, 2, 2B, 3, 3B, 4, 5A, 5B, 6, 7A, 7B, 8A, 8B, 9A, 10A, 10B, 11 and 16). In alternative embodiments, the osteogenic growth factor is selected from among growth hormone (such as human growth hormone), angiopoietins 1-7 (e.g., Angpt12, Angpt13), glial cell nerve factor, stem cell factor, parathyroid hormone (PTH), insulin like growth factor (IGF), platelet derived growth factor (PDGF), vascular endothelial growth factor (VEGF), Cox-2, and TGF-β. These growth factors are well known in the art, and their amino acid sequences are readily accessible from publicly available databases, such as GENBANK®. One of skill in the art can easily obtain the amino acid of (and polynucleotide sequence that encodes) numerous such osteogenic growth factors by searching using the name (e.g., FGF-1 or fibroblast growth factor 1, etc.), or by entering all or a portion of an amino acid or polynucleotide sequence encoding the factor of interest. In addition to the wild-type or naturally occurring versions of the molecules listed above, substantially similar polypeptides are also osteogenic growth factors.

Substantially similar polypeptides can include variant polypeptides that share a substantial percentage of sequence similarity and that retain one or more functions of the reference polypeptide. Variants that retain some or all of the functional attributes of the reference osteogenic growth factor are generally referred to as analogs. In some cases an analog of an osteogenic growth factor has increased activity in vitro, ex vivo, and/or in vivo as compared to the naturally occurring growth factor. Variants that retain some or all of the function of a reference growth factor typically possess no more than a small number of amino acid substitutions (for example, 1, 2, 3, 4, 5, or 10 amino acid substitutions). The variant polypeptides typically have no more than 1% or 2% or 3% or 4% or 5%, or no more than about 10% amino acid differences with respect to the reference growth factor polypeptide. That is, the variant or analog polypeptide is at least about 90%, and typically at least about 95%, or 96%, or 97%, or 98%, or even 99% identical to the reference growth factor. Accordingly, an osteogenic growth factor and related variants or analogs are typically encoded by polynucleotide sequences with a high degree of sequence identity. Nonetheless, substantial divergence in the polynucleotide sequence can occur due to the degeneracy of the genetic code without losing identity between the encoded products. More importantly, with respect to the encoded protein, even where an amino acid substitution is introduced, the mutation can be "conservative" and have no material impact on the essential functions of a protein. See Stryer, *Biochemistry* 3rd Ed., 1988.

Modifications of a polypeptide that involve the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions.

TABLE 1

Blosum Matrix of conservative amino acid substitutions.

| Amino Acid | Conservative Substitutions |
|---|---|
| G | A, S, N |
| P | E |
| D | S, K, Q, H, N, E |
| E | P, D, S, R, K, Q, H, N |
| N | G, D, E, T, S, R, K, Q, H |
| H | D, E, N, M, R, Q |
| Q | D, E, N, H, M, S, R, K |
| K | D, E, N, Q, R |
| R | E, N, H, Q, K |
| S | G, D, E, N, Q, A, T |
| T | N, S, V, A |
| A | G, S, T, V |
| M | H, Q, Y, F, L, I, V |
| V | T, A, M, F, L, I |
| I | M, V, Y, F, L |
| L | M, V, I, Y, F |
| F | M, V, I, L, W, Y |
| Y | H, M, I, L, F, W |
| W | F, Y |
| C | None |

For example, one exemplary osteogenic growth factor is FGF-2 (SEQ ID NO:2). An exemplary polynucleotide sequence that encodes FGF-2 is shown in SEQ ID NO:1). One or more amino acid changes, or up to ten amino acid changes (e.g., two substituted amino acids, three substituted amino acids, four substituted amino acids, or five substituted amino acids, etc.) can be made in the polypeptide without losing function of the osteogenic growth factor.

For example, to improve stability of the osteogenic growth factor, FGF-2, an analog is produced that has an amino acid substituted for one or more of the cysteines of wild type FGF-2. One cysteine can be substituted with another amino acid residue. Alternatively, two cysteines can be substituted with other amino acid residues. If desired, three or even four of the cysteines can be substituted with other amino acids. For example, in certain embodiments, a cysteine at position 70 is substituted by another amino acid, or a cysteine at position 88 is substituted by another amino acid, or cysteines at both position 70 and position 88 are substituted by other amino acids. For example, stability can be increased by substituting an amino acid that capable of glycosylation (either by N-linked or O-linked glycosylation). One specific analog of FGF-2 is depicted in SEQ ID NO:4 (encoded by the polynucleotide sequence of SEQ ID NO:3, or a polynucleotide sequence that differs from SEQ ID NO:3 solely due to the degeneracy of the genetic code). To enhance secretion of the FGF-2 analog, a secretion signal sequence (BMP2/4 hybrid secretion signal) was added to the variant FGF-2. Similar amino acid substituted analogs can be made for any osteogenic growth factor, and the function confirmed without undue experimentation (e.g., by expressing a transgene encoding the growth factor or analog in transplanted cells using the mouse bone marrow transplantation model disclosed herein.

More substantial changes in a biochemical function or other protein features can be obtained by selecting amino acid substitutions that are less conservative than those listed in Table 1. Such changes include, for example, changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Additionally, part of a polypeptide chain can be deleted without impairing or eliminating all of its functions. Similarly, insertions or additions can be made in the polypeptide chain, for example, adding epitope tags, without impairing or eliminating its functions (Ausubel et al. (1997) *J. Immunol.* 159:2502). Other modifications that can be made without materially impairing one or more functions of a polypeptide include, for example, in vivo or in vitro chemical and biochemical modifications that incorporate unusual amino acids. Such modifications include, for example, acetylation, carboxylation, phosphorylation, glycosylation, labeling, e.g., with radionuclides, and various enzymatic modifications, as will be readily appreciated by those of ordinary skill in the art. A variety of methods for labeling polypeptides and labels useful for such purposes are well known in the art, and include radioactive isotopes such as $^{32}$P, fluorophores, chemiluminescent agents, enzymes, and antiligands.

Therapeutic Methods

The compositions and methods described herein can be used to express osteogenic growth factors (such as FGF-2 or an analog thereof) in hematopoietic stem cells and/or hematopoietic progenitor cells for therapeutic or prophylactic treatment of a condition or disease affecting bone metabolism, for example bone growth (e.g., bone formation), bone maintenance and/or bone repair. For example, vectors for administering expressible nucleic acids with a beneficial (for example, therapeutic) effect on bone tissue can be generated by incorporating a polynucleotide sequence that encodes an osteogenic growth factor operably linked to a constitutive, tissue specific or inducible promoter. When introduced into hematopoietic stem cells, which are capable of homing to and engrafting the bone marrow, such expressible nucleic acids are expressed in skeletal tissue, reducing safety concerns and increasing efficacy of delivery. Such applications can be used in the treatment of a condition or disease characterized by impaired bone formation, e.g., due to aging, hormonal status, or genetic or physiological disorders, e.g., osteoporosis, osteogenesis imperfecta. This therapy utilizing osteogenic growth factors can also be used to enhance wound healing, especially the healing of bone fractures.

The nucleic acid encoding the selected osteogenic growth factor can be introduced into a hematopoietic stem cell or progenitor cells in the form of a naked linear double stranded DNA. The polynucleotide sequence encoding the osteogenic growth factor can be incorporated into a vector. Numerous suitable vectors are known in the art, and include, for example, plasmids, viral vectors, and artificial chromosomes. For example, viral vectors are commonly used for in vivo or ex vivo targeting and therapy procedures are retroviral and DNA-based vectors. Methods for constructing and using viral vectors are known in the art (See e.g., Miller and Rosman, *BioTech.*, 7:980-990, 1992). Preferably, the viral vectors are replication defective, that is, they are unable to replicate autonomously in the target cell. In general, the genome of the replication defective viral vectors that are used within the scope of the present disclosure lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques can be performed in vitro (i.e, on the isolated DNA).

In some cases, the replication defective virus retains the sequences of its genome that are necessary for encapsidating the viral particles. DNA viral vectors commonly include an attenuated or defective DNA viruses, including, but not limited to, herpes simplex virus (HSV), papillomavirus, Epstein Barr virus (EBV), adenovirus, adeno-associated virus (AAV), Moloney leukemia virus (MLV) and human immunodeficiency virus (HIV) and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. *Mol. Cell. Neurosci.*, 2:320-330, 1991), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (*J. Clin. Invest.*, 90:626-630 1992; La Salle et al., *Science* 259:988-990, 1993); and a defective adeno-associated virus vector (Samulski et al., *J. Virol.*, 61:3096-3101, 1987; Samulski et al., *J. Virol.*, 63:3822-3828, 1989; and Lebkowski et al., *Mol. Cell. Biol.*, 8:3988-3996, 1988).

For example, the gene can be introduced in a retroviral vector (e.g., as described in U.S. Pat. Nos. 5,399,346, 4,650, 764, 4,980,289 and 5,124,263; all of which are herein incorporated by reference; Mann et al., *Cell* 33:153, 1983; Markowitz et al., *J. Virol.*, 62:1120, 1988; PCT/US95/14575; EP 453242; EP178220; Bernstein et al. *Genet. Eng.*, 7:235, 1985; McCormick, *BioTechnol.*, 3:689, 1985; WO 95/07358; and Kuo et al. *Blood* 82:845, 1993). Most retroviruses are integrating viruses that infect dividing cells. The Lentiviruses are integrating viruses that infect nondividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. The gag, pol and env genes are coexpressed in the packaging cell line. These vectors can be constructed from different types of retrovirus, such as, HIV, MoMuLV ("murine Moloney leukemia virus" MSV ("murine Moloney sarcoma virus"); RSV ("Rous sarcoma virus"). In general, in order to construct recombinant retroviruses containing a nucleic acid sequence, a plasmid is constructed that contains the LTRs, the encapsidation sequence and the construct of the present disclosure comprising a nuclear targeting signal and a coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that can include a part of the gag gene (Bender et al., *J. Virol.*, 61:1639, 1987). Recombinant retroviral vectors are purified by standard techniques known to those having ordinary skill in the art.

In one embodiment, the vector is an adenovirus vector. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2 or type 5 human adenoviruses (Ad 2 or Ad 5), or adenoviruses of animal origin (See e.g., WO94/26914). Those adenoviruses of animal origin that can be used within the scope of the present disclosure include adenoviruses of canine, bovine, murine (e.g., Mav1, Beard et al. *Virol.*, 75-81, 1990), ovine, porcine, avian, and simian (e.g., SAV) origin. In some embodiments, the adenovirus of animal origin is a canine adenovirus, such as a CAV2 adenovirus (e.g. Manhattan or A26/61 strain (ATCC VR-800)).

The replication defective adenoviral vectors described herein include the ITRs, an encapsidation sequence and the nucleic acid of interest. In some embodiments, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions can also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In other embodiments, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO95/02697 and WO96/22378. In still another embodiment, the adenoviral vector has a deletion in the E1 region into which the E4 region and the nucleic acid sequence are inserted.

The replication defective recombinant adenoviruses according to this disclosure can be prepared by any technique known to the person skilled in the art (See e.g., Levrero et al. *Gene* 101:195, 1991; EP 185 573; and Graham *EMBO J.*, 3:2917, 1984). In particular, they can be prepared by homologous recombination between an adenovirus and a plasmid, which includes, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that can be used are the human embryonic kidney cell line 293 (Graham et al. *J. Gen. Virol.* 36:59, 1977), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

For in vivo administration, an appropriate immunosuppressive treatment can be employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

It is also possible to introduce the vector in vivo as a naked DNA plasmid. Methods for formulating and administering naked DNA to mammalian muscle tissue are disclosed in U.S. Pat. Nos. 5,580,859 and 5,589,466. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931). Thus, the nucleic acids that encode osteogenic growth factors can be introduced into cells in the form of naked or complexed DNA according to the teachings of these references, which are incorporated herein by reference.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. *Proc. Natl. Acad. Sci. USA* 84:7413-7417, 1987; Mackey, et al. *Proc. Natl. Acad. Sci. USA* 85:8027-8031, 1988; Ulmer et al. *Science* 259:1745-1748, 1993). The use of cationic lipids can promote encapsulation of negatively charged nucleic acids, and also promote fusion with negatively charged cell membranes (Felgner and Ringold *Science* 337:387-388, 1989). Particularly useful lipid compounds and compositions for transfer of nucleic acids are described in WO95/18863 and WO96/17823, and in U.S. Pat. No. 5,459,127, herein incorporated by reference.

DNA vectors can be introduced into the desired host cells by methods known in the art, including but not limited to transfection, electroporation (for example, into cells ex vivo or in vivo using transcutaneous electroporation), microinjection, transduction, cell fusion, DEAE dextran, calcium phosphate precipitation, use of a gene gun, or use of a DNA vector transporter (See e.g., Wu et al. *J. Biol. Chem.*, 267:963-967, 1992; Wu and Wu *J. Biol. Chem.*, 263:14621-14624, 1988; and Williams et al. *Proc. Natl. Acad. Sci. USA* 88:2726-2730, 1991). Receptor-mediated DNA delivery approaches can also be used (Curiel et al. *Hum. Gene Ther.*, 3:147-154, 1992; and Wu and Wu, *J. Biol. Chem.*, 262:4429-4432, 1987).

According to the methods disclosed herein, a nucleic acid encoding an osteogenic growth factor is introduced into a hematopoietic stem cell or a hematopoietic progenitor cell that is capable of homing to and engrafting the bone marrow following introduction into a subject. The hematopoietic stem cells selected as donor cells can be derived from sources other than the subject to be treated, such as a histocompatible donor. In order to maximize the likelihood of stable bone marrow engraftment and survival of the transplanted cells, it is generally preferable to obtain donor cells from the subject (that is, autologous donor cells). Suitable donor cells can be obtained from the subject's bone marrow or peripheral blood (including cord blood if available). For example, hematopoietic stem cells, such as $CD34^+$ or $Sca-1^+$ stem cells, can be isolated from bone marrow (or peripheral or cord blood) and enriched, e.g., using magnetic beads conjugated to an anti CD34 or anti-Sca-1 antibody. For example, human stem cells that are $CD34^+$, $AC133^+$, $lin^-$, $CD45^-$, $CXCR4^+$ (Kucia et al., *Leukemia* 19:1118-1177, 2005) can be used in the context of the methods disclosed herein as vehicles to express osteogenic growth factors encoded by heterologous nucleic acids. Importantly, such cells are capable of expressing therapeutic nucleic acids at appropriate levels, home to bone marrow throughout the entire skeleton, undergo stem cell renewal under appropriate conditions (e.g., exposure to FGF), and give rise to cells of the osteoblastic lineage. Additionally, hematopoietic stem cells characterized as $CD34^+/CD38^+$ cells (Chen et al., *Stem Cells* 15:368-377, 1997); $CD73^+$, $STRO-1^+$, $CD105^+$, $CD34^-$, $CD45^-$, $CD144^-$ cells (Tuli et al., *Stem Cells* 21:681-693); and $CD29^+$, $CD63^+$, $CD81^+$, $CD122^+$, $CD164^+$, $cMet^+$, bone morphogenetic protein receptor $1B^+$, and neurotrophic tyrosine kinase receptor $3^+$ and $CD34^-$, $CD36^-$, $CD45^-$, $CD117^-$ ($cKit^-$), and $HLA-DR^-$ (D'Ippolito et al., *Journal of Cell Science* 117:2971-2981, 2004) are also human pluripotent hematopoietic stem cells. In certain embodiments, the hematopoietic stem cells express CXCR4, which facilitates homing to the bone marrow. Additionally, the stem cells can express one or more FGF receptors. Alternatively, CXCR4 expressing stem cells other than hematopoietic stem cells, such as endothelial stem cells or mesenchymal stem cells can be used.

Such cells are suitable donor cells in the context of the methods and compositions described herein. Alternatively, embryonic stem cells can be employed as donor cells to increase bone growth and/or enhance healing.

To increase the recovery of autologous hematopoietic stem cells, a subject can be treated with a growth factor that promotes expansion of hematopoietic lineage cells, such as granulocyte colony stimulating factor (GCSF), granulocyte macrophage colony stimulating factor (GMCSF) or erythropoietin (EPO), or a combination of two or more of GCSF, GMCSF and EPO, to stimulate formation of red marrow throughout the skeleton. Hematopoietic stem cells and/or hematopoietic progenitors can then be recovered in increased numbers by standard procedures, such as apheresis. A nucleic acid encoding FGF-2 or an analog thereof, or another factor that promotes increased bone growth is introduced into the hematopoietic stem or progenitor cells as discussed above, and the cells are then introduced into the subject, e.g., injected or transfused intravenously using standard procedures employed in the art for bone marrow transplantation. Hematopoietic stem cells are capable of achieving systemic engraftment even when relatively small numbers of cells are introduced. For example, as few as 1000 to 10,000 transduced $CD34^+$, $CXCR4^+$ stem cells can be transplanted into a subject. More commonly, however, at least a million transduced CD34+ cells are introduced into a recipient to effect systemic bone growth and/or enhance wound healing (e.g., of one or multiple fractures). Typically, between 1 and $10 \times 10^6$ $CD34^+$ stem cells are introduced into the subject. Following introduction into the subject, the cells have the ability to seek out (home to) and engraft the bone marrow. The host cells divide within the bone marrow to produce progeny cells, which express the introduced gene, and its protein product, at the endosteal bone surfaces of the bone marrow. Increased expression of such factors induces bone formation, e.g., by stimulating and recruiting nearby stromal cells in the marrow space to mature into osteoblasts.

Because bone growth (and, e.g., repair of bone fractures) is enhanced by mechanical loading of the bone, the methods described above can be combined with regimens involving or simulating physical loading of the bone. Such therapies increase bone growth at the desired locations within the skeletal system, and can be accomplished even in subjects that are immobilized or otherwise unable to undergo substantial physical activity. In addition to exercise, and/or physical therapy, treatment modalities employing vibration, e.g., ultrasound vibration, have been found to simulate mechanical loading and enhance bone growth. Additionally, because the methods described herein result in rapid and substantial bone growth, these therapies are most advantageously combined with administration of calcium and vitamin D at levels sufficient to prevent calcium deficiency that may otherwise occur with intense bone formation. For example, calcium intake can be coordinated with the degree or intensity of the formation to avoid calcium deficiency. In addition, to optimize the effects of the osteogenic growth factor expressed by the hematopoietic stem cell and its progeny, in some cases additional growth factors (including for example, osteogenic growth factors and cytokines). Accordingly, the compositions and methods for disclosed herein are suitable for treating subjects with bone wasting and/or bone fragility disorders, regardless of age, gender, or mobility status.

Bone Marrow Transplantation Model

Another aspect of the present disclosure relates to a novel bone marrow transplantation model. Gene and cell therapies via bone marrow transplantation (BMT) represents an exciting approach for treating numerous medical conditions, including, but not limited to, hereditary immunodeficiencies (Yang, *Med. Sci. Monit.* 10(7):RA155-165, 2004; Buckley, *Annu. Rev. Immunol.* 22:625-655, 2004; Fischer et al., *Semin. Hematol.* 41(4):272-278, 2004), hemoglobinopathies (Puthenveetil et al., *Curr. Hematol. Rep.* 3(4):298-305, 2004), cancers (Fuchs, *Curr. Opin. Mol. Ther.* 6(1):48-53, 2004), and skeletal disorders (Klamut et al., *Crit. Rev. Eurkaryot. Gene Expr.* 14(1-2):89-136, 2004). Prior to clinical trials of these applications in humans, appropriate animal models are used to further assess therapeutic efficacy and safety monitoring. Accordingly, a number of BMT animal models have been developed. The most widely studied animal model of BMT, e.g., for gene therapy, is the murine hematopoietic stem cells (HSCs) transplantation model.

Long-term engraftment of donor cells is essential for the success of BMT-based approaches. BMT engraftment is affected by a number of variables, such as recipient preconditioning, HSC numbers and purity, route of delivery of donor cells, and ancillary treatments of HSCs. Accordingly, there have been a number of variations in strategy of this model addressing some of the variables to enhance engraftment. Each variation in strategy has its own advantages and disadvantages. For example, engraftment has been demonstrated in non-myeloablated recipients in some studies (Micklem et al., *Transplantation* 6(2):299-302, 1968; Brecher et al., *Blood Cells* 5(2):237-246, 1979; Saxe et al., *Exp. Hematol.* 12(4): 277-283, 1984; Stewart et al., *Blood* 81(10):2566-2571, 1993). The advantage of this strategy is that it caused low morbidity and mortality in the recipients; whereas a major disadvantage is that it requires large cell doses (Ramshaw et al., *Biol. Blood Marrow Transplant.* 1(2):74-80, 1995) and/or infusions over several days (Stewart et al., *Blood* 81(10): 2566-2571, 1993; Brecher et al., *Proc. Natl. Acad. Sci. USA* 79(16):5085-5087, 1982). On the other hand, successful engraftment with cells numbers as low as a single HSC has been documented in myeloablated recipients (Osawa et al., *Science* 273(5272):242-245, 1996; Krause et al., *Cell* 105(3): 369-377, 2001; Matsuzaki et al., *Immunity* 20(1):87-93, 2004), but this strategy exposes recipients to lethal doses of irradiation (which leads to significant host morbidity and mortality) and requires stringent maintenance of aseptic conditions (which is needed to minimize the infection in response to myeloablation). Mild or sublethal irradiation falls between these two extremes yielding engraftment with transplantation of intermediate numbers of cells and reduced morbidity and mortality (Mardiney et al., *Blood* 87(10:4049-4056, 1996; Stewart et al., *Blood* 91(10):3681-3687, 1998; James et al., *Blood* 96(4):1334-1341, 2000; Tomita et al., *Blood* 83(4): 939-948, 1994). However, the engraftment under these conditions is highly inconsistent. An alternative approach to myeloablation is to use genetically myelosuppressed recipient mice. Accordingly, murine strains resulting from deletions or mutations in the W locus can be used as recipients. The W locus encodes the c-kit gene (Nocka et al., *EMBO J.* 9:1805-1813, 1990; Reith et al., *Genes Dev.* 4:390-400, 1990). Mice with mutations in this gene are hematopoietic deficient (Geissler et al., *Genetics* 97:337-361, 1981; Geissler et al., *Exp. Hematol.* 11:452-460, 1983). The advantage of the w$^-$/w$^-$ recipient mice is avoidance of irradiation, but the disadvantage has been lower levels of engraftment than in preconditioned mice (Trevisan et al., *Blood* 88:4149-4158, 1996; Soper et al., *Exp. Hematol.* 27:1691-1704, 1999).

The present disclosure provides an improved murine HSC-based transplantation strategy that affords a consistent and high level of long-term engraftment. This transplation system provides a variety of desirable characteristics of previous strategies and at the same time minimizes their limitations. This system incorporates the following beneficial features. HSC enriched Sca-1$^+$ cells are used for transplantation donor cells because of their propensity of homing to bone (Plett et al., *Blood* 102:2285-2291, 2003). Donor mice are selected to be genetically or phenotypically distinguishable from the recipient mice.

For example, donor mice can be distinguished from recipient mice by the presence of a marker that is not present in the recipient. The marker can be a simple genetic difference, such as a nucleic acid polymorphism that does not result in a phenotypic difference, for example, a single nucleotide polymorphism (SNP) detectable by molecular analysis. Alternatively, the marker can yield a phenotypic difference, such as an optically detectable difference. Examples of optically detectable markers include proteins, such as green fluorescent proteins that confer a particular optical property (fluorescence) on a cell. Additionally, markers include proteins that indirectly confer such a property by enzymatically converting a substrate to a detectable product. Exemplary GFPs suitable as markers in the context of this disclosure include without limitation GFPs and variants described by Chalfie et al., *Science,* 263:802-805, 1994; Heim et al., *Proc. Natl. Acad. Sci. USA,* 91:12501-12504, 1994; Heim et al., *Nature,* 373:663-664, 1995; Peelle et al., *J. Protein Chem.,* 20:507-519, 2001; and Labas et al., *Proc. Natl. Acad. Sci. USA,* 99:4256-4261, 2002, and in U.S. Pat. Nos. 6,818,443; 6,800,733; 6,780,975; 6,780,974; 6,723,537; 6,265,548; 6,232,107; 5,976,796; and 5,804,387. Red fluorescent proteins are described in, e.g., U.S. Pat. No. 6,723,537. Such fluorescent proteins can be optically detected using, for example, flow cytometry. Flow cytometry for GFP is described in, e.g., Ropp et al., *Cytometry,* 21:309-317, 1995, and in U.S. Pat. No. 5,938,738. Other suitable detection methods include a variety of multiwell plate fluorescence detection devices, e.g., the CYTOFLUOR 4000® multiwell plate reader from Applied Biosciences. Other markers include proteins with enzymatic activities that convert a fluorogenic or chromogenic substrate into a fluorescent or visible product. Examples of such enzymatic markers include various naturally occurring and modified luciferases. Exemplary luciferases are described in U.S. Pat. Nos. 6,552,179; 6,436,682; 6,132,983; 6,451,549; 5,843,746 (biotinylated); U.S. Pat. No. 5,229,285 (thermostable), and U.S. Pat. No. 4,968,613. U.S. Pat. No. 5,976,796 describes a luciferase-GFP marker. Additional examples of markers with enzymatic activity include, e.g., chloramphenicol acetyltransferase (CAT), β-glucuronidase, β-galactosidase and alkaline phosphatase. Markers also include selectable markers, the activity of which can be detected as resistance or sensitivity to a selection agent, such as an antibiotic. Exemplary selectable markers include thymidine kinase, neomycin resistance, kanamycin resistance, and ampicillin resistance.

In one example, Sca-1$^+$ cells, isolated from green fluorescent protein (GFP)-expressing transgenic mice, are used as donor cells to distinguish donor cells from cells of host origin. The Sca-1$^+$ donor cells are injected into sublethally irradiated, genetically myelosuppressed W$^{41}$/W$^{41}$ recipient mice through retroorbital vein from 2 to 24 hours post-irradiation. Sublethally irradiated (e.g., 50-1000 cGy, such as about 500 cGy) W$^{41}$/W$^{41}$ recipient mice injected with Sca-1$^+$ cells transduced with a lentiviral vector expressing GFP showed long-term engraftment and GFP transgene expression in every recipient mouse. Thus, this system provides an improved murine HSC-based transplantation strategy that leads to consistent, robust, long-term engraftment with reduced morbidity and/or mortality.

Screening Methods

The mouse transplantation system described above provides a useful system for drug screening (e.g., in cell culture and animal models). The cellular and animal models are useful in methods for identifying agents that ameliorate the condition and/or that exert a favorable effect on bone metabolism, e.g., bone growth, bone maintenance, fracture repair, etc. In addition, such models are useful for evaluating potential gene therapies prior to their evaluation in human subjects.

For example, the methods of the present disclosure can be used to generate cells to evaluate expression of a transgene of interest (e.g., an osteogenic growth factor) and/or to determine whether administration of a polypeptide or protein produced using recombinant technology (such as an osteogenic growth factor) is effective for increasing bone growth. In addition, this transplantation model can be used to evaluate compounds or compositions that are members of a library of potential therapeutic agents. Test compounds selected from the library are administered to the cell or animal and the effect of the test compounds on bone growth, or an indicator associated with bone growth is evaluated. In the context of drug screening, indicators of bone growth include: a change in hematopoietic stem cell survival, a change in hematopoietic progenitor cell survival, a change in osteoblast lineage cell survival, a change in bone marrow engraftment by at least one of a hematopoietic stem cell, a hematopoietic progenitor cell, and an osteoblast lineage cell, a change in expression of one or more genes in at least one of a hematopoietic stem cell, a hematopoietic progenitor cell and an osteoblast lineage cell, a change in activity of one or more gene product in at least one of a hematopoietic stem cell, a hematopoietic progenitor cell, or an osteoblast lineage cell, a change in angiogenesis, a change in bone metabolism, a change in bone mass, and a change in bone density. Most typically, an increase in one or more of these indicators is measured or detected to identify and agent that increases bone growth and/or enhances bone repair.

The test compounds of the present disclosure can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckemann et al., *J. Med. Chem.* 37: 2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Nad. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33.2059, 1994; Carell et al., *Angew. Chem. Int. Ed. Engl.* 33:2061, 1994; and Gallop et al., *J. Med. Chem.* 37:1233, 1994.

Libraries of compounds can be presented in solution (e.g., Houghten, *Biotechniques* 13:412-421, 1992), or on beads (Lam, *Nature* 354:82-84, 1991), chips (Fodor, *Nature* 364: 555-556, 1993), bacteria or spores (U.S. Pat. No. 5,223,409), plasmids (Cull et al., *Proc. Nad. Acad. Sci. USA* 89:1865-1869, 1992) or on phage (Scott and Smith, *Science* 249:386-390, 1990; Devlin *Science* 249:404-406, 1990; Cwirla et al., *Proc. Natl. Acad. Sci. USA* 87:6378-6382, 1990; Felici, *J. Mol. Biol.* 222:301, 1991).

EXAMPLES

The following examples are provided to illustrate certain particular features and/or embodiments. These examples should not be construed to limit the invention to the particular features or embodiments described. Each of the publications cited herein is incorporated by reference in its entirety.

Example 1

Cloning and Analysis of a Secretable FGF-2 Analog

Materials and Methods

Human FGF-2 Expression Plasmids.

The full-length human FGF-2 cDNA was cloned by PCR amplification using purified RNA of normal human skin fibroblasts as the template. Briefly, sense and antisense primers were designed to contain the entire open reading frame: sense primer: 5'-gcg cgc aag ctt G*TG GCA GCC GGG AGC ATC AC-3' (SEQ ID NO:7); antisense primer: 5'-gcg gct gac GGC CAT TAA AAT CAG CTC TT-3' (SEQ ID NO:8). HindIII and SalI restriction sites (underlined) were added to the sense and antisense primer, respectively, to facilitate its cloning into pFLAGCMV-1 cloning vector. The sense primer contains the first 6 codons of the human FGF-2 gene with the start codon for methionine (ATG) mutated to valine (GTG). This mutation was introduced so that a secretion signal sequence could be added later. The antisense primer corresponds to the 3'-end of the open reading frame, including the termination codon. A single band of a 500-bp PCR product was obtained and its identity was confirmed by restriction mappings. The PCR product containing the full length human FGF-2 cDNA was then digested with HindIII/SalI, purified, and subcloned into the pFLAGCMV-1 cloning plasmid (Eastman Kodak, Rochester, N.Y.) to produce the pFC-FGF-2 plasmid vector. To enhance FGF-2 translation, an optimized Kozak sequence (gcccaccatgg) was later added to the full length human FGF-2 cDNA. The 27 nucleotide sequence corresponding to 5'-UTR region and a PstI restriction site were also added to the 5' end to facilitate subsequent cloning into the VR1012 cloning vector. This was also accomplished by PCR amplification using the following sense primer: 5'-aaa ctg cag GGG ATC CCG GCC GGG CCC CGC AGG ATG GCA GCC GGG AGC ATC AC-3' (SEQ ID NO:9) and antisense primer: 5'-gcg gct gac GGC CAT TAA AAT CAG CTC TT-3' (SEQ ID NO:10). The purified PCR product was digested with PstI and SalI restriction enzymes and subcloned into PstI/SalI-digested VR1012 expression vector to generate the FGF-2 plasmid vector, VR1012-bFGF.

MLV-based FGF-2 expression vectors. To produce an MLV-based FGF-2 vector, pY-FGF, the FGF-2 gene from VR1012-bFGF was excised by NotI and XhoI digestion, blunt-ended, and subcloned into BamHI-cleaved and blunt-ended MLV-based retroviral expression vector as described previously (Peng et al., *Mol. Therapy.* 4:95-104; 2001). To add the BMP2/4 secretion signal sequence, the secretion signal sequence of the BMP2/4 hybrid gene (Hammonds et al., *Mol. Endocrinol.* 5:149-155, 1991) was subcloned into the 5' end of the FGF-2 gene to produce the pY-BMP-FGF vector as described previously (Peng et al., *Mol. Therapy* 4:95-104; 2001). The exemplary FGF-2 analog is schematically illustrated in FIG. 1A. The start codon for methionine was removed during the insertion of the BMP2/4 signal sequence. The amino acid sequence of the BMP-FGF junction area was shown in FIG. 1B.

PCR-Based Site-Directed Mutagenesis.

The QuickChange site-directed mutagenesis kit from Stratagene (La Jolla, Calif.) was used to generate mutations on cys-70 (C2) and/or cys-88 (C3) of FGF-2. Briefly, five pairs of complementary primers were synthesized: the first pair was used for the C2S mutation, the second pair for the C3S mutation, the third pair for the C3N mutation, and the fourth and fifth pair is for the C2A mutation and C3A mutation, respectively (Table 2). The sequences of the primer sets are shown in Table 2. For C2S mutation, the cys-70 codon (TGT) was mutated to a serine codon (TCT). For the C3S mutation, the cys-88 codon (TGT) was mutated to a serine codon (TCT). For the C3N mutation, the cys-88 codon was mutated to an asparagine codon (TCT). For C2A mutation, the cys-70 codon (TGT) was mutated to an alanine (GCT). For the C3S mutation, the cys-88 codon (TGT) was mutated to a serine codon (GCT).

The PCR-based, site-directed mutagenesis procedure was carried out according to the recommendation of the vendor, using the pY-FGF or pY-BMPFGF parental plasmids as the template. For double mutations, the mutation at the C2 and C3 was introduced sequentially. The resulting products were confirmed by DNA sequencing.

MLV-Based Vector Production.

The VSV-G pseudotyped MLV-based vectors were generated by transient transfection in 293T cells as described previously (Peng et al., *Mol. Therapy.* 4:95-104; 2001). Briefly, a 10-cm plate of 293T cells were transfected with a mixture of 20 μg of retroviral expression vector (e.g., pY-FGF or its derivatives), 10 μg of MLV-GP expression vector and 1 μg of VSV-G expression vector by $CaPO_4$ precipitation. The conditioned medium (CM) containing viral vectors was collected and concentrated by ultracentrifugation 48 hrs after the transfection. The viral titer was determined by the end-point dilution assay for the marker gene (e.g., β-gal) expression or by real-time PCR assay for FGF-2 transgene expression in transduced HT1080 cells.

until assay. The cell layers were lysed with 500 μl of 1× Reporter lysis buffer (Promega, Madison, Wis.), and the cell lysates were kept frozen until assay. The amount of FGF proteins in cell lysates and CMs was determined with an ELISA kit (R&D systems, Minneapolis, Minn.), according to the manufacturer's instruction. The amount of FGF-2 protein was normalized to ng of FGF-2 per $10^6$ cells.

The identity of FGF-2 proteins in CMs and cell lysates was also determined with Western immunoblot assays. Briefly, the CM and lysate proteins of HT1080 cells 24-hr after transduction with an MLV-based vector expressing FGF-2 or an analog thereof were resolved on a 8% or 15% SDS-PAGE and transblotted onto PVDF membranes (Bio-Rad Labs., Hercules, Calif.). Known amounts of recombinant human FGF-2 standard (Sigma, St. Louis, Mo.) were included in each blot for comparison. To identify FGF-2 bands, the blots were incubated with a mouse anti-human FGF-2 monoclonal antibody (UpState Biotech., Lake Placid, N.Y.) and FGF-2 bands were visualized with the goat-anti-mouse IgG antibody conjugated with horse radish peroxidase (Pierce, Rockford, Ill.) followed by the chemiluminescent assay (Pierce).

Deglycosylation of CM FGF-2.

Deglycosylation was performed with enzymes provided by the Enzymatic deglycosylation kit (Prozyme, San Leandro, Calif.) that contains PNGase F (which hydrolyzes core oligosaccharides of N-linked glycosylated proteins), endo-O-glycosidase (which hydrolyzes core oligosaccharides of O-linked glycosylated proteins, only after substitutions on the core oligosaccharide, such as sialic acid, galactose, fucose or N-acetylglucosamine, are removed with the appropriate

TABLE 2

Primers for PCR-based site-directed mutation of two cysteine residues of human FGF-2.

| Mutation | Primer | Sequence* |
|---|---|---|
| C2S mutation | Sense Antisense | 5'-TCTATCAAAGGAGTG<u>TCT</u>GCTAACCGTTACCTG-3' SEQ ID NO: 11 5'-CGAGTAACGGTTAGC<u>AGA</u>CACTCCTTTGATAGA-3' SEQ ID NO: 12 |
| C3S mutation | Sense Antisense | 5'-TTACTGGCTTCTAAA<u>TCT</u>GTTACGGATGAGTGT-3' SEQ ID NO: 13 5'-ACACTCATCCGTAAC<u>AGA</u>TTTAGAAGCCAGTAA-3' SEQ ID NO: 14 |
| C3N mutation | Sense Antisense | 5'-TTACTGGCTTCTAAA<u>AAT</u>GTTACGGATGAGTGT-3' SEQ ID NO: 15 5'-ACACTCATCCGTAAC<u>ATT</u>TTTAGAAGCCAGTAA-3' SEQ ID NO: 16 |
| C2A mutation | Sense Antisense | 5'-TCTATCAAAGGAGTG<u>GCT</u>GCTAACCGTTACCTG-3' SEQ ID NO: 17 5'-CGAGTAACGGTTAGC<u>CGA</u>CACTCCTTTGATAGA-3' SEQ ID NO: 18 |
| C3A mutation | Sense Antisense | 5'-TTACTGGCTTCTAAA<u>GCT</u>GTTACGGATGAGTGT-3' SEQ ID NO: 19 5'-ACACTCATCCGTAAC<u>CGA</u>TTTAGAAGCCAGTAA-3' SEQ ID NO: 20 |

*The underline codon indicates the site of the mutation.

Determination of the Amounts of FGF-2 Protein in Lysates or in CM.

Briefly, HT1080 cells or primary rat skin fibroblasts (RSF) in 6-well plates were transduced with the test MLV-based vectors expressing wild-type or C2- and/or C3-mutated FGF-2 genes or BMP2/4-FGF-2 hybrid genes.

Following transduction, the cells were cultured in fresh medium prior to collection of conditioned media (CM) and/or cell lysates. The CMs were collected and frozen immediately exoglycosidase, such as sialidases), sialidase A (which removes sialic acid-containing substitutions from core oligosaccharides), and the combination of the three glycosidases. Each glycosidase digestion reaction was carried out as recommended by the manufacturer. Briefly, the CMs were collected from the transduced cells, and 30 μl of each CM was mixed with 10 μl of 5× incubation buffer and 2.5 μl of denaturation solution. The samples were heated to 100° C. for 5 minutes, followed by the addition of 2.5 μl of detergent solution. The PNGase, sialidase A, or endo-O-glycosidase (1 µl each), separately or all together, was added to the denatured CM protein samples. The samples were then incubated overnight at 37° C., and the FGF-2 proteins were then identified by Western analysis as described above.

Determination of Biological Activity of FGF-2 and Cysteine-Mutated Variants.

The in vitro biological activity of recombinant C2S/C3N-mutated FGF-2 was determined by measuring its ability to stimulate [3H]thymidine incorporation in quiescent foreskin fibroblasts similar to a previously described assay (Kasperk et Results Effects of Cys-70 and/or Cys-88 Mutations on FGF-2 Secretion in HT1080 Cells.

To evaluate whether C2 and/or C3 mutations improve FGF-2 protein secretion, HT1080 cells, which do not express detectable amounts of FGF-2 protein, were transduced with MLV-based vectors expressing wild-type or the cysteine-mutated FGF-2 gene. Table 3 shows the amounts of FGF-2 protein in the cell lysate and CM of the transduced cells 48-hr post-transduction.

TABLE 3

Effects of cys-70 (C2) and cys-80 (C3) mutations on FGF-2 production and secretion in HT1080 cells (mean ± S.D., n = 2).[a]

| Vector-treated cells | FGF-2 in CM | FGF-2 in lysate | Total FGF-2[b] | % Secretion[c] |
|---|---|---|---|---|
| pY-FGF | 16.2 ± 3.2[d] | 148.2 ± 39.5 | 164.4 ± 39.6 | 9.8 ± 3.2 |
| pY-FGFC2S | 47.4 ± 9.3 | 497.6 ± 22.3 | 545.0 ± 24.2** | 8.7 ± 1.8 |
| pY-FGFC3S | 99.4 ± 15.8 | 532.2 ± 69.4 | 631.6 ± 71.2* | 15.7 ± 3.2 |
| pY-FGFC3N | 120.6 ± 4.0 | 503.6 ± 111.6 | 624.2 ± 111.7* | 19.3 ± 4.3 |
| pY-FGFC2SC3S | 135.6 ± 9.0 | 843.2 ± 111.2 | 978.8 ± 111.6* | 13.9 ± 2.1 |
| pY-FGFC2SC3N | 129.4 ± 35.4 | 613.2 ± 2.6 | 742.6 ± 35.5** | 17.4 ± 4.8 |

[a]There is no detectable FGF-2 protein in CM or lysate in untreated or pY-β-gal-treated HT-1080 cells.
[b]Total FGF-2 is the sum of FGF-2 in CM and FGF-2 in lysate. *$p < 0.05$, **$p < 0.01$, compared with the pY-FGF-treated cells.
[c]% FGF-2 secretion was calculated by dividing FGF-2 in CM by total FGF-2. None of the cysteine-mutated vector-treated cells was significantly different from the pY-FGF-treated cells.
[d]ng/$10^6$ cells per 48 hrs.

al., *Growth Factors* 3:147-158, 1990). Briefly, human foreskin fibroblasts were plated at a density of 5,000 cells per well in 24-wells plates in serum-free DMEM for 24 hrs. Cell medium was changed to fresh serum-free DMEM for an additional 24-hrs. Various amounts of the recombinant human FGF-2 protein standard and the CM FGF-2 protein of the pY-BMPFGFC2SC3N-transduced cells were then added to each well of skin fibroblasts for an additional 24 hrs. The amount of FGF-2 protein of each CM was pre-determined by an ELISA as described above prior to the bioactivity assay. [3H]Thymidine (1.5 µCi/well) was added during the final 6 hrs of the incubation. The incorporation of [3H]thymidine into trichloroacetic acid-precipitable DNA was measured in replicate wells (n=6 per each group) by liquid scintillation counting. To confirm that the mitogenic activity was due to the FGF-2 protein in the CM, the CM was also pretreated with 5 µg/ml of an anti-FGF-2 antibody for an hour at 37° C. (to adsorb away the CM FGF-2 protein) prior to the mitogenic activity assay.

The in vivo biological activity of recombinant wild-type FGF-2 and the recombinant C2S/C3N-FGF-2 mutant was determined in a subcutaneous skin implant rat model. Briefly, primary skin fibroblasts from inbred strain of Fisher 344 rats were transduced three times with each test MLV vector. The transduction level was determined with the β-gal marker gene expression or FGF-2 expression and also by real-time PCR assay for FGF-2 mRNA expression. Greater than 75% of transduction efficiency has routinely been obtained. Four million each of transduced primary rat skin fibroblasts (RSF) expressing β-gal marker gene, wild-type FGF-2 gene, or C2S/C3N-FGF-2 mutant gene were incubated in a 1-cm×1-cm Gelfoam disc (Pharmacia & Upjohn, Kalamazoo, Mich.) overnight as previously described (Gysin et al., *Gene Therapy* 9:991-999, 2002). Each disc was implanted into a subcutaneous pocket at the back of a Fisher 344 rat. Fourteen days later, the serum level of FGF-2 was determined with the ELISA assay and the weight of each implant was determined.

Consistent with the premise that the secretion of unmodified FGF-2 in mammalian cells is inefficient, the amount of FGF-2 in the CM of the wild-type FGF-transduced cells (pY-FGF) represented ~10% of the total FGF-2 protein produced. Mutation of C2 or C3 to serine or asparagine alone significantly increased the amounts of FGF-2 in both cell lysates and CMs by 2- to 3-fold. However, the FGF-2 secretion was enhanced by 40-100% in cells transduced with vectors containing the C3 mutation (C3S and C3N), but not those with the C2S mutation. Double mutations of C2 and C3 increased the total amounts of FGF-2 about pY-FGF-transduced cells but did not further enhance FGF-2 secretion compared to the C3 single mutation. Western immunoblot analysis showed that: a) each group of transduced cells produced a major immunoreactive band of 21-kd, that co-migrated with the FGF-2 protein standard, in both cell lysates and CMs, and b) the amounts of FGF-2 protein in both lysates and CMs were significantly higher in cells transduced with the cysteine-mutated FGF-2 vectors than in cells transduced with the wild-type pY-FGF vector. Cells transduced with the control pY-LMPHA vector, as expected, produced no detectable amounts of FGF-2 protein in cell lysates or in CMs.

Effects of the Addition of BMP2/4 Secretion Signal Sequence and C2 and/or C3 Mutation on FGF-2 Secretion in HT1080 Cells.

Table 4 shows that the addition of the BMP2/4 hybrid secretion signal sequence alone (pY-BMPFGF) resulted in a sevenfold reduction in total amounts FGF-2 compared to the pY-FGF-transduced cells. However, the relative amount of FGF-2 protein in the CMs of the pY-BMPFGF-treated cells accounted for 54.2% of the total FGF-2 proteins produced, which was >5-fold more than that in the CMs of the pY-FGF-treated cells (9.8%). This indicated that the BMP2/4 signal sequence significantly enhanced the secretion of FGF-2 in HT1080 cells. The single C2S mutation along with the BMP2/4 secretion signal sequence (pY-BMPFGFC2S) did not increase total amount or secretion of the FGF-2 protein compared to the pY-BMPFGF-transduced cells. In contrast, double mutation of C2 and C3 markedly and significantly increased total amount of FGF-2 protein in CMs and in lysates compared to the pY-BMPFGF group. The enhancement in the total FGF-2 produced appeared to be larger in C3N mutated group compared to that in C3S mutated group: C3S mutation yielded a ~3-fold increase; while C3N mutation produced a 7-fold enhancement. The increase in the amounts of FGF-2 in CMs are also higher in cells transduced with vectors containing the C3N mutation than in cells treated with vectors containing the C3S mutation. With respect to FGF-2 secretion, the cells treated with the C2/C3 double mutated vectors showed an increase in FGF-2 secretion by ~40-fold compared with pY-BMPFGF-treated cells.

TABLE 4

Effects of the addition of BMP2/4 secretion signal sequence and C2/C3 mutations on FGF-2 production and secretion in HT1080 cells (mean ± SD, n = 2).

| Vector-treated cells | FGF-2 in CM | FGF-2 in lysate[d] | Total FGF-2[a] | % Secretion[b] |
|---|---|---|---|---|
| pY-FGF | 16.2 ± 3.2[c] | 148.2 ± 39.5 | 164.4 ± 39.6 | 9.8 ± 3.2 |
| pY-BMPFGF | 13.0 ± 1.0 | 11.0 ± 0.3 | 24.0 ± 1.0* | 54.2 ± 4.4** |
| pY-BMPFGFC2S | 15.6 ± 0.4 | 16.2 ± 3.1 | 31.8 ± 3.1* | 49.1 ± 9.5* |
| pY-BMPFGFC2SC3S | 318.8 ± 5.1 | 153.2 ± 0.7 | 472.0 ± 5.1** | 67.5 ± 1.1*** |
| pY-BMPFGFC2SC3N | 916.2 ± 203.1 | 155.4 ± 31.8 | 1071.6 ± 205.6* | 85.5 ± 25.8* |

[a]Total FGF-2 is the sum of FGF-2 in CM and FGF-2 in lysate. *p < 0.05, and **p < 0.01, compared with the pY-FGF-treated cells.
[b]% FGF-2 secretion was calculated by dividing FGF-2 in CM by total FGF-2. *p < 0.05, p < 0.01, and *p < 0.001, compared with the pY-FGF-treated cells.
[c]ng/10^6 cells per 48 hrs.
[d]ng/10^6 cells.

Table 5 summarizes the effect of C2 and C3 mutations of FGF-2 production in rat skin fibroblasts.

TABLE 5

Comparison of cys-70 (C2) and cys-80 (C3) mutations on FGF-2 secretion in normal rat skin fibroblasts.[a]

| Vector-treated cells | FGF-2 in CM (pg/10^6 cells) |
|---|---|
| pY-β-gal control | 2.8 |
| pY-FGF | 15.8 |
| pY-BMPFGF | 35.3 |
| pY-BMPFGFC3A | 3,641.6 |
| pY-BMPFGFC2AC3A | 2,586.5 |
| pY-BMPFGFC2A | 759.2 |
| pY-BMPFGFC2AC3N | 18,674.2 |
| pY-BMPFGFC2SC3S | 3,255.2 |
| pY-BMPFGFC2SC3N | 8,480.6 | pY's denotes the MLV-based vectors;
pY-BMP's means the BMP2/4 secretion signal sequence has been added to the transgene to improve secretion;
C2A = cys-70 to alanine mutation,
C2S = cys-70 to serine mutation,
C3A = cys-88 to alanine mutation;
C3S = cys-88 to serine mutation; and
C3N = cys-88 to asparagine mutation.

Rat skin fibroblasts secreted very low basal level of FGF-2 (2.8 pg/10^6 cells/24 hrs). Rat skin fibroblasts transduced with wild-type pY-FGF vector also secreted very low level of FGF-2 (15.8 pg/10^6 cells/24 hrs). Addition of the BMP2/4 secretion signal only increased the amount of FGF-2 in CM by ~3-fold. Modification of cys-70 (C2) and cys-88 (C3) drastically increased FGF-2 secretion in rat fibroblasts. Modification of cys-70 to alanine increased secretion at least 2-fold more than the cys-70 to serine mutation.

Western immunoblot of FGF-2 immunoreactive protein bands in lysates and CMs of HT1080 cells transduced with pY-BMPFGF vectors showed an additional immunoreactive band of ~26 kD, in addition to the 21-kD immunoreactive protein band that co-migrated with the FGF-2 protein standard in lysates of cells transduced with the C2S vector and/or the C3S vector (but not the non-cysteine-mutated vectors). Lysates of cells transduced with the C2SC3N vector showed yet another immunoreactive band of ~29 kD. Because CMs of cells transduced with vectors that did not have the C3 mutation contained relatively low levels of FGF-2 protein (Table 4) and because only a small amount of CM (10 µl) was analyzed by Western immunoblots, only CMs of cells transduced with vectors containing the C3 mutation showed detectable FGF-2 immunoreactive bands. Because serine and asparagine are potential sites of O- and N-glycosylation, respectively, it is possible that the larger immunoreactive bands are glycosylated forms of FGF-2 and that the 26-kD band is O-glycosylated FGF-2 and the 29-kD band is both O- and N-glycosylated.

Effects of the Addition of BMP2/4 Signal Sequence and C2 and C3 Double Mutations on FGF-2 Secretion in Rat Skin Fibroblasts.

The ability of the BMP2/4 signal sequence in combination with C2S and C3N double mutation to increase the stability and secretion of FGF-2 protein in normal, untransformed cells was evaluated. Primary rat skin fibroblasts (RSF) were transduced with the pY-β-galactosidase (pY-β-gal) [control vector], the wild-type pY-FGF, or the cysteine-mutated pY-BMP-FGF-C2SC3N vector. Staining for β-gal expression with x-gal in pY-β-gal-transduced cells indicated that the transduction efficiency was >90%. Table 6 summarizes the amounts of FGF-2 protein in CM and in lysate of RSF 48-hr post-transduction. Both CM and lysates of RSF transduced with pY-β-gal showed very low (almost undetectable) levels of FGF-2 protein. Transduction of RSF with the pY-FGF vector markedly increased the FGF-2 protein level in the lysate, but the amount of FGF-2 protein in CM was still very low, only accounting for ~1% of the total FGF-2 produced. As in HT1080 cells, the addition of the BMP2/4 secretion signal inhibited FGF-2 biosynthesis in RSF, as the total FGF-2 protein synthesized by RSF transduced with the pY-BMPFGFC2SC3N vector were reduced by ~60% compared to that the pY-FGF-treated cells. This reduction was not due to a reduced number of copies of inserted gene as determined by real-time PCR analysis on genomic DNA. The large majority of the FGF-2 protein (~90%) in the pY-BMPFGFC2SC3N-transduced cells was in CMs, indicating that the inclusion of BMP2/4 signal sequence also led to a drastic increase in FGF-2 secretion in untransformed, RSF. More importantly, despite the ~60% reduction in the total amounts of FGF-2 produced, the actual amounts of FGF-2 in the CMs of the pY-BMPFGFC2SC3N-transduced RSF were 37-fold higher than those in CMs of the pY-FGF-transduced cells.

TABLE 6

Effects of the test modification of FGF-2 gene on FGF-2 production and secretion in primary rat skin fibroblasts.

| Vector-treated cells | FGF-2 in CM | FGF-2 in lysate[d] | Total FGF-2[a] | % Secretion[b] |
|---|---|---|---|---|
| pY-β-gal | 0.00 ± 0.00[c] | 0.52 ± 0.02 | 0.52 ± 0.02 | 0.48 ± 0.09 |
| pY-FGF | 0.88 ± 0.01 | 91.7 ± 0.0 | 92.6 ± 0.0 | 0.95 ± 0.10 |
| pY-BMPFGFC2SC3N | 33.0 ± 0.4 | 4.8 ± 0.5 | 37.9 ± 0.6* | 87.3 ± 1.7* |

[a]Total FGF-2 is the sum of FGF-2 in CM and FGF-2 in lysate. *p < 0.05, and **p < 0.01, compared with the pY-FGF-treated cells.
[b]% FGF-2 secretion was calculated by dividing FGF-2 in CM by total FGF-2. *p < 0.001, compared with the pY-FGF-treated cells.
[c]ng/10[6] cells per 48 hrs.
[d]ng/10[6] cells.

FGF-2 proteins in CMs of three preparations of pY-BMPFGFC2SC3N-transduced RSF were compared to those in CM of a preparation of pY-BMPFGFC2SC3N-transduced HT1080 cells by western immunoblot. In contrast to HT1080 cells which produced the major 26-kD and 29-kD immunoreactive bands, the CM from each of the three pY-BMP-FGF-C2SC3N-transduced RSF preparations contained a major 27-kD immunoreactive protein band and a very minor 29-kD band, in addition to the 21-kD FGF-2 band. The production of this 27-kD band was not unique to primary RSF, since the transduced primary rat marrow stromal cells also yielded this major 27-kD band. Thus, the glycosylation of the cysteine-mutated FGF-2 proteins appears to be different between primary cells and transformed cells.

To confirm that the 26-kD and 29-kD immunoreactive bands in HT-1080 cells and the 27-kD band in RSF were indeed glycosylated species of FGF-2, the CM of pY-BMP-FGF-C2SC2N-treated HT1080 cells and also the CM of pY-BMP-FGF-C2SC2N-treated RSF were treated with PNGase F, endo-O-glycosidase, sialidase A, or all three glycosidases. With the HT1080 CM, combination treatment with all three glycosidases converted both the 26-kD and 29-kD bands to the 21-kD non-glycosylated FGF-2, indicating that both bands are glycosylated species of FGF-2. Sialidase A alone converted both the 26-kD and 29-kD bands to a band of an apparent size between 21-kD and 26-kD. The PNGase F treatment alone converted the 29-kD to a major band of slightly greater than 26-kD, in addition to the 21-kD non-glycosylated FGF-2. The endo-O-glycosidase treatment alone (without sialidase A) had no significant effects on either the 29-kD or 26-kD band, suggesting that the O-linked core oligosaccharide had sialic acid-containing substitutions. With respect to the 27-kD band in RSF CM, the combination treatment also converted the 27-kD band to 21-kD non-glycosylated FGF-2 band, confirming that it is a glycosylation form of FGF-2. However, the PNGase F treatment, but not endo-O-glycosidase or sialidase A treatments, converted the 27-kD band to the 21-kD non-glycosylated FGF-2, suggesting that the 27-kD band is primarily an N-linked glycosylated FGF-2.

Effects of Glycosylation on the Biological Activity of Glycosylated FGF-2 Chimeric Protein.

The pY-BMPFGFC2SC3N-transduced RSF displayed an altered morphology compared to pY-β-gal-transduced RSF. Primary rat skin fibroblasts were transduced with either pY-β-gal control vector or the pY-BMPFGFC2SC3N vector. One week after the transduction, the cells were stained with Fast Red. The cells transduced with the pY-BMPFGFC2SC3N vector were much smaller than the pY-β-gal-transduced control cells. They were also changed to spindle-like shape from the elongated shape that is typical of fibroblasts. This morphology was similar to that of primary RSF after treatment with FGF-2 for an extended period of time, e.g., 1 week. No such morphological change was seen in the pY-FGF-transduced RSF. The change in cell morphology in pY-BMPFGFC2SC3N-treated RSF, which secreted large amounts of glycosylated FGF-2 into CMs, strongly suggests that the secreted glycosylated FGF-2 is functionally active.

The ability of the modified FGF2* and the wild type, un-modified FGF2, to promote the proliferation of marrow stromal cells and to stimulate the phosphorylation and activation of the extracellular regulated protein kinases-1/2 (Erk1/2) was also compared in vitro in the cell proliferation assay. There were no significant differences between the modified FGF2 and the unmodified WT FGF-2 in their ability to stimulate cell proliferation and Erk1/2 activation.

To confirm that the glycosylation did not adversely affect the biological activity of FGF-2 in vitro, the ability of the CM of the pY-BMPFGFC2SC3N-treated cells to stimulate [$^3$H] thymidine incorporation in quiescent human primary foreskin fibroblasts was compared with that of the commercial, recombinant non-glycosylated FGF-2. The dose-dependent stimulation curve of the CM FGF-2 of transduced HT1080 cells was similar to that of the recombinant non-glycosylated FGF-2, demonstrating that glycosylation did not significantly affect the biological activity of FGF-2. More importantly, the pretreatment of the CMs of pY-BMPFGFC2SC3N-treated cells with an anti-FGF-2 antibody almost completely eliminated the mitogenic activity of the CM, indicating that the mitogenic activity of the CM was due largely to FGF-2.

Biological Effects of Subcutaneous Implantation of pY-BMPFGFC2SC3N-Transduced Rat Skin Fibroblasts in Syngenic Rats.

To initiate an evaluation of the utility of the pY-BMPFGFC2SC3N vector in gene transfer protocols, subcutaneous implantation of RSF transduced with the pY-BMPFGFC2SC3N vector into the dorsal back of syngenic rats was evaluated, and the ability of such transplants to increase serum FGF-2 levels and enhance growth of the implant was determined. A Gel-foam square (1 cm$^2$) was impregnated with 4 million of primary rat skin fibroblasts transduced with pY-β-gal, pY-FGF control vector, or pY-BMPFGFC2SC3N vector overnight and was implanted subcutaneously into the dorsal back of a syngenic rat. Fourteen days after the implantation, animals were sacrificed and serum FGF-2 was determined by an ELISA assay (FIG. 2). The implants were dissected, weighed and evaluated morphologically.

The serum FGF-2 level in rats with implants containing the control pY-β-gal-transduced RSF or pY-FGF-transduced RSF were very low (<10 ng/ml). By contrast, every rat that had the implant containing the pY-BMPFGFC2SC3N-transduced RSF showed very high serum FGF-2 levels (~150 ng/ml). The weight of implants was significantly greater (2- to 3-fold) in the pY-BMPFGFC2SC3N group than that in the pY-β-gal or in the pY-FGF control groups at fourteen days. Gross anatomical examination of the implants showed that the pY-BMPFGFC2SC3N implants, but not the pY-β-gal or pY-FGF implants, were reddish in color and rich in blood, demonstrating that extensive vascularization had occurred.

The results described above demonstrate that efficient and consistent secretion of FGF-2 from mammalian cells can be achieved by adding to the FGF-2 transgene a potent secretion signal sequence, such as the BMP2/4 hybrid signal sequence, and also by mutation of cys-70 (C2) and cys-88 (C3) to a serine or an asparagine. These modifications together have led to an overall ~60-fold and ~40-fold increase in the actual amounts of FGF-2 protein secreted into the CMs of transduced HT1080 cells and primary RSF, respectively, compared to the unmodified FGF-2 gene. More importantly, the ex vivo application of the modified FGF-2 MLV-based expression vector, but not the wild-type unmodified FGF-2 vector, in a subcutaneous transplant rat model resulted in a ~200-fold increase in serum FGF-2. In addition, it also led to a ~3-fold increase in the growth weight and the apparent vascularization of the implants. These findings indicate that the secretion and stability can be greatly enhanced by modifying wild type FGF-2 (for example, by the inclusion of a strong secretion signal, such as the BMP2/4 secretion signal, and the by stabilizing the product, e.g., by the introduction of C2/C3 mutations). Furthermore, these results show that a vector incorporating modified FGF-2 can be used to produce consistent, therapeutic levels of FGF-2.

Because the C2/C3-mutated FGF-2 expression vectors have the same viral backbone as the wild type unmodified FGF-2 expression vector, and because the viral titers and transduction efficiency (determined by real-time PCR analysis of FGF-2 mRNA transcripts levels) of the C2/C3-mutated FGF-2 expression vectors in these studies were very similar to those of the unmodified FGF-2 vector, the increased amounts of FGF-2 proteins in cells transduced with the C2/C3-mutated vectors were not due to an increase in gene expression and/or protein biosynthesis. Thus, the observed increase in total FGF-2 proteins in cells transduced with the C2/C3-mutated FGF-2 vectors is due to an enhanced stability (and/or decreased degradation) of the recombinant FGF-2 protein. This conclusion is consistent with the previous studies in COS-7 cells, which showed that the mutation of C2/C3 of human FGF-2 gene leads to an increase in the stability of the recombinant FGF-2 protein (Sasada et al., *Ann. N.Y. Acad. Sci.* 638:149-160, 1991; Seno et al., *Biochem. Biophys. Res. Commun.* 151:701-708, 1988). Without being bound by theory, it is likely that, in addition to preventing the oxidation of key cysteines and/or intra- and/or inter-molecular disulfide formation, which have been shown to adversely affect FGF-2 stability (Iwane et al., *Biocehm. Biophys. Res. Commun.* 146: 470-477, 1987), glycosylation of the introduced serine or asparagine residues plays an important role in the stabilization of the recombinant FGF-2 protein. This conclusion is supported by two observations. Firstly, the enhancement in FGF-2 stability in the CMs of HT1080 cells transduced with C2/C3-mutated vectors without the BMP2/4 signal sequence was only ~7-fold, while the increase in FGF-2 stability in cells transduced with the BMP2/4 signal sequence containing C2/C3-mutated vectors was ~60-fold. Secondly, the FGF-2 protein produced by HT1080 cells transduced with the C2/C3-mutated vectors without the BMP2/4 secretion signal sequence was largely non-glycosylated, whereas the FGF-2 protein produced by cells transduced with the C2/C3-mutated vectors with the BMP2/4 signal sequence was primarily glycosylated. In combination, these results indicate that glycosylation of the mutated FGF-2 protein plays an important role in enhancing production the FGF-2 recombinant protein.

The recombinant FGF-2 protein produced by cells transduced with the cysteine-mutated FGF-2 vectors were glycosylated only if BMP2/4 secretion signal sequence was included in the construct. The BMP2/4 secretion signal sequence is a member of the large family of cleavable classical signal sequences (Hammonds et al., *Mol. Endocrinol.* 5:149-155, 1991) that direct the secretory proteins to the ER and the golgi for processing, including glycosylation, and secretion (Brodsky, *Int. Rev. Cytol.* 178:277-328, 1998). Thus, the BMP2/4 signal sequence redirected the FGF-2 chimera to the ER/golgi for secretion. The glycosylation of the cysteine-mutated FGF-2 most likely took place within the ER/golgi, where glycosidases and glycosyltransferases are located (Verbert et al., *Biochim. Biophys. Acta* 1473:137-146, 1999). These conclusions are consistent with previous findings that the addition of the growth hormone secretion signal (another member of the cleavable classical signal sequences) to the FGF-2 gene also appeared to result in the secretion of glycosylated FGF-2 proteins (Blam et al., *Oncogene* 3:129-136, 1988).

Enhancement in FGF-2 stability was achieved by introducing a mutation at the C3 site, in that the C3S mutation yielded a ~3-fold enhancement, and the C3N mutation produced a ~6-fold increase. Although the mutation of C2 and C3 (e.g., to an amino acid that can be glycosylated, such as a serine or an asparagine) appears to have an impact on the stability (or degradation) of the FGF-2 recombinant protein, the C3 mutation has an enhancing effect (>2-fold) on the secretion of the recombinant FGF-2 protein even without the BMP2/4 sequence signal.

The FGF-2 chimeric protein produced by cells transduced with the modified FGF-2 expression vector is biologically active. The transduced cells stimulated the proliferation of quiescent human skin fibroblasts to an extent similar to that induced by recombinant FGF-2 protein. Pre-incubation of the CMs with an anti-FGF-2 antibody completely abolished the ability of the CMs to stimulate the proliferation of quiescent skin fibroblasts. Hence, the mitogenic activity in the CMs of the transduced cells was due to the FGF-2 protein and not other growth factors. In addition, the morphology of the cells transduced with the modified FGF-2, but not that of cells transduced with control vectors, was highly proliferative, as is expected with biologically active FGF-2. The ex vivo administration of cells transduced with the modified FGF-2 vector also promoted the growth and vascularization of the implants to provide further evidence that the FGF-2 protein produced by the modified expression vector is biologically active in vivo.

Example 2

An Improved Mouse Sca-1+ Cell-Based Bone Marrow Transplantation Model

Materials and Methods

Animals.

The TgN β-actin-EGFP (TgN-GFP) donor mice, wild-type C57BL/6J mice and C57BL/6J-$W^{41}/W^{41}$ ($W^{41}/W^{41}$) mice were used to produce an improved mouse bone marrow transplantation model.

Sca-1+ Cell Enrichment.

Whole bone marrow (WBM) cells were harvested from TgN-GFP mice by flushing tibiae and femurs with phosphate-buffered saline (PBS) using a 26-g needle and syringe. Erythrocytes were removed by osmotic lysis using a solution of 155 mM $NH_4Cl$, 10 mM $KHCO_3$ and 110 μM $Na_2EDTA$, followed by rinsing with PBS. The cell preparation was then incubated with magnetic microbeads conjugated with antibody specific for Sca-1 and applied twice to an automated magnetic separation column (AutoMacs™) according to manufacturer instructions (Miltenyi Biotec, Inc, Auburn, Calif.). Cell yields of aliquots of the WBM, erythrocyte-lysed, and Sca-1+ cell-enriched preparations were measured by manual cell count of viable cells as determined by trypan dye exclusion. Recovery was calculated by dividing the number of cells counted after the lysis of erythrocytes and Sca-1+ enrichment steps by the number of WBM cells harvested. To assess enrichment efficiency, aliquots of each cell preparation were incubated with either PE-conjugated Sca-1 specific or PE-conjugated rat isotype control antibody (Pharmingen, San Diego, Calif.) and analyzed for Sca-1 and/or GFP-expression with a FACSCalibur System (BD Biosciences, San Jose, Calif.). The percentage of Sca-1+ cells was calculated by subtracting the value obtained with the PE-conjugated rat isotype control antibody from that obtained with the PE conjugated Sca-1 specific antibody.

Transplantation.

Two weeks before and 2 weeks after the irradiation procedure, recipient mice were provided sterile food and autoclaved, acidified water (pH 2.0-2.5) containing 50 mg/L Neomycin $SO_4$ and 13 mg/L Polymixin B $SO_4$. Recipient mice were preconditioned by total body irradiation with using a $^{60}Co$ source delivering a single radiation dose of 500 cGy at a rate of 80 cGy per minute. For non-irradiated controls, sham irradiations were performed in parallel. Unless otherwise stated, Sca-1+ cells were transplanted into recipients four hours or 24 hours after the irradiation via lateral tail vein or retroorbital injection. For the tail vein injection approach, 30 $W^{41}/W^{41}$ recipient mice were transplanted via the tail vein injection method with 400,000 Sca-1+ cells harvested from TgN-GFP donor mice. For the retroorbital injection method, an aliquot of 400,000 Sca-1+ cells of the same donor cell preparation was injected into each of the six $W^{41}/W^{41}$ recipient mice with via retroorbital plexus.

Analysis of Engraftment.

At various times post transplantation, peripheral blood was collected via the lateral tail vein. Erythrocytes were lyzed and FACS analysis was performed for GFP-expressing donor cells.

Preparation of eGFP Lentiviral Vector-Transduced Sca-1+ Cells for Transplantation.

Sca-1+ cells were isolated as described above and plated in 6-well retronectin-coated plates at a density of $4 \times 10^6$ cells/well in IMDM media containing fetal bovine serum (FBS), human Flt-3 ligand, murine stem cell factor, murine IL-6, murine IL-1α and murine IL-3 and 100 μM additional dNTPs. After 24 hours, unconcentrated MLV-based viral stock was applied to the cells. After 8 hours the media was removed, and fresh media with cytokines and viral stocks were reapplied. After an additional 8 hours, the media was removed and fresh media with cytokines (without virus) were applied. Cells were then transplanted 12-24 hours after transduction.

Statistical Analysis.

Comparisons of differences between two variables were performed using the two-tailed, two-sample with equal variances, independent t-test. Comparison of multiple groups was performed with one-way ANOVA. Results were considered significant when $p<0.05$. All data are reported as mean±standard deviation.

Results

Enrichment for Sca-1+ Cells.

Table 7 shows the FASC analysis a representative of WBM cell population and its corresponding enriched Sca-1+ cell population. Although WBM cells were isolated from the GFP transgenic mice, only ~80% of the Sca-1+ cells in this cell population expressed GFP (that is, were GFP+). Therefore, the relative percentage of the Sca-1+ cells that were GFP+ versus those that were GFP− during the enrichment process was determined.

TABLE 7

Cell yield, recovery, and enrichment of Sca-1+ and/or GFP+ cells during the Sca-1+ cell enrichment process. Results are shown as mean ± S.D. for four replicate experiments.

|  | Number of cells per donor mouse (×10⁶) | Recovery (%) | % Sca-1+-GFP+ cells | % Sca-1+-GFP− cells | Total % Sca-1+ cells | Fold enrichment of Sca-1+ cells |
|---|---|---|---|---|---|---|
| Whole bone marrow | 116.0 ± 15.5 | (100) | 4.7 ± 0.5. | 1.2 ± 0.4 | 5.8 ± 0.7 | (1) |
| Erythrocytelyzed cell subpopulation | 43.9 ± 8.5 | 37.8 | 8.0 ± 1.7 | 2.8 ± 0.8 | 10.7 ± 0.9 | 2 |
| Sca-1+- enriched cell subpopulation | 3.0 ± 0.7 | 2.6 | 57.7 ± 9.9 | 16.6 ± 5.1 | 74.3 ± 5.3 | 13 |

Table 7 summarizes the cell yield per donor mouse, recovery, percent Sca-1+ (GFP+, GFP−, and total fractions), and fold of enrichment at each isolation step of 4 independent experiments. The overall enrichment of Sca-1+ cells by this procedure was ~13-fold. After the enrichment, approximately 80% of the Sca-1+ cells remained GFP+, demonstrating that this enrichment method does not discriminate GFP+-Sca-1+ cells from GFP−-Sca-1+ cells.

Retroorbital Injection Vs. Tail Vein Injection.

Figure 3A:
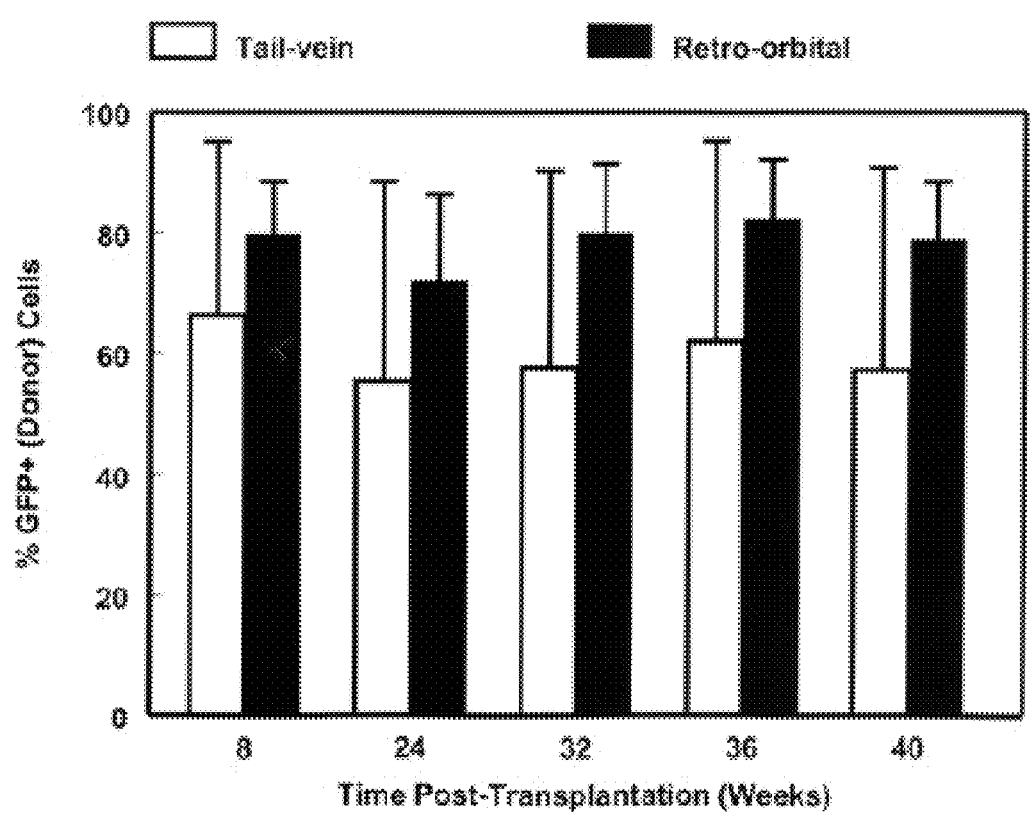
FIGS. 3A-C are bar graphs comparing engraftment efficiency of transplanted hematopoietic stem cells in mice under a variety of conditions.

Tail vein injection and retroorbital injection are two frequently used routes for delivering cells or test compounds into the circulation of recipient in rodents. Accordingly, the engraftment efficiency and the chimera levels between the retroorbital injection method and tail vein injection were compared at 8, 24, 32 and 36 weeks post-transplant and assessed for engraftment (FIG. 3A). At each test time point, every mice (6 of 6: 100%) in the retro-orbitally-injected group demonstrated significant engraftment, whereas only 11 out of 30 (37%) of the tail vein-injected mice showed evidence of engraftment. When the engraftment in those 11 tail vein-injected mice was compared with that in the retro-orbitally-injected mice (excluding the 19 mice non-engrafted tail vein-injected mice), the retroorbital group showed a higher (72-82%) chimeric level than the tail vein group (56-66%) at each time point (FIG. 3A). The variation of the engraftment in the tail vein-injected group was also significantly larger than that in the retroorbital group. Accordingly, Table 8 shows a 3- to 4-fold larger CV in the tail vein group compared to the retroorbital group. The retroorbital injection method is relatively safe to the host, as none of the mice injected by retroorbital injection suffered adverse effects to their eyes or were lost due to anesthesia.

TABLE 8

Comparison of coefficient of variation (CV) of the engraftment between the tail vein-injected group and the retroorbitally-injected group.*

| | CV | | | | |
|---|---|---|---|---|---|
| | 8 weeks | 24 weeks | 33 weeks | 37 weeks | 40 weeks |
| Tail vein-injected group | 0.44 | 0.59 | 0.56 | 0.54 | 0.53 |
| Retroorbitally-injected group | 0.11 | 0.20 | 0.14 | 0.12 | 0.14 |

*CVs were calculated from data presented in FIG. 1. It was calculated as standard deviation divided by mean for each time point.

Effect of Preconditioning on Engraftment Levels.

Figure 3B:
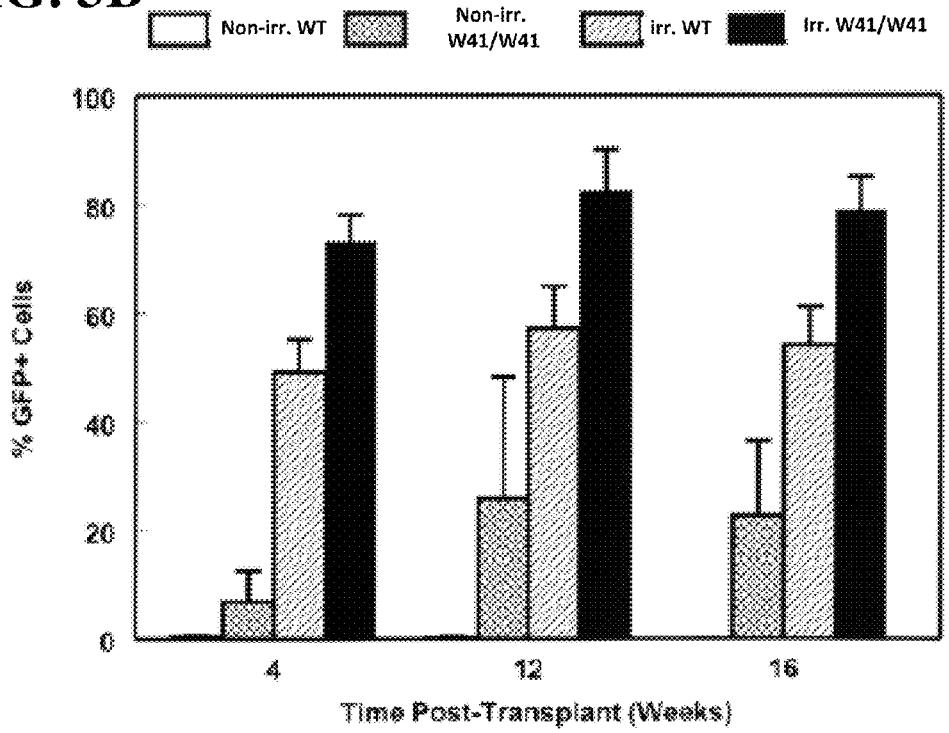

The combined effects of preconditioning and the use of $W^{41}/W^{41}$ recipient mice on engraftment at 4, 12 and 16 weeks were evaluated by comparing engraftment efficiencies in 4 recipient models (N=6 per group): 1) non-irradiated C57BL/6J wild type mice, 2) non-irradiated $W^{41}/W^{41}$ mice, 3) sublethally (500 cGy) irradiated C57BL/6J wild type mice, and 4) sublethally irradiated $W^{41}/W^{41}$ mice. The results are shown in FIG. 3B. At all 3 time points, analysis by one-way ANOVA revealed statistically significant differences between the four recipient models (p<0.01 in all comparisons except at 12 weeks comparisons of wild type vs. $W^{41}/W^{41}$ p<0.05). The engraftment in non-irradiated wild type recipients was negligible (0.54±0.18, 0.24±0.24 and 0.06±0.06% for 4, 12 and 16 weeks, respectively). Non-irradiated $W^{41}/W^{41}$ hosts had significantly increased engraftment (7.0±5.7, 25.8±22.6 and 22.7±13.7%, respectively). Radiation preconditioning of wild type mice markedly improved engraftment at each time point, (49.2±6.0, 57.2±7.8, and 54.0±7.2%, respectively). The highest level of chimerism was observed in the $W^{41}/W^{41}$ recipients receiving the sublethal irradiation (73.1±5.1, 82.6±7.3, 78.9±6.0%, respectively), indicating that the combination of preconditioning and the use of genetically myelosuppressed recipient mice produced at least an additive enhancement in engraftment. The enhanced engraftment produced by the combination persisted for up to more than one year without significant reduction in chimera levels.

Effect of Delay of Injection on Long-Term Reconstitution.

Figure 3C:
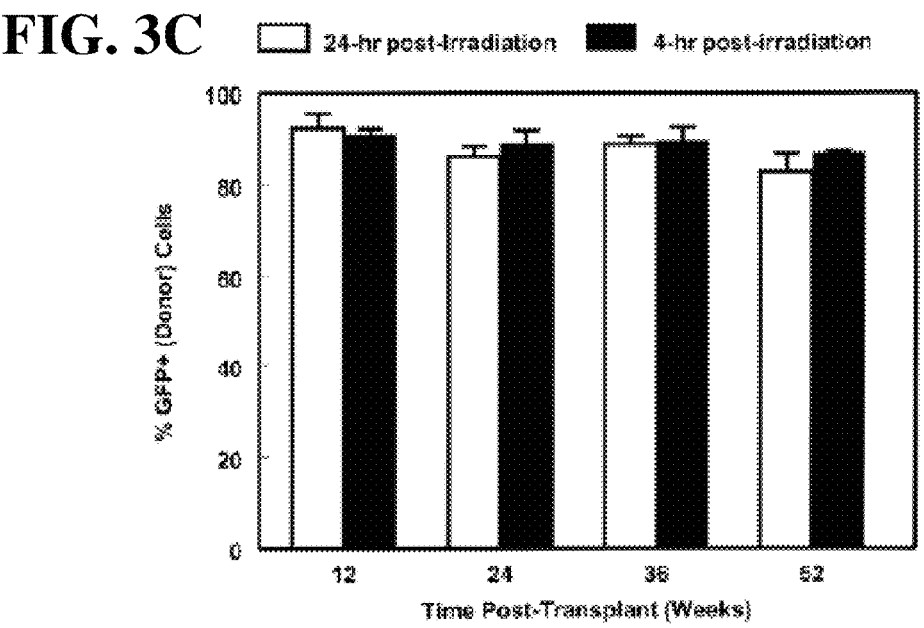

Whether a 24-hour delay of the initiation of HSC transplantation after the sublethal irradiation affected long-term engraftment was also tested. As seen in FIG. 3C, there was no significant difference in engraftment level between mice transplanted 4 hours vs. 24 hours post irradiation at any time point. Furthermore, engraftment was relatively high and persisted up to 52 weeks (experimental endpoint). The 24 hours delay also did not lead to a significant increase in radiation-related morbidity or mortality. These findings indicate that a 24-hour delay between sublethal irradiation and transplantation through retroorbital injection did not affect the short- or long-term engraftment efficiency or cause significant increase in radiation-related morbidity and/or mortality.

Engraftment Efficiency of Genetically Altered Sca-1+ Cells.

Because the objective was to utilize this HSC transplantation strategy to develop a system for evaluating therapies for treating bone disorders and enhancing bone growth, it was important to ensure that ex vivo modification of Sca-1+ cells with viral transduction did not adversely affect engraftment efficiency or levels. To address this issue, Sca-1+ cells of C57BL/6J wild type mice were transduced with a lentiviral vector expressing GFP. Forty-eight hours post-transduction, cells were stained with propridium iodide for assessment of cell viability and GFP expression. The viral transduction caused significant cell death (81%), because a high MOI of viral vector was used. The GFP expression level of the transduced Sca-1+ cells was analyzed with FACS two and five days after transduction, which showed that approximately half of the transduced cells (51% at 2 days and 49% at 5 days post-transduction) expressed the GFP trangene, indicating a ~50% transduction efficiency (FIG. 4A).

An aliquot of 500,000 cells of the transduced cell preparation were injected into 24 sublethally irradiated $W^{41}/W^{41}$ recipient mice (N=12) 48 hours post-transduction. At 9 weeks post-transplant, peripheral blood was collected from recipient mice and assayed for GFP mRNA expression by real-time PCR and for percent GFP positive cells by FACS analysis, which showed greater than 80% GFP positive cells (FIG. 4B). Real-time PCR showed detectable GFP expression in each recipient mouse but varied (mean GFP:GAPDH ratio was 91.9±54.3%). Engraftment was confirmed by FACS analysis for GFP mononuclear blood samples. FIG. 4C shows a 50-60% long-term engraftment level in each of the recipient mice that lasted for greater than 22 weeks.

The results discussed above demonstrate the efficacy of methods for the production of an improved murine Sca-1+ cell-based BMT system, involving the injection of a Sca-1+ cell enriched HSC subpopulation into sublethally irradiated, genetically myelosuppressed $W^{41}/W^{41}$ recipient mice through retroorbital vein 4 to 24 hours post-irradiation. These results demonstrate that this strategy provided consistent (in every recipient mouse), long-term (up to greater than 52 weeks) engraftment of very high chimera levels (as high as 80%) with only a few hundred thousands of Sca-1+ donor cells, but yet caused minimal host morbidity and mortality. The engraftment levels in this study were estimated by measuring the relative amounts of GFP-expressing Sca-1+ donor cells isolated from TgN-GFP transgenic mice in the recipients using FACS. Since approximately 80% of the Sca-1+ cells of the TgN-GFP transgenic mice are GFP+, the actual engraftment in this study is likely to be significantly greater than 80% and probably even approaches full (100% chimera) engraftment. This study also showed that injections of Sca-1+ cells derived from wild type C57BL/6J mice transduced with a lentiviral vector expressing the GFP marker gene yielded highly consistent (in every test mouse) and high levels (50-60%) long-term engraftment. These results demonstrate that the improved HSC-based BMT strategy can be used as a system to evaluate osteogenic therapies, including, for example, gene and cell-based therapies.

Several features of this strategy contribute to achieving consistent, high levels of engraftment with minimal host morbidity and mortality. The strategy uses Sca-1$^+$ cells rather than WBM cells as donor cells. WBM-based transplantation protocols require large numbers (e.g., several millions) of WBM to achieve appreciable engraftment (Uchida et al., *Blood* 83:3758-3779, 1994). Intravenous injections of a large number of cells are technically difficult and notoriously inconsistent. This large cell dose requirement also makes WBM transplantation less desirable for applications such as gene therapy because it necessitates high viral titers and/or high multiplicities of infection for adequate levels of gene transfer. In contrast, Sca-1, a phosphatidylinositol-linked cell surface glycoprotein, is a cell surface marker of primitive HSCs (Spangrude et al., *Science* 241:58-62, 1988; Uchida et al., *Exp. Hematol.* 24:649-659, 1996), which have been shown to home to and engraft in bone after intravenous injection (Krause et al., *Cell* 105:369-377, 2001; Uchida et al., *Exp. Hematol.* 24:649-659, 1996). Thus, one advantage of the Sca-1$^+$ enriched subpopulation strategy over the WBM strategy is the requirement of a much lower number of donor cells for successful engraftment. Consistent with this assumption, as few as about 300,000 to 400,000 Sca-1$^+$ cells yielded high level of long term engraftment, whereas it has been shown that several millions of WBM cells are needed for successful engraftment (Uchida et al., *Blood* 83:3758-3779, 1994). An additional advantage of Sca-1$^+$ cells over WBM cells is that this cell subpopulation has been shown to provide both short-term radioprotection (Zhao et al., *Blood* 96:3016-3022, 2000; Okada et al., *Blood* 80:3044-3050, 1992) and long-term, multi-lineage reconstitution (Osawa et al., *Science* 273:242-245, 1996; Zhao et al., *Blood* 96:3016-3022, 2000; Okada et al., *Blood* 80:3044-3050, 1992) in lethally irradiated mice. Although extra technical steps are needed for the isolation of Sca-1$^+$ enriched subpopulation, recent advances in the fluorescent-assisted cell sorting technology and/or immunomagnetic assisted cell isolation methods makes the isolation of Sca-1$^+$ enriched cell subpopulations relatively routine and cost-effective. As an example, a 13-fold enrichment of Sca-1$^+$ cells was obtained with a single immuno-magnetic column step.

The combined use of myelosuppressed $W^{41}/W^{41}$ mutant mice as the recipients and sublethal irradiation maximizes engraftment and, at the same time, minimizes side effects due to irradiation preconditioning (Trevisan et al., *Blood* 88:4149-4158, 1996). Because the mechanism leading to myelosuppression by irradiation and that in $W^{41}/W^{41}$ mice is different, low doses of irradiation along with the use of $W^{41}/W^{41}$ recipient mice can be used to reduce host mortality and morbidity due to high dosage of radiation without significant reduction in engraftment. The results described above demonstrate that the use of $W^{41}/W^{41}$ recipient mice and a sublethal radiation dose (500 cGy) in combination produced an additive enhancing effect on long-term engraftment with reduced host mortality and morbidity. These results are consistent with previous studies that showed that irradiation preconditioning facilitated the engraftment in $W^{41}/W^{41}$ recipient mice (Trevisan et al., *Blood* 88:4149-4158, 1996).

Most prior BMT procedures require transplantation immediately after irradiation preconditioning to reduce radiation-related mortality. This requirement creates a significant time constraint on the experimental design. The results described above demonstrate that a 24-hour delay between the time of transplantation and the time of the irradiation is feasible in the current transplantation system because no significant differences in short- or long-term engraftment were observed in mice with a 4-hour or a 24-hour delay between irradiation and transplantation or in radiation-related morbidity and mortality in the host animals. This delay allows flexibility of the procedure with respect to the timing of HSC transplantation, which adds a valuable advantage to this Sca-1$^+$ cell-based BMT strategy in comparison to other strategies.

A single irradiation dose of 500 cGy was utilized because previous studies indicated that this dose was the minimal radiation dose that provides sufficient myelosuppression to achieve high levels of engraftment in the C57BL/6J allogenic model (Down et al., *Blood* 77:661-669, 1991). However, lower or higher dosages of irradiation can be used to further reduce host mortality and morbidity or to increase engraftment without a significant increase in host mortality and morbidity depending on individual experimental results.

The most commonly used and convenient route of cell delivery for murine BMT models is intravenous injection into the lateral tail vein. Due to the small size of the lateral tail veins and their potential for venous collapse, injection via tail vein can be technically difficult and highly inconsistent, especially in the hands of a novice investigator. Injection into the retroorbital plexus is a convenient, relatively less intrusive route for delivering test substances in murine models. Compared to tail vein injection, retroorbital injection is less technically demanding and the results are less variable. Previous direct comparison between tail vein injection and retroorbital injection showed no differences in organ distribution or blood concentration of injected material (Price et al., *Proc. Soc. Exp. Biol. Med.* 177:347-353, 1984), indicating that retroorbital injection is a reliable delivery method for Sca-1$^+$ cells. Retroorbital injection resulted in greatly enhanced engraftment success (from 37% to 100%), higher engraftment levels, and a significant reduction in variation as compared to the tail vein method. The retro-orbital injection method also led to engraftment in every injected mouse and a 3- to 4-fold reduction in intra-assay variations as compared to the tail vein method. Since the power of an experiment is directly proportional to sample size and magnitude of the difference to be detected and inversely proportional to the inherent variability of the observations (Samuals, *Statistics for the Life Sciences*, Dellen Publishing Co., San Francisco, Calif., 1989), the reduction in intra-assay variability should result in an increase in experimental power and the ability to detect small differences, and/or decreased sample size required. Additionally, no increased risk of fatality due to anesthesia was observed using this method (less than 1% of mice due to anesthesia or other complication). This risk can be further minimized by optimizing the anesthesia dose according to the weight and strain of the recipient mouse.

The use of GFP transgenic mouse Sca-1$^+$ cells as the donor cells affords a convenient and reliable means to distinguish cells of donor from host origin and as such facilitates assessments of engraftment. This approach is feasible because both the TgN-GFP transgenic mice and the $W^{41}/W^{41}$ recipient mice are of C57BL/6J background. The C57BL/6J mouse strain offers several additional attractive features for use in studies of HSC-based gene and cell therapy. First, this strain of mouse is widely used in animal research, and a large body of genetic and biological information about this mouse strain is known. Second, numerous transgenic, knockout, or mutant variations have been developed on this strain background and are available for use with the described strategy in assessing the functional role of the test compound, e.g., a test gene. Third, since it has been demonstrated that up to 99% of cells with marrow reconstituting ability are contained within the Sca-1+ subset in C57BL/6J mice (Spangrude et al., *Blood* 82:3327-3332, 1993), the harvest of Sca-1+ cells from C57BL/6J background strain of mice provides cell preparations with relatively high repopulating potential, which is an important trait for BMT strategy.

Example 3

Sca-1+ Hematopoietic Progenitor Cell-Based Systemic Gene Therapy

Materials and Methods

Animals.

The TgN β-actin-eGFP (TgN-GFP) donor mice and wild-type C57BL/6J mouse strain were purchased from Jackson Laboratories (Bar Harbor, Me.) [TgN-GFP mice are GFP transgenic mice].

Bone Marrow Sca-1+ Cell Population Isolation.

Whole bone marrow (WBM) cells were harvested from TgN-GFP mice by flushing tibiae and femurs with sterile phosphate-buffered saline (PBS) supplemented with 0.5% bovine serum albumin (BSA) using a 26-g needle and syringe. Erythrocytes were removed by a 5-minute osmotic lysis at room temperature using a solution of 155 mM $NH_4Cl$, 10 mM $KHCO_3$, and 110 μM $Na_2EDTA$, followed by rinsing with PBS. The cell preparation ($1\times10^8$ cells per 0.8 ml of BSA-supplemented PBS) was then incubated with magnetic microbeads conjugated with antibody specific for Sca-1 (0.2 ml beads per $1\times10^8$ cells) for 20 minutes at 4° C. and applied twice to an AutoMacs™ automated magnetic separation column according to manufacturer's instruction (Miltenyi Biotec, Inc, Auburn, Calif.). Cell yields were measured by manual cell count of viable cells as determined by trypan dye exclusion. Recovery was calculated by dividing the number of cells counted after the lysis of erythrocytes and Sca-1+ enrichment steps by the number of WBM cells harvested. To assess enrichment efficiency, aliquots of each cell preparation were incubated with PE-conjugated Sca-1 specific or PE-conjugated rat isotype control antibody (Pharmingen, San Diego, Calif.) and analyzed for Sca-1 with a FACSCalibur System (BD Biosciences, San Jose, Calif.). The percentage of Sca-1+ cells was calculated by subtracting the value obtained with the PE-conjugated rat isotype control antibody from that obtained with the PE conjugated Sca-1 specific antibody.

Transduction of Sca-1+ Cells with MLV-Based Vectors.

The VSV-G pseudotyped MLV-based vectors expressing the modified FGF-2 gene (pY-BMPFGFC2SC3N), the BMP2/4 hybrid gene (Gysin et al., *Gene Ther.* 9:991-999, 2002; Peng et al., *Mol. Ther.* 4:95-104, 2001), or the eGFP gene (pY-GFP) were constructed as described previously (Peng et al., *Mol. Ther.* 4:95-104, 2001). For the transduction, Sca-1+ cells were plated in 6-well retronectin-coated plates at a density of $4\times10^6$ cells/well in IMDM media containing 10% fetal bovine serum (FBS), human Flt-3 ligand, murine stem cell factor, murine IL-6, murine IL-1α and murine IL-3 and 100 μM dNTPs. After 24 hours, the unconcentrated MLV-based viral stock was applied to the cells. After 8 hours the media was removed, and fresh media with cytokines and viral stocks were reapplied. After an additional 8 hours, the media was removed and fresh media with cytokines (without virus) were again applied. Cells were used for transplantation within 12-24 hours after transduction.

Transplantation.

Two weeks before and 2 weeks after the irradiation procedure, recipient mice were provided sterile food and autoclaved, acidified water (pH 2.0-2.5) containing 50 mg/L neomycin sulfate and 13 mg/L polymixin B sulfate. Recipient mice were preconditioned by total body irradiation with using a $^{60}$Co source delivering a single radiation dose of 500 cGy at a rate of 80 cGy per minute. The transduced donor Sca-1+ cells were then transplanted into anesthetized (with 62 mg/kg ketamine and 12 mg/kg xylazine) recipient mice 4 hours post-irradiation via retro-orbital injection. An aliquot of 500,000 Sca-1+ cells (in 30 μl sterile saline) were injected into each $W^{41}/W^{41}$ recipient mouse via retroorbital plexus with a 30-g, ½-inch needle. At the endpoint, mice were anesthetized, decapitated, and whole blood (~700 μl) was collected from each mouse. The percent eGFP-expressing cells (to monitor engraftment) were determined by FACS analysis. Serum FGF-2 protein levels were determined by ELISA using a commercial kit (R&D Systems, Minneapolis, Minn.). Aliquots of serum samples were kept frozen at −80° C. for skeletal alkaline phosphatase (ALP), PTH, and calcium assays. Serum ALP and calcium were performed by the Hitachi 912 Clinical Chemistry analyzer. The mean inter- and intra-assay CV for serum calcium assay was <2% with the sensitivity of 0.2 mg/dL and measuring range of 0.2-18 mg/dL. Serum PTH was measured by ELISA (PTH Immunoassay Kit, ALP-Co™). The bone extract ALP activity was assayed by a colorimetric assay as described previously (Farley et al., *Calcif. Tissue Int.* 50:67-73, 1992). BMP-4 level in CMs and cell extracts were estimated from an immunoblot assays by comparing its relative densitometric intensity with that of known amounts of BMP-4 recombinant protein.

Analysis of Engraftment of Transduced Cells.

At various times post transplantation of pY-GFP-transduced Sca-1+ cells, peripheral blood was collected via the lateral tail vein. Erythrocytes were lysed and FACS analysis was performed for percent eGFP-expressing donor cells.

Immunohistochemical Staining of eGFP-Expressing Cells.

Donor cells from TgN-GFP transgenic mice were identified by immunohistochemical staining of eGFP to avoid interference from autofluorescence in bone sections. Briefly, thin (5 μm) frozen longitudinal sections of right femurs of recipient mice were prepared by cryostat, immediately immersed in 100% methanol for 20 min at room temperature. The sections were then re-hydrated and rinsed with PBS. Non-specific antigens were inactivated by exposing the sections to 3% $H_2O_2$ for 10 min at room temperature. The sections were then rinsed with PBS 4-5 times and the non-specific antibody binding sites were blocked by incubating the sections with 20% normal rabbit serum for 30 min at 37° C. The sections were then incubated with the chicken anti-GFP antibody (1:100 dilution) followed by incubation with the biotinylated anti-chicken IgG secondary antibody (1:250 dilution) using the Ventana ES immunostainer (Ventana, Tucson, Ariz.), accordingly the manufacturer's instruction. The immunostained sections were counterstained with hematoxylin for 30 sec, air-dried, and covered with coverslips. Osteoblasts were identified as a palisade of large basophilic cells directly lining the bone surface. Osteoclasts were identified as large multinucleated, irregularly-shaped cells with a striated perimeter zone of attachment (ruffled border) to the bone surface (resorption pits).

pQCT Measurements.

Femurs of each mouse were dissected, formalin-fixed, and stored in PBS (containing 0.5% sodium azide). Cross-sectional and volumetric bone parameters were measured using an XCT 960M with XCT software version 5.40 in a multi-specimen holder designed for the XCT 960M. Voxel size was reduced to 0.07 mm for the analysis. The bone scans were analyzed with two different outer threshold settings to separate bone from soft tissue. A threshold setting of 630 mg/cm$^3$ was used to determine bone areas and surfaces. A second analysis with a threshold of 230 mg/cm$^3$ was used to determine mineral content. These thresholds were selected to yield area values consistent with histomorphometrically derived values. The measured parameters included total, trabecular, and cortical volumetric bone mineral density (vBMD), cortical thickness, and periosteal and endosteal circumferences. Total, cortical, and trabecular vBMD values were calculated by dividing the total, cortical, and trabecular mineral content by the total, cortical, and trabecular bone volume, respectively, and expressed as mg/cm$^3$.

Bone Histomorphometry.

Bone histomorphometry was performed in the femurs. After pQCT measurements, the left femurs were decalcified in 14% EDTA for 2 weeks at 4° C., dehydrated in ethanol, infiltrated, and embedded in paraffin wax. Longitudinal serial sections (5 µm in thickness) were stained with hematoxylin and eosin (H&E stain) or Mallory's trichrome stain (for detection of collagen). To measure bone resorption parameters, serial sections were stained for tartrate-resistant acid phosphatase (TRAP) activity as described previously (Boyce et al., *Endocrinology* 136:5751-5759, 1995). The TRAP stained sections were counterstained with methyl green and light green SF yellowish.

Right femurs were embedded into methylmethacrylate (MMA) for assessment of bone mineralization parameters. Briefly, the right femurs were dehydrated with 95% and 100% ethanol each for two days. The bone specimens were then infiltrated with a mixture containing 85 ml of MMA, 10 ml of glycolmethacrylate, 5 ml of dibutylphthalate, 5 ml of polyethylene-glycol, and 0.9% benzoylperoxide for 4-6 days. This solution was changed every 2-3 days. Bone specimens were then placed in plastic molding cups (6×12×5 mm) and orientated at a position with the anterior part of the femur facing down. Polymerization was initiated with 1% JB4 solution B (Polysciences, Inc., Warrington, Pa.). After 5-10 min of vacuum, bone specimens were carefully transferred into a gas jar and flushed with nitrogen for 5-10 min. The gas jar was then sealed and placed in cold for 2 days for polymerization. Serial sections (5-10 µm in thickness) were stained with Goldner's trichrome stain.

Statistical Analysis.

Comparisons of differences were performed using the two-tailed, two-sample with equal variances, independent t-test, one-way ANOVA, and linear regression. Results were considered significant when p<0.05. All data are reported as mean±standard error of the mean.

Preparation of the MLV.tet.e.GFP and MLV.tet.FGF* Vectors.

The doxycycline-inducible MLV-based vector system (rtTA-GYT) was based on the tet-on inducible system reported by Das et al., *J Biol Chem* 279, 18776-18782, 2004). The system utilized herein has 3 additional mutations form rtTA (mutations at S12G, F86Y and A209T from rtTA-S2) and exhibits better inducibility than the original clones used by Das et al.). The rtTA-GYT and the tetracycline controlled promoter (TetO-P) were incorporated into the MLV.eGFP and MLV.FGF2* vectors to generate MLV.tet.eGFP and MLV/tet.FGF* respectively.

Results

Transduction of Murine Sca-1$^+$ Cells with MLV-Based Vectors.

To demonstrate that Sca-1$^+$ cells can be transduced with MLV-based vectors, Sca-1$^+$ cells isolated from wild-type C57BL/6J mice were transduced with a pY-GFP MLV-based vector and the percent of GFP-expressing Sca-1$^+$ cells was measured 48-hr after transduction to assess transduction efficiency. The transduction efficiency was consistently greater than 50%. The amounts of FGF-2 protein was also measured in the conditioned media (CMs) of Sca-1$^+$ cells transduced with the MLV vector expressing the modified FGF-2 gene (pY-BMPFGFC2SC3N) 72 hrs after transduction and compared to those in the CMs of Sca-1$^+$ cells transduced with the MLV vector expressing the unmodified FGF-2 gene (pY-FGF) or the marker gene, β-galactosidase (pY-β-gal). The average amount of FGF-2 secreted by the pY-β-gal-transduced Sca-1$^+$ cells was barely detectable (~2 ng/10$^6$ cells/24 hrs) and that of pY-FGF-transduced Sca-1$^+$ cells was low (~18 ng/10$^6$ cells/24 hrs). In contrast, the amount of FGF-2 secreted by pY-BMPFGFC2SC3N-transduced Sca-1$^+$ cells was >320 ng/10$^6$ cells/24 hrs (>15-fold more than that by pY-FGF-transduced cells). Sca-1$^+$ cells transduced with pY-BMP2/4 vector secreted ~10 ng/10$^6$ cells/24 hrs mature BMP-4 protein (estimated by the immunoblot assay).

Evidence that Transplanted Sca-1$^+$ Cells can Contribute Donor Progenitors to the Osteoblastic Lineage.

To assess whether the engrafted Sca-1$^+$ enriched cell population can be differentiated into bone cells at the endosteal bone surface, eGFP-expressing Sca-1$^+$ cells isolated from the TgN-GFP transgenic donor mice were transplanted into sub-lethally W$^{41}$/W$^{41}$ recipient mice, and the bone marrow cavity of recipient mice for GFP-expressing bone cells (by immunohistochemical staining) was analyzed one year post-transplantation. Frozen sections of mouse femurs receiving GFP-expressing Sca-1+ donor cells were immunostained for GFP one year post-transplantation. There were numerous osteoblast- and osteoclast-like cells that stained strongly for GFP on the endosteal bone surface. While it is expected that Sca-1$^+$ cells can differentiate into osteoclastic cells, since osteoclastic cells are derived from cells of the hematopoietic lineage, it is surprising to note that the donor GFP-expressing Sca-1$^+$ cells most predominantly localized to the marrow cavity along the endosteal surface can also be differentiated into osteoblastic cells. These findings indicate that the donor Sca-1$^+$ enriched cell population can contribute osteoblastic progenitors to the recipient mice.

Retro-Orbital Delivery of MLV-Transduced Sca-1$^+$ Cells into Sub-Lethally Irradiated W$^{41}$/W$^{41}$ Recipient Mice Led to Engraftment.

To confirm the feasibility of using the Sca-1$^+$ enriched cell population to deliver the modified FGF-2 gene to bone marrow cavity, approximately 500,000 Sca-1$^+$ cells transduced with the modified FGF-2 MLV vector (pY-BMPFGFC2SC3N) were transplanted via retro-orbital plexus into 8 sub-lethally irradiated female W$^{41}$/W$^{41}$ recipient mice. For assessment of engraftment and as a control for comparison, the same number of Sca-1$^+$ cells transduced with the pY-GFP marker gene was also transplanted into 8 sub-lethally irradiated female W$^{41}$/W$^{41}$ recipient mice. At 10 and 12 weeks post-transplantation, peripheral blood was collected and percent GFP-expressing cells were determined by FACS analysis. All mice were sacrificed at 12 weeks and the percent of GFP-expressing bone marrow cells was determined (Table 9). The average transduction and engraftment in this experiment (as reflected by percent GFP-expressing cells in the peripheral blood) was ~35%. The percent of GFP-expressing bone marrow cells in the engrafted recipients was about one-third to one-half lower than that in peripheral blood. As anticipated, the mice that received the modified FGF-2 vector-transduced Sca-1+ cells did not have significant numbers of GFP-expressing cells (background levels).

TABLE 9

Mean percent eGFP-expressing cells in the peripheral blood and in bone marrow of recipient mice at 10 and 12 weeks post-transplantation.* (Mean ± SEM, n = 8).

| Treatment Group | Peripheral Blood Cells | | Bone Marrow Cells |
|---|---|---|---|
| | Week 10 | Week 12 | Week 12 |
| GFP-expressing Sca-1+ cells transplanted Group | 35.5 ± 4.3% | 34.1 ± 4.1% | 11.6 ± 2.4% |
| Modified FGF-2-expressing Sca-1+ cells transplanted Group | 0.40 ± 0.24% | 0.32 ± 0.15 | 0.44 ± 0.11 |

*% eGFP-expressing cells were determined by FACS analysis as described in Methods after erythrocytes were removed by osmotic lysis.

To confirm that Sca-1+ cells transduced with the modified FGF-2 vector also engrafted, the serum FGF-2 levels in the recipient mice were measured 10 or 12 weeks post-transplantation (Table 10). The average serum FGF-2 level in the pY-GFP-transplanted control mice was 35.6 pg/ml, which was not significantly different from that in untreated control mice. In contrast, the average serum FGF-2 level in the modified FGF-2 vector-transplanted recipient mice was ~100-fold higher than that in pY-GFP-transplanted control mice. The serum level of individual recipient mouse was variable (ranging from 77 pg/ml to 6,400 pg/ml) with a within-group coefficient of variance (CV) of 0.98. In spite of the within-group variation, the increase in serum FGF-2 level was highly significant (p=0.014). These findings are consistent with the previous findings that retroviral transduction does not limit engraftment (Kang et al., *Hum. Gene. Ther.* 12:1663-1672, 2001).

Figure 5A:
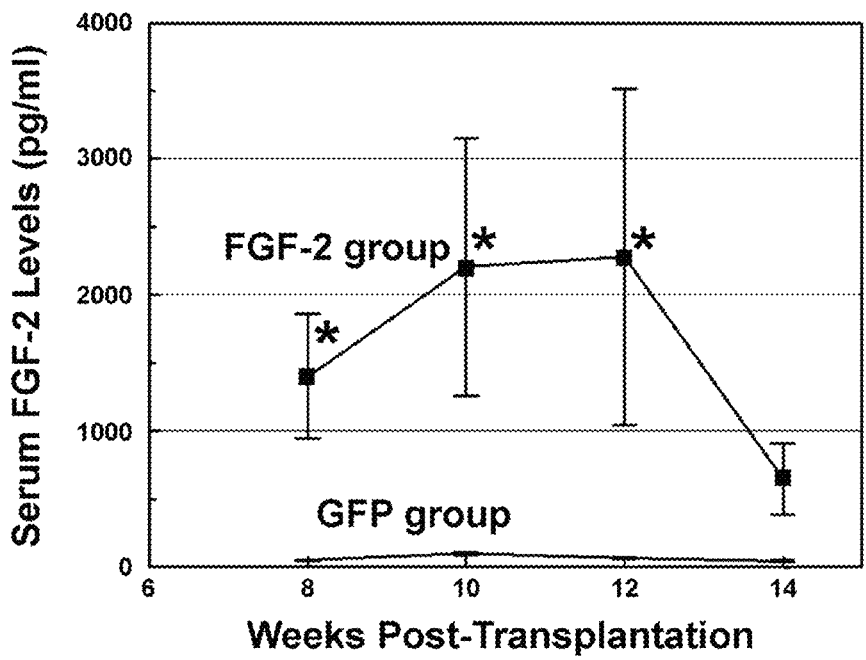
FIGS. 5A and B are line graphs indicating serum FGF-2 and ALP levels with respect to time post-transplantation (in weeks) in recipient mice.

The serum FGF-2 level of each mice at 8-, 10-, 12- and 14-week post-transplantation was measured and is shown in FIG. 5A. Earlier time points were not performed because previous studies have indicated that Sca-1+ cells engraft over a period of 4 to 8 weeks (Tomita et al., *Blood* 83:939-948, 1994). With the exception of the 14-week time point, the serum FGF-2 level of the FGF-2 group at each time increased with time and was significantly higher than that of the GFP control group.

In a separate experiment, the engraftment of pY-BMP2/4-transduced Sca-1+ cells was assessed by measuring the presence of the BMP2/4 gene in genomic DNA of peripheral blood of recipient mice using a PCR-based assay. The relative level of BMP2/4 gene incorporated in DNA of recipient mice was very similar to that of β-gal gene in recipient mice transplanted with pY-β-gal-transduced Sca-1+ cells. This suggests that the pY-BMP2/4-transduction did not significantly affect the engraftment of pY-BMP2/4-transduced Sca-1+ cells.

Transplantation of Modified FGF-2-Expressing Sca-1+ Cells Induced Endosteal Bone Formation in Recipient Mice.

Table 10 shows that the recipient mice of the modified FGF-2 vector-transduced Sca-1+ cells at 10- to 12-week post-transplantation showed a significant (p=0.021) increase in serum ALP activity [a biochemical marker of bone formation (Farley et al., *Metabolism* 35:563-571, 1986)] compared to recipient mice receiving the pY-GFP-transduced cells. Serum osteocalcin level (another bone formation marker) in the FGF-2 group at 10- to 12-week was also higher than that in the GFP control group (9.91±2.67 vs. 8.05±0.18 ng/ml). To confirm an increase in bone ALP levels in the FGF-2 group, the ALP activity in tibial extracts was measured, normalized against dried bone weight (Table 10). The FGF-2 group showed a 34-fold elevation (P=0.022) in the tibial ALP activity compared to the GFP control group. A similar increase was seen with the tibial ALP specific activity (normalized against the bone extract protein). The elevated levels of serum and bone biochemical markers of bone formation in the FGF-2 group suggest an increase in bone formation.

TABLE 10

Serum FGF-2, ALP, and osteoclacin levels and tibial ALP levels in the recipient mice 10- or 12-weeks post-transplantation.[a] (Mean ± SEM, n = 8).

| Treatment Group | Serum FGF-2[b] (pg/ml) | Serum ALP (mU/ml) | Serum Osteocalcin (ng/ml) | Tibial ALP (mU/mg dried bone) |
|---|---|---|---|---|
| GFP-expressing Sca-1+ cells transplanted group | 35.6 ± 2.1 (28-43)[c] | 177.8 ± 8.6 (145-212)[c] | 8.05 ± 0.18 (4.2-12.8)[c] | 0.149 ± 0.049 (0.006-0.307)[c] |
| Modified FGF-2-expressing Sca-1+ cells transplanted group | 2,502.9 ± 929.4[d] (77-6,400)[c] | 271.9 ± 37.3[e] (166-389)[c] | 9.91 ± 2.67[f] (3.5-24.8)[c] | 5.189 ± 1.724[g] (0.451-13.128)[c] |

[a]Three of the eight pY-BMPFGFC2SC3N-transplanted recipient mice were noticeably ill and were euthanized at week 10. The rest of the mice were euthanized at week 12.
[b]Most of the pY-BMPFGFC2SC3N-transplanted recipient mice had serum FGF-2 levels higher than the upper limit of the ELISA assay (>640 pg/ml). The reported values for these mice were extrapolated from the standard curve.
[c]Ranges.
[d]p = 0.014, two-tailed Student's t-test.
[e]p = 0.021, two-tailed Student's t-test.
[f]p = n.s., two-tailed Student's t-test.
[g]p = 0.022, two-tailed Student's t-test.

To evaluate the time-course of engraftment of modified FGF-2 vector-transduced Sca-1+ cells, the pY-BMPFGFC2SC3N-transduced Sca-1+ cells (500,000 cells) and the pY-GFP-transplanted Sca-1+ cells were each transplanted into 8 sub-lethal female W[41]/W[41] recipient mice.

The serum and tibial bone extract ALP activities in eight recipient mice transplanted with pY-BMP2/4-transduced Sca-1+ cells were determined at 14-weeks post-transplantation and compared to those in eight recipient mice transplanted with pY-GFP-transduced Sca-1+ cells. Neither the serum ALP level (183.6±10.8 mU/ml in the pY-GFP group vs. 174.5±11.7 mU/ml in the pY-BMP2/4 group, p=N.S.) nor the tibial extract ALP level (0.079±0.005 mU/mg dried bone in pY-GFP group vs. 0.079±0.008 mU/mg dried bone in pY-BMP2/4 group, p=N.S.) was significant different between the pY-BMP2/4 group and the pY-GFP control group. This indicates that, in contrast to the modified FGF-2 treatment, the BMP-2/4 treatment failed to produce an osteogenic effect in this system.

Figure 5B:
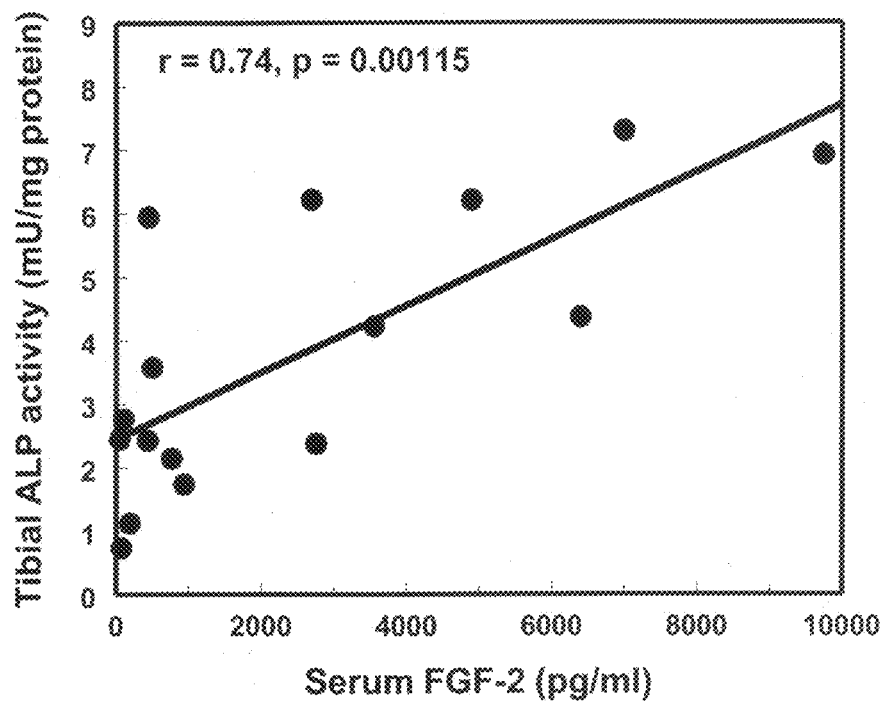
FIG. 5B illustrates the correlation between serum FGF-2 levels and tibial extract ALP activity (normalized against dried bone weight) in recipient mice of Sca-1+ cells transduced with the modified FGF-2 MLV-vector (pY-BMPFGFC2SC3N) at 10- or 12-week post-transplantation.
Figure 6:
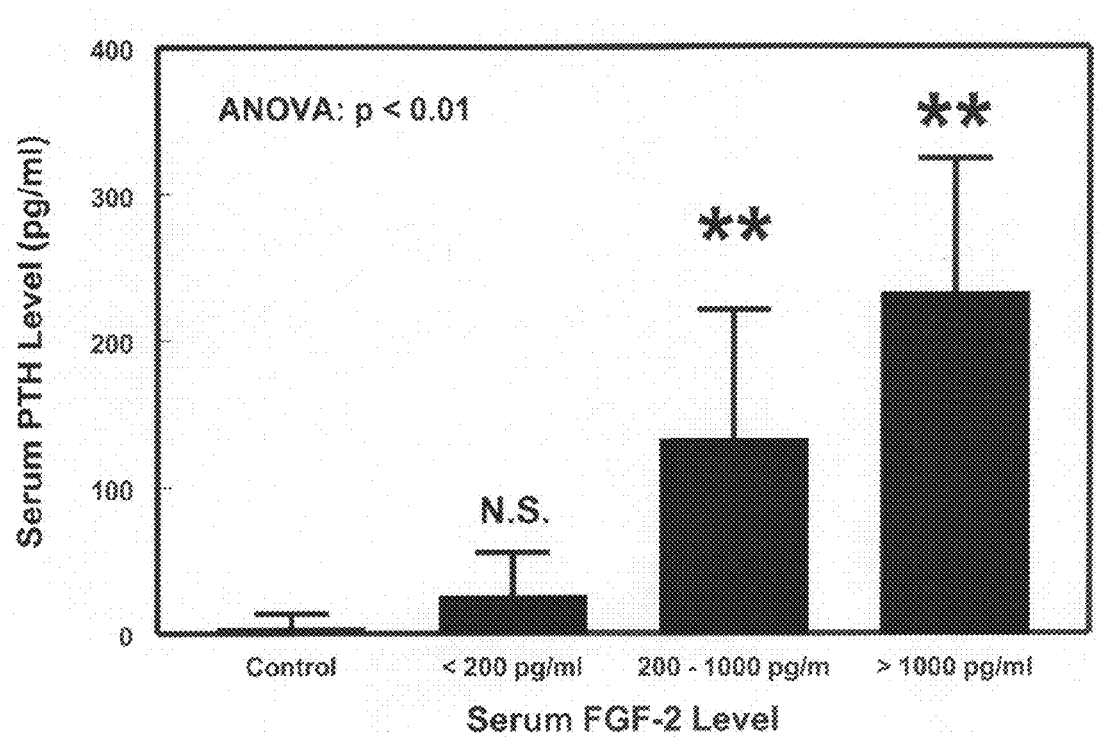
FIG. 6 is a bar graph showing elevated serum PTH levels in recipient mice transplanted with pY-BMPFGFC2SC3N-transduced Sca-1+ cells. Serum parathyroid hormone (PTH) levels in mice transplanted with Sca-1+ cells transduced with either pY-GFP (control) or pY-BMPFGFC2SC3N vector. Mice transplanted with Sca-1+ cells transduced with pY-BMPFGFC2SC3N vector were stratified according to serum FGF-2 levels: control (mean 35 pg/ml); low (<200 pg/ml); intermediate (200-1000 pg/ml); and high (>1000 pg/ml).

To evaluate the relationship between the increase in serum FGF-2 levels and bone ALP activity, the tibial ALP activity was plotted against the serum FGF-2 level of the 8 mice in the FGF-2 group (FIG. 5B). There was a highly significant correlation (r=0.70, p<0.004) between the two parameters, showing that the increase in the bone ALP activity (bone formation) is associated with the increase in the serum FGF-2 level of the recipient mice.

Various parameters of bone mineral density (BMD) and bone mass were measured in recipient mice using pQCT. The combined results of several experiments are shown in Table 11. At 10- to 14-week post-transplantation (end-point), there was a significant increase in total vBMD (14%) and trabecular vBMD (2.5-fold), but not cortical vBMD, in the FGF-2 group compared to the GFP control group. The small (4%) decrease in endosteal circumference in the FGF-2 group compared to the GFP control group is consistent with an increase in endosteal bone formation. These findings are consistent with a previous study demonstrating that FGF-2 protein administration in the rat induced bone formation primarily at trabecular bone sites (Mayahara et al., *Growth Factors* 9:73-80, 1993). The FGF-2 group also showed a small (13%) but statistically significant decrease in cortical thickness and a significantly shorter (8%) periosteal circumference. These findings suggest that the transplantation of modified FGF-2-expressing Sca-1+ cells, while led to increase in endosteal trabecular bone formation, may have caused bone loss at cortical and/or periosteal bone sites. Consistent with a lack of osteogenic response by the systemic BMP2/4 ex vivo gene transfer approach, Table 11 also shows that the BMP2/4 treatment produced no significant effect on any of the test pQCT bone parameters compared to the pY-GFP control group.

Linear regression analysis between the serum FGF-2 level and each of the measured pQCT parameters revealed a highly significant positive correlation between serum FGF-2 and total vBMD (r=0.37, p<0.05) and between serum FGF-2 and trabecular vBMD (r=0.54, p<0.002). Conversely, serum FGF-2 inversely and significantly correlated with cortical thickness (r=-0.51, p<0.005), periosteal circumference (r=-0.62, p<0.0004), and endosteal circumference (r=-0.47, p<0.01).

Effects of Transplantation of Modified FGF-2-Expressing Sca-1+ Cells on Growth and the Size of Major Organs.

To determine whether the transplantation of modified FGF-2-expressing Sca-1+ cells had adverse effects on the growth of recipient mice, the body weight of each mouse was measured at week 7 and week 12. There was no significant difference in the growth rate between the FGF-2 group and the GFP control group, indicating that the elevated circulating FGF-2 did not have an adverse effect on the growth of recipient mice. To test whether the transplantation of modified FGF-2-transduced Sca-1+ cells has an adverse effect on the general health of the recipient mice, the weight of major internal organs was measured at the time of the sacrifice (week 14). Table 12 shows that the increased FGF-2 expression in the FGF-2 group did not significantly affect the weight of the heart, kidneys, lung, and intestine/stomach of recipient mice compared to the GFP control group at 14 weeks post-transplantation. Conversely, the weight of the spleen and the liver was each significantly increased, indicating an enlargement of these organs. It is especially true for the spleen, since the average weight of spleen in the FGF-2 group was increased 4.5-fold. However, with the exception of the enlarged spleen, a gross examination of these organs at the time of dissection did not reveal obvious abnormalities.

TABLE 12

Effects of transplantation of FGF-2 expressing Sca-1+ cells on the weight of various internal organs of recipient mice at 14-week post-transplantation.

| Internal organ (gm) | GFP group | FGF-2 group | p-value* |
| --- | --- | --- | --- |
| Heart | 0.138 ± 0.008 | 0.133 ± 0.011 | n.s. |
| Kidneys (average) | 0.165 ± 0.005 | 0.169 ± 0.006 | n.s. |
| Spleen | 0.082 ± 0.007 | 0.370 ± 0.057 | <0.0001 |

TABLE 11

Effects of transplantation of Sca-1+ cells transduced with the MLV-GFP vector, the MLV-modified FGF-2 vector or the MLV-BMP2/4 vector on the cross-sectional and volumetric bone parameters of the femurs of recipient mice at week 14 post-transplantation. (Mean ± SEM, n = 16).

| Bone Parameters | GFP group | FGF-2 group | BMP-4 group |
| --- | --- | --- | --- |
| Total vBMD (mg/cm$^3$) | 742.0 ± 11.7 | 847.0 ± 68.9* | 742.1 ± 9.9 |
| Trabecular vBMD (mg/cm$^3$) | 229.0 ± 11.7 | 573.0 ± 113.1*** | 270.1 ± 15.5 |
| Cortical vBMD (mg/cm$^3$) | 1,099.0 ± 18.4 | 1,115.0 ± 49.9 | 1,092.7 ± 23.9 |
| Cortical thickness (mm) | 0.292 ± 0.007 | 0.254 ± 0.021* | 0.293 ± 0.007 |
| Periosteal circumference (mm) | 5.20 ± 0.09 | 4.80 ± 0.17** | 5.22 ± 0.07 |
| Endosteal circumference (mm) | 3.36 ± 0.08 | 3.22 ± 0.09 | 3.37 ± 0.05 |

*p < 0.05,
**p < 0.01, and
***p < 0.001.

TABLE 12-continued

Effects of transplantation of FGF-2 expressing Sca-1+ cells on the weight of various internal organs of recipient mice at 14-week post-transplantation.

| Internal organ (gm) | GFP group | FGF-2 group | p-value* |
|---|---|---|---|
| Liver | 1.203 ± 0.112 | 1.495 ± 0.053 | <0.05 |
| Lung | 0.367 ± 0.021 | 0.364 ± 0.040 | n.s. |
| Intestine/Stomach | 2.996 ± 0.104 | 3.221 ± 0.212 | n.s. |

*Two-tailed student's t-test.

Effects of Transplantation of Modified FGF-2 Expressing Sca-1+ Cells on the Histomorphometry of Long Bones in Recipient Mice.

Gross examination of the long bones during dissection revealed an unusual gross appearance in recipient mice that had very high serum FGF-2 levels (>4,000 pg/ml). Femurs were dissected from a representative recipient mouse receiving transplantation with GFP-transduced Sca-1+ cells and from a representative recipient mouse receiving the modified FGF-2 MLV vector, which showed a very high (>4,000 pg/ml) serum FGF-2 level. The bones were dissected from recipient mice 10-week post-transplantation. Instead of the characteristic maroon color of long bones (representing the red marrow), the femurs of mice with high serum FGF-2 levels were white (without the appearance of the red marrow). Without being bound by theory, the lack of bone marrow within the marrow cavity explains the lack of the characteristic maroon color of red marrow in these few bones. Since the spleen and, to some extent, the liver are the extramedullary sites for blood cell production, the lack of bone marrow also helps to explain the enlargement of the spleen and the liver in recipient mice receiving transplantation of modified FGF-2-expressing Sca-1+ cells.

To further evaluate the de novo endosteal bone formation, histomorphometric analysis was performed on the femurs. One femur of each mouse was demineralized and embedded in paraffin. Serial longitudinal sections were stained with hematoxylin and eosin (H&E) for visualization of tissue structure and also with Mallory's stain for collagenous fibers. The contralateral femur was embedded in methylmethacrylate. Longitudinal serial sections were then stained with Goldner's stain for matrix mineralization. The mice were arbitrarily divided into three groups according to their serum FGF-2 level: 1) those with basal serum FGF-2 levels (<35 pg/ml) [the GFP control mice]; 2) those with intermediate serum FGF-2 levels (50-200 pg/ml); and 3) those with high serum FGF-2 levels (>1,000 ng/ml). The H&E stained mid-diaphyseal sections confirm that the dark purplish-stained bone marrow seen in the basal serum FGF-2 control group was completely replaced by the pinkish bone-like tissues in the high serum FGF-2 group. In the intermediate serum FGF-2 diaphyseal sections, there was also evidence that a significant amount of bone marrow was replaced with newly formed bony tissues, some of which even extended to endosteal surfaces. While some of this newly formed bone appeared to be woven bone, there was a considerable amount of normal, lamellar bone. The Mallory's stained sections shows that the pinkish stained areas within the marrow cavity of the groups of mice with intermediate or high serum FGF-2 seen in H&E sections also stained strongly for collagen fibers, confirming that the newly formed tissues within the bone marrow cavity were bony tissues. When the un-demineralized sections were stained with Goldner's stain, the bones of the control mice and those of mice which had intermediate serum FGF-2 levels each showed only mineralized bones without detectable unmineralized reddish stained bony tissues. The amount of mineralized bone was much more in the group with intermediate serum FGF-2 than the control group. In contrast, there was abundance of unmineralized osteoid-like tissues in mice with high serum FGF-2, especially in the marrow cavity where newly formed bony tissues were located. These histomorphometric observations confirm that transplantation of Sca-1+ cells expressing modified FGF-2 induced massive de novo endosteal bone formation, and suggest that the bone formation was so robust that the levels of minerals present are not optimal to fully mineralize the newly formed bone, leading to osteomalacia.

Evidence that Excessive Endosteal Bone Formation in Mice with High Serum FGF-2 Developed, Hypocalcemia, Secondary Hyperparathyroidism, and Increased Bone Resorption.

Consistent with the premise that dietary calcium is insufficient to meet the demand of the mineralization of the massive endosteal bone formation, the serum total calcium level of mice transplanted with Sca-1+ cells expressing the modified FGF-2 was significantly lower than that in mice transplanted with Sca-1+ cells expressing the GFP control gene at the time of the sacrifice at 12 week post-transplantation (9.82±0.31 mg/dl vs. 10.66±0.21 mg/dl, mean±SEM, n=8, p=0.035). Although the serum ionized calcium level was not measured in these mice, this suggests that the massive endosteal bone formation in the FGF-2 group led to hypocalcemia.

A well known consequence of hypocalcemia is secondary hyperparathyroidism. Accordingly, the serum levels of the mice were measured at the time of sacrifice (12 weeks post-transplantation) and the serum PTH levels were stratified into 4 groups according to the serum FGF-2 level: 1) ≤35 pg/ml (control, basal level), 2) 36-199 pg/ml, 3) 200-1,000 pg/ml, and 4) >1,000 pg/ml. FIG. 19 shows that there was a highly significant (p<0.001, one-way ANOVA), dose-dependent increase in serum PTH level with respect to serum FGF-2 level in the recipient mice. Except for the 36-199 pg/ml group, the increase in serum PTH in each subgroup was significantly (p<0.001) different from the control group. These findings confirm that the robust increase in endosteal bone formation in the FGF-2 mice led to secondary hyperparathyroidism.

A response to secondary hyperparathyroidism is an increased bone resorption. As an initial test for this possibility, the number of TRAP-positive multinucleated osteoclasts was measured on demineralized paraffin-embedded femoral sections. Immunohistochemical staining for tartrate-resistant acid phosphatase (TRAP) was evaluated in sections of femurs from 3 representative mice transplanted with pY-BMPFGFC2SC3N-transduced Sca-1+ cells that exhibited different levels of serum FGF-2. Recipient mice with high serum levels of FGF-2 had more TRAP-positive osteoclasts on bone surfaces than mice with intermediate serum FGF-2 levels, which had more TRAP-positive osteoclasts on bone surfaces than those with normal serum FGF-2 levels.

Increased trabecular bone formation at endosteal bone sites is essential for an effective treatment of osteoporosis and related musculoskeletal diseases. An increase in the amount of trabecular bone at the endosteal surfaces increases bone strength and reduces the risk of fractures. The results described above show that Sca-1+ hematopoietic stem and progenitor cells have propensity to home to and engraft in the bone marrow cavity (Spangrude et al., Blood 85:1006-1016, 1995), increasing the efficacy of bone marrow transplantation for osteogenic therapies.

Thus, Sca-1+ hematopoietic stem cells and progenitor cells can be used as the vehicle for osteogenic factors, for example, osteogenic growth factors, such as FGF-2 to promote endosteal bone formation. Suitable osteogenic growth factors are those, like FGF-2 that not only stimulates bone formation but also promotes hematopoietic stem cell renewal. FGF-2 promotes stem cell renewal without significantly inducing their differentiation (Kashiwakura et al., *Brit. J. Haematol.* 122:479-488, 2003; Kashiwakura et al., *Leuk. Lymphoma* 46:329-333, 2005). It has recently been reported that FGF-2 enhances undifferentiated proliferation of stem cells (He et al., *Nat. Genet.* 36(10):1117-1121, 2004). Moreover, FGF-2 is a known potent angiogenic agent. Vascularization of endosteal bone is essential to support endosteal bone formation. The lack of angiogenic effect of such factors as BMP2/4 may also partly contribute to the lack of enhanced endosteal bone formation by BMP-2/4 in this system. Therefore, FGF-2 and bioactive analogs of FGF-2 are suitable bone growth factor transgenes to promote endosteal and/or trabecular bone formation.

Intravenous injection of a Sca-1+ enriched cell population transduced with MLV-based vector expressing a modified FGF-2 gene in sublethally irradiated myelosuppressed $W^{41}/W^{41}$ recipient mice led to long-term engraftment of FGF-2-expressing cells in the bone marrow cavity. The engrafted cells retained their ability to express large amounts of FGF-2 protein as the average serum FGF-2 level of recipient mice was >20-fold higher than that of control mice. These findings not only confirm the previous suggestion that the viral transduction process did not significantly impede the engraftment of Sca-1+ cell (Deola et al., Hum. Gene Ther. 15:305-311, 2004; Hall et al., to be submitted, 2005), but more importantly, shows for the first time that intravenous transplantation of Sca-1+ cells expressing the modified FGF-2 gene led to a marked increase in bone ALP activity and a large increase in total and trabecular vBMD in recipient mice, which indicate a large enhancement in bone formation. The observations of the pQCT and bone histomorphometric evaluations of femurs of recipient mice indicating that the enhanced bone formation occurred primarily at trabecular bones on the endosteum are consistent with the previous finding that FGF-2 stimulated primarily trabecular bone formation on the endosteum without increasing periosteal and/or cortical bone formation (Mayahara et al., Growth Factors 9:73-80, 1993).

The results described above demonstrate certain additional benefits of using Sca-1+ hematopoietic progenitor cells as the target cell population and FGF-2 to promote endosteal bone formation. For example, two recent studies have provided strong evidence for the trans-differentiation of hematopoietic progenitor cells into cells of osteoblast lineage (Olmsted-Davis et al., *Proc. Natl. Acad. Sci. USA* 100:15877-15882, 2003; Dominici et al., *Proc. Natl. Acad. Sci. USA* 101:11761-11766, 2004). In the present study, a different experimental approach from the previous studies was utilized, e.g., using Sca-1+ cells isolated from the TgN-eGFP transgenic mice to follow the fate of donor cells in recipient mice. In this system, GFP-expressing osteoblasts (derived from the GFP-expressing donor Sca-1+ cells) were observed at the endosteal bone surface of recipient mice. This demonstrates that some of the donor Sca-1+ cells have trans-differentiated into osteoblasts. Thus, the use of Sca-1+ hematopoietic stem and/or progenitor cells as target cells has an advantage over other target cells in that the trans-differentiation enhances the commitment of transduced cells into cells of osteoblastic lineage, which is involved in enhanced endosteal/trabecular bone formation.

In addition, FGF-2 treatment promoted hematopoietic cell expansion and stem cell renewal, and also stimulated the formation of an adherent stromal cell layer in human bone marrow cultures (Kashiwakura et al., *Brit. J. Haematol.* 122: 479-488, 2003; Kashiwakura et al., *Leuk. Lymphoma* 46:329-333, 2005). Accordingly, the expression of FGF-2 transgene in these cells further enhances the renewal of FGF-2 expressing hematopoietic stem cells and the proliferation and commitment of engrafted FGF-2-expressing hematopoietic cells into cells of osteoblast linkage, which further enhances bone formation.

Intravenous injection of the Sca-1+ enriched cell population transduced with the MLV-modified FGF-2 vector in sublethally irradiated $W^{41}/W^{41}$ mice not only promoted endosteal/trabecular bone formation, but in fact led to a massive de novo endosteal/trabecular bone formation within the marrow cavity. Bone histomorphometric analysis of the femurs of recipient mice reveals that the enhanced endosteal bone formation in those several recipient mice that had a very high serum FGF-2 level (e.g., >4,000 pg/ml) was so robust that the entire marrow cavity was completely filled up with newly formed bony tissues. Consequently, these findings indicate that this transplantation approach and the use of the modified FGF-2 gene provided a very powerful means to increase de novo endosteal bone formation and promote division and differentiation of endosteal/trabecular bone cells. For example, with respect to treating osteoporotic patients, who are mostly elderly patients, it is useful to increase bone formation in a relatively short period of time to increase bone strength in order to avoid further fractures. Accordingly, the strategy disclosed herein overcomes the major deficiency in the field of osteoporosis treatment, that is, the ability to produce a sufficient amount of bone in a realistic timeframe. Consequently, strategy described herein is an ideal form of therapy for the treatment of osteoporosis and other conditions that require rapid bone growth.

The distribution and the location of the increased endosteal/trabecular bone formation is an important issue. Ideally, in order to realize maximal effects on the bone strength, the bone formation should be increased at sites where the increased bone formation is needed the most, that is, at bone sites where the strains and stresses imposed by normal physical activities are the greatest and at the site of fractures. Mechanical loading is perhaps the most important physiological feedback regulator of bone remodeling and the skeletal architectural integrity, as there is a strong relationship between the orientation of trabecular architecture and the assumed principal stress directions resulting from normal loading boundary conditions. Accordingly, it has been well known that mechanical loading increases bone formation primarily at sites where there are high physical strains and stresses in response to normal physical activities and to a much less extent at sites where there are less physical strains and stresses imposed by normal physical activities. Thus, it is mechanical loading is likely to enhance the amount of endosteal/trabecular bone formed at a given skeletal site in response to osteogenic agents (e.g., of FGF-2 or other bone growth promoting growth factors). Accordingly, the strategy described herein can be employed in combination with exercise, physical therapy and/or vibrational treatment modalities (e.g., ultrasound) that simulate mechanical loading without exercise to increase endosteal/trabecular bone formation at appropriate skeletal sites, leading to the maximally increase in bone strength. Moreover, the combination of administering Sca-1+ cells that express an osteogenic growth factor and appropriate mechanical or vibrational loading regimen increases endosteal cortical bone formation and cortical thickness, which, along with the increased endosteal trabecular bone formation, further increases bone strength.

To eliminate or reduce side effects of massive and rapid endosteal bone formation, such as a reduction in medullary hematopoiesis due to the loss of marrow cavity, and increased extramedullary hematopoiesis within the spleen and liver resulting in enlargement of these two organs, the treatment dose of serum FGF-2 should be maintained at a level of less than about 500 pg/ml (e.g., at less than about 200 pg/ml).

To reduce the risk of hypocalcemia, osteomalcia, and secondary hyperparathyroidism in response to the large increase in bone formation, and eliminate secondary hyperparathyroidism, FGF-2 dosage can be controlled and sufficient calcium and vitamin D supplementations can be administered to subjects undergoing this osteogenic regimen.

Since all of the adverse effects can be avoided by limiting the extent of the increase in bone formation and/or controlling the dose of growth factor. One way to control the dose is to regulate the expression of the modified FGF-2 transgene in the engrafted, transduced Sca-1$^+$ cells. In this regard, the expression of the modified FGF-2 transgene in these MLV vectors was driven by the powerful constitutive CMV viral promoter. A regulatable promoter can therefore be used to drive transgene expression to control the amounts of FGF-2 protein produced and secreted by engrafted, transduced cells.

Figure 7A:
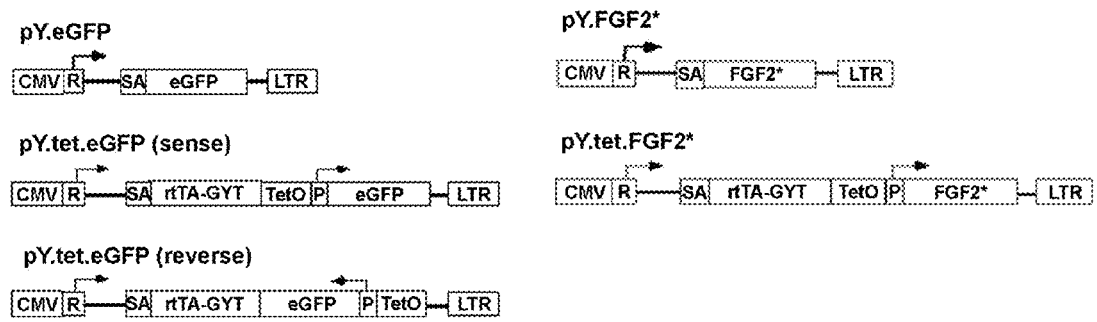
FIGS. 7A and B are schematic illustrations and a line graph, respectively, which illustrate inducibility of expression by the tet-on promoter.
Figure 7B:
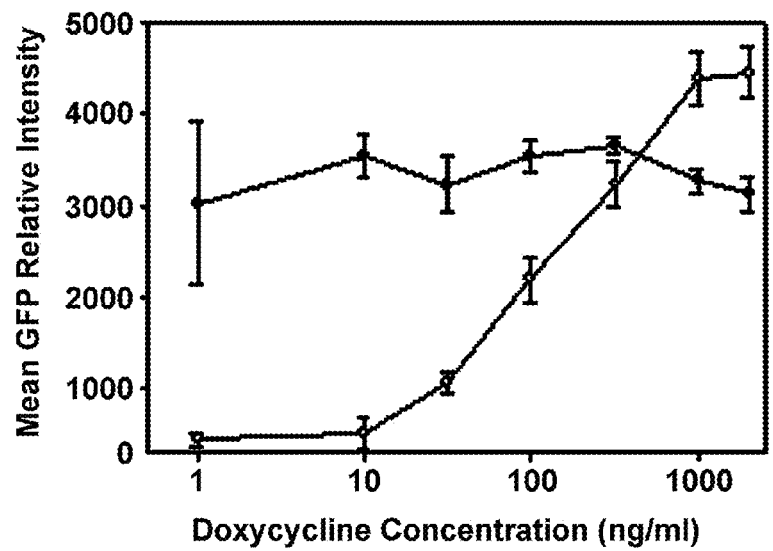
FIG. 7B illustrates the effects of doxycycline treatment on the production of GFP protein in cells transduced with the pY.eGFP vector (closed symbols) and the pY.tet.eGFP (open symbols). Ten µl of MLV.tet.eGFP viral stock was used to transduce $2\times10^5$ HT1080 cells in 6-well plates. An indicated amount of doxycycline (ranging from 0 to 1000 ng/ml) was added to each well. Forty-eight hours after transduction, the cells were detached and the percentage of GFP-expressing cells and the intensity of GFP expression were determined by flow cytometry. The fold induction was calculated by comparing the value of mean intensity multiple by the percentage of the positive cells. The value from the control medium (without doxycycline) was set at 1.0-fold.

For example, a tet-on regulatable promoter can be used to obtain consistent levels of FGF-2 that do not result in significant side effects. Briefly, two sets of MLV-based vectors have been constructed with a tet-regulatable promoter [pY.tet.eGFP (in forward and reverse orientation) and pY.tet-.FGF2*) expressing eGFP and the modified FGF-2 gene, respectively (FIG. 7A). Murine Sca-1$^+$, rat skin fibroblasts, and rat marrow stromal cells were transduced with pY.eGFP, pY.FGF2*, pY.tet.eGFP, as well as pY.tet.FGF2*, and the production of GFP protein (by FACS) and secretion of FGF-2 protein (by ELISA) in each CM were measured with or without doxycycline. With the GFP production as the transgene production by the transduced cells, doxycycline produced a dose-dependent production with the maximal production seen with 1 μg/ml doxycline (FIG. 7B), which was as high as or more than cells transduced with the MLV vector without the tet promoter. The transduced cells produced only basal amounts (<2 ng/ml) of FGF-2 per 24 hrs without doxycycline as compared to 48 ng/ml without doxycycline without the tet promoter. With the addition of 1 μg·ml doxycycline, the secretion of FGF-2 protein into the CMs by the transduced cells were increased by more than 30-fold to above levels observed with the non-regulatable promoter (68 ng/ml vs. 40 ng/ml). This tet-on promoter was just as effective in Sca-1$^+$ cells as in rat skin fibroblasts or in rat marrow stromal cells. Moreover, the tet-on promoter was effective in the sense or the reverse orientation (Table 13). Consequently, this tetracycline-inducible promoter system can be used to regulate FGF-2 expression in Sca-1$^+$ cells.

Thus, precisely controlling the secretion of FGF-2 by using a regulatable promoter system, such as the tet-on system, is useful to eliminate or reduce these undesirable side effects. Additionally, the use of a regulatable promoter system to drive expression of the modified FGF-2 gene also allows stopping the treatment when an increase in endosteal bone formation is no longer needed.

With the exception of the avoidable side effects that appeared to be associated with the robust bone formation and the high dose used, the osteogenic therapy described herein did not produce other significant harmful side effects. The treatment did not significantly affect growth, nor was it harmful to various vital organs.

The safety issue concerning insertion mutagenesis can be avoided by using plasmid vectors. Two major problems have prevented the generalized use of plasmid vectors to deliver therapeutic agents: 1) low transfection efficiency, and 2) random insertion. However, recent improved transfection reagents have significantly improved the transfection efficiency of plasmid vectors. For example, the use of nucleofection reagent yielded up to 90% transfection efficiency of plasmid vector in mesenchymal stem cells (Lorenz et al., *Biotechnol. Lett.* 26:1589-1592, 2004). To address the issue of random insertion, a single plasmid "Sleeping Beauty" transposon-based plasmid vector system has been developed, which yields stable integration of plasmid vector primarily at TA-dinucleotide sites (Harris et al., *Anal. Biochem.* 310:15-26, 2002). A nuclear localization sequence (NLS) has been included in the "Sleeping Beauty" vector to promote its nuclear transport. This plasmid system can include a constitutive or regulatable promoter (e.g., the tet-on promoter) depending on levels achieved following transfection.

Although the Sca-1$^+$ enriched cell population can favorably be used as the target donor cell population in this system, this cell population is very heterogenous and contains a number of different cell types in addition to hematopoietic stem cells. Additional improvements can be obtained by using hematopoietic stem cells. Stem cells are pluripotent cells, which have the ability of self-renewal, engraft, expand, and differentiate into any cells, including cell of osteoblast lineage. Consequently, the use of hematopoietic stem cells, instead of heterogeneous Sca-1$^+$ enriched cell population, is likely to increase the engraftment efficiency as well as the osteogenic potentials. There is evidence that transplantation of a single hematopoietic stem cell into a lethally irradiated animal is sufficient to repopulate the entire hematopoietic cell lineages. Consequently, a substantial reduction in the number of cells used in the transplantation can be achieved by using hematopoietic stem cells. In addition, stem cells are primitive cells that are not immunogenic, greatly reducing the incidence of immunorejection, graft-versus-host disease, and other adverse immune responses.

This discovery has great clinical significance and is extremely relevant to treatment of osteoporosis and related musculoskeletal diseases in that a large portion of patients with osteoporosis is elderly. Frequently, osteoporosis is not diagnosed until the disease has progressed to a relatively advanced stage, and bone mass has been significantly reduced and, in some cases, multiple fractures have already occurred. These patients require a therapy that can rapidly put back relatively large amounts of trabecular bones on their spines and hips within a relatively short time to avoid additional fractures. Accordingly, this osteogenic strategy is ideal for such subjects. More importantly, this treatment strategy, is not only applicable to elderly osteoporotic patients, but is also applicable to all patients with osteoporosis and related musculoskeletal diseases regardless of age or gender. Moreover, emerging studies suggest that hematopoietic (Schuldiner et al., *Proc. Natl. Acad. Sci. USA* 97:11307-11312, 2000) and mesenchymal (Spangrude et al., *Science* 241:58-62, 1988) stem cells home to sites of tissue injury. Accordingly, this approach is useful for a broad range of applications including wound healing, e.g., fracture repair.

Example 4

Sca-1$^+$ Hematopoietic Progenitor Cell-Based Systemic Gene Therapy in Old Adult Animals is as Effective as that in Young Adult Animals Materials and Methods Transplantation Bone Marrow Sca-1$^+$ Cells Bone marrow Sca-1$^+$ cells were isolated from TgN-GFP mice and transduced with MLV-based vectors as described in Example 3. The transduced cells were used in the transplantation experiment within 12-24 hrs after transduction. Two weeks before and 2 weeks after the irradiation procedure, One year-old (old adult) and 2-months-old (young adult) $W^{41}/W^{41}$ recipient mice were fed sterile food and autoclaved, acidified water (pH 2.0-2.5) containing antibodies (50 mg/L neomycin sulfate and 13 mg/L polymixin B sulfate) two weeks before and two weeks after the total body irradiation of a sublethal dose of 500 cGy at a rate of 80 cGy per minute as described in Example 3. Half of the mice from the old adult and the young adult groups received transplantation of 400,000 TgN-GFP Sca-1+ cells transduced with the pY-βgal marker gene vector, and the other half from each group received transplantation of 400,000 TgN-GFP Sca-1+ cells transduced with the MLV.FGF2* vector as described in Example 3. Mice were bled at 6, 8, 12, 14 weeks for analysis of engraftment (FACS) and serum collected for biochemical marker assays and stored at −70° C. At 14 weeks post-transplantation, mice were euthanized and femurs and tibia were collected for marrow, pQCT and bone histology analyses.

Other methods are described in details in Example 3. Non-parametric statistics were used to determine statistical significance of parameters because serum FGF-2 levels in the recipient mice did not follow Gausian distribution.

Results

Old Adult Mice Showed Similar Engraftment Efficiency as Young Adult Mice

To evaluate whether older adult mice have reduced engraftment efficiency for Sca-1+ cells, the engraftment efficiency of the transplanted GFP expressing donor Sca-1+ cells in the older adult mice (1 year-old) was determined and compared to that of the younger adult mice (2-month-old) by measuring GFP expression in the peripheral blood and in bone marrow cells in each recipient mice with FACS. Table 14 shows the chimeric levels in the peripheral blood of the 4 test groups. The engraftment levels in both the old and young adult group were relatively high (between 70-90%) at each time point. Regardless of the type of transduced donor cells, the engraftment levels of the old adult group were similar to those of the young adult group. ANOVA analysis indicates that there was no significant difference in chimeric levels among the 4 test groups.

just as efficient as that in the young adult mice, and confirm the findings shown in Example 3 that the expression of the modified FGF-2 did not modify the engraftment efficiency in either the old or the young adult animals.

Comparison of FGF2 Transgene Expression Between Old Adult Mice and Young Adult Mice.

Figure 8A:
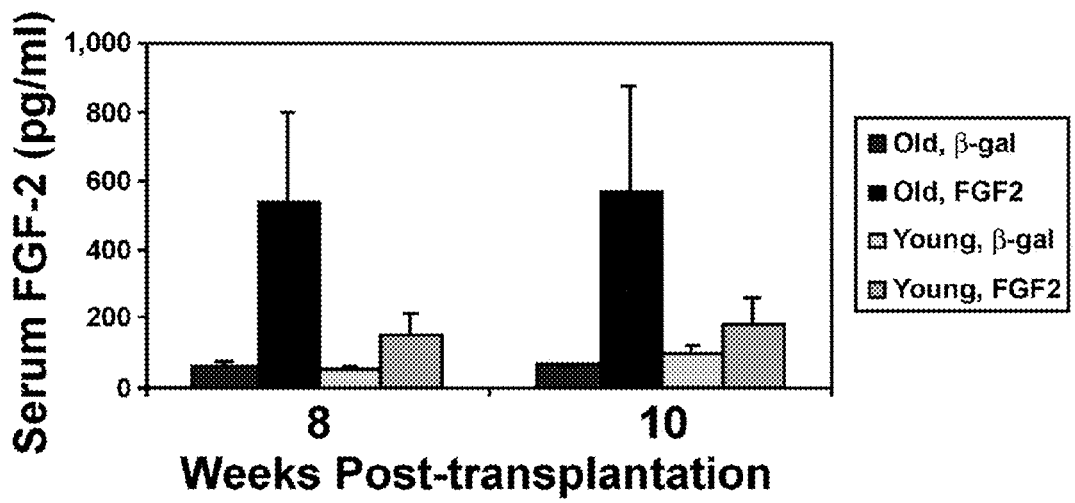
FIGS. 8A and B are bar graphs comparing FGF-2 levels and percent bone area in young and old mice transplanted with Sca-1+ cells transduced with MLV.β-gal or MLV.FGF2* vectors. Results are shown as mean±SD with n=9 or 10 per group.

In order for this systemic Sca-1+ cell based FGF-2 gene therapy to be effective in old adult mice, the old adult recipient mice should be at least just as effective in expressing the FGF-2 transgene as in young adult recipient. Accordingly, the serum FGF-2 level in the old adult mice after engraftment (at 8- and 10-weeks after transplantation) was measured with a commercial FGF-2 ELISA kit as an indicator of the ability of the old adult mice to express the FGF2 transgene. FIG. 8A reveals that, at each of the test time points (8- or 10-weeks post-transplantation), the old adult recipient mice receiving Sca-1+ cells transduced with the MLV. FGF2* vector showed a significantly higher serum FGF2 levels than those young adult recipient mice receiving these FGF-2 expressing cells. The serum FGF-2 level in old adult mice transplanted with Sca-1+ cells transduced with the MLV.β-gal control vector was also not significantly different from that in young adult mice transplanted with the untransduced control cells. Because there was no significant difference in the engraftment, the larger increase in serum FGF-2 in the old FGF-2 group compared to that in the young FGF-2 group was due to the enhanced ability of the engrafted cells to express the FGF2 protein in the old adult mice compared to young adult mice. As reported in Example 3, the variation in serum FGF-2 levels in mice transplanted with the FGF-2 expressing Sca-1+ cells was relatively large in the young adult mice. Thus, the relatively large variation in serum FGF-2 levels was unrelated to the age of the recipient mice.

To confirm that serum FGF-2 levels in these recipient mice are acceptable indices for FGF-2 transgene expression level, the modified FGF-2 mRNA levels in the bone marrow of each recipient mouse were also measure by real-time PCR. The bone marrow FGF-2 mRNA levels correlated linearly and strongly with serum FGF-2 levels at each time point (r=0.86,

TABLE 14

Comparison of the engraftment efficiency in the 1-year-old and the 2-months-old adult recipient mice (mean ± S.D.)

| Group | Treatment | n | 6 weeks | 8 weeks | 10 weeks | 12 weeks | 14 weeks |
|---|---|---|---|---|---|---|---|
| Old | β-gal | 9 | 77.66 ± 7.05 | 80.98 ± 7.23 | 82.45 ± 6.56 | 86.89 ± 5.17 | 82.77 ± 8.63 |
| Young | β-gal | 10 | 75.86 ± 4.19 | 78.65 ± 3.75 | 83.75 ± 3.61 | 89.88 ± 3.42 | 83.19 ± 6.10 |
| Old | FGF2* | 10 | 71.25 ± 14.38 | 76.93 ± 7.22 | 77.56 ± 14.00 | 87.07 ± 5.92 | 84.42 ± 7.67 |
| Old | FGF2* | 9 | 76.11 ± 5.50 | 83.12 ± 5.61 | 83.63 ± 5.29 | 87.04 ± 6.08 | 83.67 ± 5.10 |
| ANOVA | | | N.S. | N.S. | N.S. | N.S. | N.S. |

As previously reported, the levels of chimera in the bone marrow cells of each recipient mouse were significantly lower than those in the peripheral blood. At the time of euthanasia, the level of the chimera in the old adult group transplanted with the MLV.β-gal- and the MLV.FGF2*-transduced Sca-1+ donor cells was 20.47±5.19% and 23.66±7.55%, respectively. The level of the chimera in the young adult group transplanted with the two vectors was 22.35±5.14% and 21.18%±6.30%, respectively. There was no significant difference in the chimera levels in the bone marrow among the four test groups. Thus, these findings are consistent with the general belief that the engraftment of donor cells in the peripheral blood is a good indicator of the true bone marrow engraftment. These findings together indicate that the engraftment of the donor Sca-1+ cells in the old adult mice is p<0.0.0001, at 8 weeks post-transplantation; and r=0.69, p<0.0.0001, at 10-weeks time point). Thus, serum FGF-2 levels are suitable indices for the FGF-2 transgene expression in these recipient mice. Importantly, these data indicate that the older mice did not have a reduced capacity to express the FGF-2 transgene.

Transplantation of Modified FGF-2 Expressing Sca-1+ Cells Effectively Induced Endosteal Bone Formation in Recipient Mice Serum and bone alkaline phosphatase activity (ALP) and pQCT parameters in the recipient mice were measured at the time of euthanasia (14 weeks) as indices for bone formation response assessments. Similar to the serum FGF-2 levels, the variations in serum and bone ALP activities (normalized against protein or dried bone weight) in recipient mice transplanted with FGF-2 expressing Sca-1+ cells were also large. As a result, none of the differences in serum and bone ALP activity in this experiment reached the statistically significant level by the parametric statistical tests. However, non-parametric statistical analysis indicates that there was a significant (p<0.03) increase in tibial ALP/protein in FGF-2 expressing mice compared with β-gal expressing mice (for both old and young adults).

The total cortical and trabecular BMD as well as periosteal and endosteal bone parameters were measured in these mice by pQCT. With respect to trabecular bone mineral density (BMD), as expected, older mice have significantly lower trabecular BMD than younger mice. With the non-parametric Krusal-Wallis test, the FGF-2 mice showed a significantly increase in trabecular BMD at their corresponding age group (p=0.0052), indicating that the FGF2 treatment effectively increased trabecular BMD in both young and old mice. Correlation analyses indicate that there was a significant and positive correlation (r=0.34, p<0.05) between serum FGF-2 and trabecular bone mineral density (BMD) of these mice. These findings support the contention that transgenic expression of FGF-2 in the bone marrow space by the Sca-1+ cell-based systematic gene therapy can effectively induce endosteal bone formation in old as well as young adult mice.

To confirm an endosteal bone formation response in the old adult mice, bone histomorphometric analysis was performed on the femurs of old and young recipient mice transplanted with either β-gal expressing or FGF-2 expressing Sca-1+ cells. Briefly, recipient femurs were cut in half. The distal bone half was demineralized and embedded in paraffin while the proximal half was embedded in methylmethacrylate. Longitudinal sections were prepared from the paraffin-embedded bones were stained with H & E for tissue structure or Mallory's trichrome stain for collagen, respectively. Longitudinal sections were prepared from the methylmethacrylate embedded bones and the sections were stained with Goldner's stain for mineralization. To demonstrate the dose-dependent effect, histology results of a representative mouse expressing moderate and a representative mouse expressing high levels of FGF-2 as well as a mouse receiving β-gal were included.

Transplantation of FGF-2 expressing Sca-1+ cells resulted in massive bone formation in young as well as old adult mice as indicated by the Mallory's staining. Furthermore, the massive increase in bone formation was seen at diaphyses, metaphyses, as well as epiphyses of the femur, consistent with the premise that the treatment caused systemic bone formation along the endosteal bone surfaces. There is evidence that the enhanced endosteal/trabecular bone formation in the older mice was also dose-dependent, since the increase in bone formation was much higher in mice with high serum FGF-2 levels compared to those with moderate of low serum FGF2.

Figure 8B:
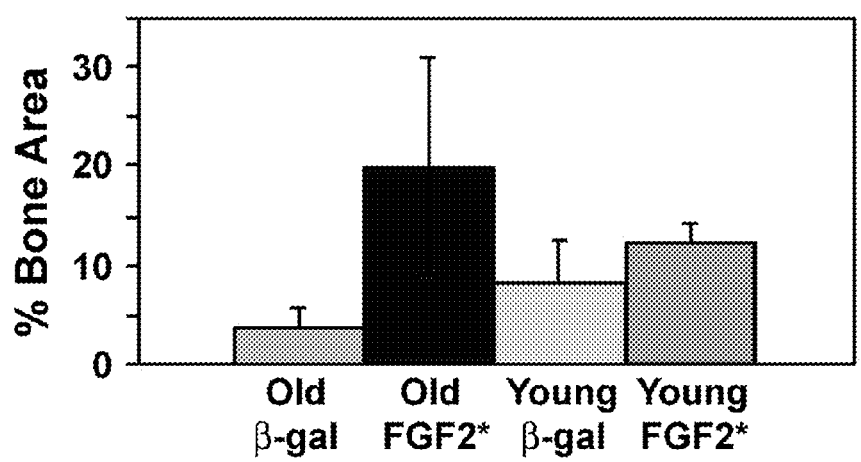

The total bone area of the bone sections were also determined, and is shown in FIG. 8B. The FGF2* treatment significantly increased the bone area in both the young and the old animals, confirming the osteogenic effect of this Sca-1+ cell-based systemic gene therapy. Consistent with the higher serum FGF2 levels in the older mice, the bone area in the FGF2*-treated older animals was also much bigger than that of the FGF2*-treated younger mice. These bone histological evidence clearly demonstrated that this Sca-1+ cell-based systematic therapy is just as effective (if not more so) in the old adult mice as that in the young adult mice.

As shown in Example 3, the rapid and massive increase in bone formation in recipient mice that showed high levels of serum FGF2 can cause calcium deficiency, osteomalacia, and secondary hyperparathyroidism. This is a concern especially with respect to the older animals, since it has been well established that calcium absorption is not as efficient in the elderly as that in young adults. To determine if the older mice treated with FGF2 expressing Sca-1+ cells did not develop a more severe calcium deficiency problem than the young mice receiving the FGF2-expressing Sca-1+ donor cells, the serum albumin-adjusted calcium levels of the young and old recipient mice were determined (as a surrogate measure of ionized calcium levels) and compared (Table 15). Two-way ANOVA indicates that the FGF-2 treatment significantly (p<0.0001) increased total as well as albumin-adjusted serum calcium levels in both young and old recipient mice. Tukey's HSD a priori testing shows that young β-gal group was significantly (p<0.05) higher than the old mice transplanted with β-gal expressing donor cells. Both the young and old FGF2 group had a significantly (p<0.01 for each) higher total and adjust calcium levels than their corresponding β-gal group. These findings confirm that the high expression levels of FGF-2 did not produce a bigger problem in causing calcium deficiency in the older animals than that in the young adult mice.

TABLE 15

Comparison of the albumin-adjusted serum calcium levels in the old recipient mice transplanted with Sca-1+ cells expressing β-gal or the modified FGF-2. total calcium and albumin was measured at endpoint (14 weeks). Corrected calcium was calculated using the following formula: Corrected calcium = total calcium + 0.8 (4.5 − albumin). (mean ± SD, n = 9 or 10 per group).

| Age group | Treatment | Serum albumin | Total Calcium | Adjusted Calcium |
|---|---|---|---|---|
| Old | β-gal | 4.0 ± 0.1 | 10.4 ± 0.3 | 10.8 ± 0.3 |
| Old | FGF2* | 3.9 ± 0.3 | 11.2 ± 0.3 | 11.7 ± 0.3 |
| Young | β-gal | 4.0 ± 0.1 | 10.9 ± 0.5 | 11.3 ± 0.6 |
| Young | FGF2* | 3.9 ± 0.2 | 11.4 ± 0.4 | 11.9 ± 0.4 |
| ANOVA, p value | | 0.24 | <0.0001 | <0.0001 |

To assess if osteomalacia occurred, bone sections of the old recipient mice expressing low (49 pg/ml), moderate (840.4 pg/ml) or high (2,933 pg/ml) serum FGF-2 at the metaphyses and epiphyses sites were also stained with the Goldner's stain to distinguish mineralized and unmineralized bone marrix. Similar to the results observed in young animals as discussed in Example 3, the old FGF2*-treated mouse expressing very high levels of FGF2 exhibited a relatively large amount of newly formed, unmineralized bone matrix overlaying the mineralized trabeculae. Bone formation was so massive and so rapid that it is possible that insufficient amounts of calcium were present to mineralize the newly formed bone in those mice with very high serum FGF2 levels. However, compared to the results shown in Example 3, the amounts of newly formed, un-mineralized bone matrix in the old adult mice that expressed high serum levels of FGF-2 did not appear to be more than those in the young adult mice with similar serum FGF-2 levels, demonstrating that suboptimal calcium levels were not any more severe in the older animals than in the younger mice.

In summary, the findings shown in this Example has clearly indicated that this Sca-1+ cell-based systemic gene therapy is as effective, if not more so, in the older mice. Consequently, these findings support the contention that this therapy is well suited for the elderly osteoporotic patients, who require a therapy that can put back relatively large amounts of trabecular bones at endosteal bone surfaces within their spines and hips within a relatively short time to avoid further fractures.

Example 5

Unmodified FGF-2 can be Used to Promote Endosteal Trabecular Bone Formation

The modified FGF2 transgene, rather than unmodified FGF2 gene, was used in the other Examples was based on the facts that 1) FGF2 lacks a classical secretion signal sequence and its extracellular secretion is mediated by an energy-dependent non-ER/golgi pathway (Mignatti et al., J Cell Physiol 151:81-93, 1992; Florkiewicz et al., J Cell Physiol 162:388-399, 1995; Dahl et al., Biochemistry 39:14877-14883, 2000), which is highly inefficient, leading to very poor secretion rate of FGF2 in mammalian cells (Moscatelli et al., J Cell Physiol 129:273-276, 1986); and 2) FGF2 protein can form various disulfide forms, which can result in significant loss of biological activities and protein stability (Iwane et al., Biochem Biophys Res Commun 146:470-477, 1987). However, the efficiency of Sca-1$^+$ cells to secrete the unmodified FGF2 has not been evaluated. This Example evaluated whether the engrafted Sca-1$^+$ cells secrete sufficient amounts of an unmodified FGF2 transgene by this systemic gene transfer protocol. For comparison, Sca-1$^+$ cells transduced with a MLV vector expressing a modified FGF2 with only the added BMP2/4 pro-peptide but without the cysteine mutations (MLV.proFGF2) was also included for testing.

Materials and Methods

Six-months-old $W^{41}/W^{41}$ recipients were divided into 4 groups and were transplanted with 500,000 Sca-1+ cells from GFP transgenic mice transduced to express β-gal, unmodified WT FGF2 transgene, modified FGF2 with only the BMP2/4 propeptide gene or the FGF2* mutant gene as described in Example 3. Blood samples were obtained for analysis of engraftment (by FACS analyses of GFP expression) and for measurements of serum FGF2 levels at 6, 8, 10, and 14 weeks post-transplantation. Serum biochemical markers and calcium were also measured.

Results

Assessment of engraftment was performed by measuring the relative percentage of GFP expressing cells in the peripheral blood (by FACS) of each recipient mouse. Table 16 shows that there was no significant difference in the engraftment level among each of the four test group.

TABLE 16

Relative engraftment levels in mice transplanted with Sca-1$^+$ cells expressing wild type (WT-FGF2), modified FGF2 with only the BMP2/4 propeptide (Pro. FGF2), and the modified FGF2 (FGF2*) at 6 weeks, 8 weeks, or 10 weeks post-transplantation (mean ± SD).

| Group | N | 6 weeks | 8 weeks | 10 weeks |
|---|---|---|---|---|
| β-gal | 5 | 79.89 ± 5.21 | 87.12 ± 1.95 | 84.91 ± 2.55 |
| WT-FGF2 | 10 | 80.34 ± 6.63 | 87.25 ± 3.02 | 82.95 ± 3.97 |
| Pro. FGF2 | 10 | 80.65 ± 6.47 | 88.83 ± 2.38 | 83.76 ± 4.73 |
| FGF2* | 10 | 78.49 ± 6.70 | 85.78 ± 4.87 | 79.97 ± 6.32 |
| ANOVA | | N.S. | N.S. | N.S. |

To confirm engraftment, the RNA levels of the FGF2 transgene in the bone marrow cells of each of the recipient mice were measured by real-time PCR with a set of specific primers at the end-point of the experiment (10 weeks post-transplantation). The results were shown as relative fold changes in relationship to the housekeeping gene, cyclophilin, by the ΔCT method. Table 17 confirms engraftment.

TABLE 17

Relative FGF2 mRNA in bone marrow cells of recipient mice (relative fold changes with respect to cyclophilin housekeeping gene).

| Group | N | Relative levels of FGF-2 mRNA/Cyclophilin mRNA |
|---|---|---|
| β-gal | 7 | 0.00 ± 0.00 |
| WT-FGF2 | 10 | 0.0056 ± 0.0165 |
| Pro-FGF2 | 9 | 0.0070 ± 0.0104 |
| FGF2* | 9 | 0.0070 ± 0.0104 |

Figure 9:
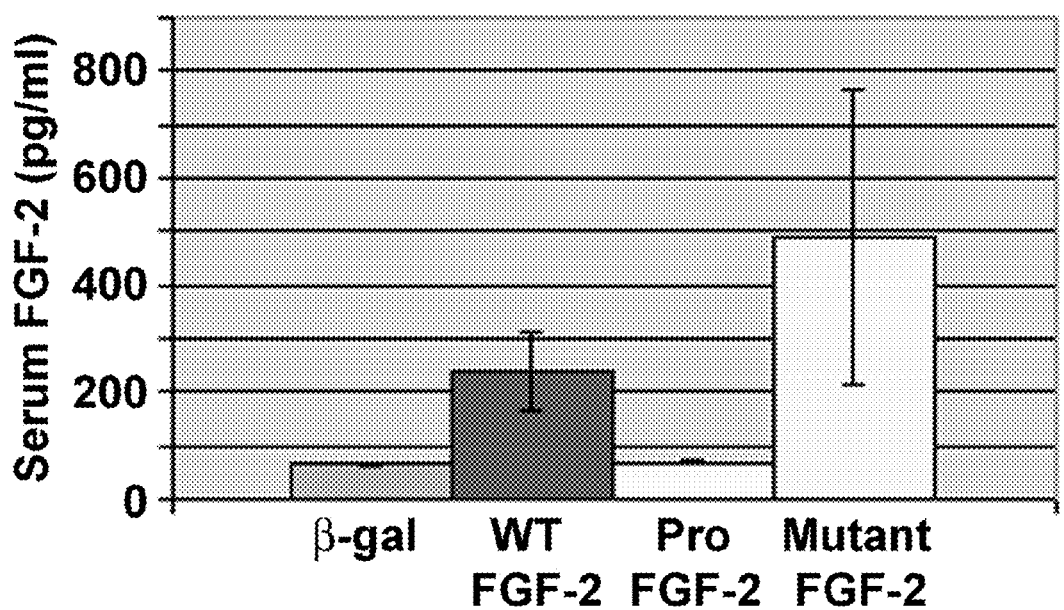
FIG. 9 is a bar graph illustrating serum FGF-2 levels in recipient mice transduced with Sca-1+ cells expressing the β-gal control gene, the wild type unmodified FGF-2 gene (WT FGF2), the modified FGF-2 gene with only the addition of the BMP2/4 propeptide (Pro FGF-2), and the modified FGF-2 gene with substitutions for C2 and C3 (Mutant FGF-2) and the BMP2/4 propeptide. Results are shown as mean±SD.

To measure the FGF2 transgene expression, serum FGF2 levels were assayed at 6 weeks post-transplantation using a FGF2 commercial ELISA kit. Surprisingly, the serum FGF2 levels in the unmodified FGF2 group were increased nearly 4-fold over the β-gal controls (FIG. 9), suggesting that Sca-1$^+$ cells transduced with the unmodified FGF2 secrete substantial amounts of FGF2 protein. Nevertheless, the secretion levels were still significantly lower (>2-fold) than that of mice in the modified FGF2 group (487±869 pg/mL, p<0.001). The wide variation in measurement was observed in both the modified and unmodified FGF2 groups, suggesting it is not a result of the gene modification. Moreover, linear regression analysis revealed that the serum FGF-2 levels in these recipient mice correlated significantly with the FGF-2 transgene mRNA levels in their bone marrow cells (r=0.44, p=0.0099), indicating that the engrafted cells indeed expressed the FGF2 transgene mRNA.

Serum total calcium, albumin-adjusted calcium, and serum bone formation biochemical markers were also measured in these recipient mice. Table 18 shows that in this Example, none of the groups showed evidence for calcium deficiency. ANOVA analysis revealed that the serum ALP levels in these recipient mice were not significantly different, presumably due to large variation. Conversely, recipient mice of the FGF2* group showed significant increases in serum CTX and osteocalcin. However, these biochemical markers in the WT FGF2 and the Pro.FGF2 groups were not significantly different from the β-gal control group.

TABLE 19

Serum calcium levels and bone formation biochemical markers levels of recipient mice. Results are shown as mean ± SD.

| Group | N | Total Ca | Albumin | Albumin-adjusted Calcium | Serum ALP | Serum CTX | Serum Osteocalcin |
|---|---|---|---|---|---|---|---|
| β-gal | 5 | 10.24 ± 0.33 | 3.88 ± 0.16 | 10.74 ± 0.22 | 95.00 ± 9.90 | 2.14 ± 1.67 | 40.36 ± 7.23 |
| WT-FGF2 | 10 | 10.34 ± 0.23 | 4.02 ± 0.19 | 10.72 ± 0.18 | 94.60 ± 14.07 | 1.61 ± 0.95 | 33.16 ± 8.37 |
| Pro. FGF2 | 9 | 10.04 ± 0.16 | 3.89 ± 0.21 | 10.53 ± 0.19 | 91.89 ± 11.58 | 3.02 ± 1.78 | 51.60 ± 16.29 |

TABLE 19-continued

Serum calcium levels and bone formation biochemical markers levels of recipient mice. Results are shown as mean ± SD.

| Group | N | Total Ca | Albumin | Albumin-adjusted Calcium | Serum ALP | Serum CTX | Serum Osteocalcin |
|---|---|---|---|---|---|---|---|
| FGF2* | 10 | 10.21 ± 0.39 | 3.96 ± 0.20 | 10.64 ± 0.35 | 97.10 ± 18.74 | 3.66 ± 1.75 | 54.26 ± 13.22 |
| ANOVA | | N.S. | N.S. | N.S. | N.S. | 0.035 | 0.002 |

Corrected calcium was calculated using the following formula: Corrected calcium = total calcium + 0.8 (4.5 − albumin)

Bone histomorphometric analyses indicate that only mice from the FGF2* group show large increase in endosteal/trabecular bone formation, while mice of the WT FGF2 group did not show consistent histomorphometric evidence of an increased endosteal bone formation (data not shown). Quantitation of bone areas confirm that recipient mice of the FGF2* expressing cells, but not those of WT FGF2 expressing mice showed an increase in percent bone area (6.97±4.71% for the β-gal group; 6.78±3.75% for the WT-FGF2 group, and 16.02±7.51% for the FGF2* group). Linear regression indicates that the percent bone area correlated significantly with serum FGF2 levels ($r=0.79$, $p<0.0007$), a finding is consistent with the interpretation that the increase bone mass in these recipient mice was due to FGF2 expression.

In summary, transplantation of Sca-1$^+$ cells in the recipient mice led to an increase in serum FGF2 levels. However, inspite of the higher expression of FGF2 in the wild type FGF2 gene group compared to controls, there was no evidence for a consistent increase in endosteal trabecular bone formation. There are at least two possible explanations: 1) the amounts of FGF2 produced by the Sca-1$^+$ cells transduced with the MLV.WT-FGF2 vector is not be sufficient to consistently produce an osteogenic effect, and/or 2) the modified FGF2 gene possesses more potent osteogenic functions than the WT FGF2.

Example 6

Transplantation of Human CD34$^+$/Lin$^-$ Hematopoietic Stem/Progenitor Cells that Express a Modified FGF-2 Transgene Promotes Endosteal/Trabecular Bone Formation This example illustrates that human hematopoietic stem/progenitor cells are suitable cell vehicle source and that this hematopoietic stem/progenitor cell-based systemic gene therapy protocol is suitable for humans. In this Example, the effectiveness of human hematopoietic stem/progenitor cells as a cell vehicle is assessed in athymic "nude" mice in order to avoid an immune response against the transplanted human cells. CD34 is a cell surface glycoprotein (also known as mucosialin) that is expressed on human hematopoietic stem cells, but not on mature blood cells. CD34 is a well recognized cell surface marker of human hematopoietic stem cells and progenitor cells. Human CD34$^+$ (e.g., CD34$^+$, lin$^-$, AC133$^+$, CD45$^-$, CXCR4$^+$) cells are hematopoietic stem/progenitor cells used as the ex vivo cell vehicle to express the modified FGF-2 transgene (FGF-2*) to induce endosteal trabecular bone.

Materials and Methods

Animals

Recipient mice for transplation of human cells to produce a working model of human hematopoietic stem cell transplantation are athymic "nude" mice. These mice lack a functional thymus and are an ideal animal model for studying allografts and xenografts. These mice are maintained in a complete sterile environment.

Transplantation Strategy

The transplantation strategy is very similar to that described in Example 3, with the exception that transduced human CD34$^+$ cells are used as the donor cells. Highly purified human CD34$^+$ cells (available from commercial sources, such as Cambrex Bio Science Walkersville, Inc) can be expanded in culture by maintaining the stem cells in serum-free medium containing stem cell factor, thrombopoietin, IGF-2, FGF-2, and angiopoietin 2. Transduction of the pY.eGFP (for assessment of engraftment), pY.FGF2*, and pY.tet.FGF2* vector is performed as described above. After appropriate conditioning, each nude mouse receives 300,000 transduced CD34$^+$ cells as described in Example 3. Recipient mice that receive pY.tet.FGF2* transduced cells are treated with an effective dose of doxycycline in their drinking water to initiate transgene expression. Blood is drawn at various time points. Engraftment is assessed by detecting GFP production in peripheral cells of the transduced mouse. Bone formation effects are analyzed by BMD measurements using pQCT, serum biochemical bone formation markers, and histological evaluations of bone formation as described in Example 3.

Results

Transplantation of human CD34$^+$ cells in athymic nude mice is predicted to increase endosteal trabecular bone formation. The increase in trabecular bone formation is proportional to the serum FGF-2 levels in these mice. The induced trabecular bones are of normal quality and microstructure. The increase in endosteal bone formation leads to an increase in overall bone strength. The serum FGF-2 levels and thereby the amounts of new bone formation in nude mice receiving the pY.tet.FGF2* transduced cells is regulatable by adjusting the doxycycline dose in the drinking water.

Example 7

Transplantation of Hematopoietic Stem/Progenitor Cells that Express Wnt1 Promotes Endosteal/Trabecular Bone Formation Bone growth factor genes that have the ability to expand the stem cell population and to stimulate bone formation are able to promote endosteal trabecular bone formation when delivered using transduced hematopoietic stem and/or progenitor cells.

Materials and Methods

Construction of pY.Wnt1a Vector

The full length Wnt1 cDNA was cloned from the mouse Wnt1 gene (obtained from the ATCC). The resulting PCR product was subcloned into the MLV-based pY vector backbone to generate the pY-Wnt1 vector. Several pY.Wnt1 clones were randomly selected and sequenced to confirm the identity pY.Wnt1 vector.

Animals

As described in Example 3, $W^{41}/W^{41}$ mice are used as the recipient mice, and Sca-1+ cells of the GFP expressing transgenic mice are used as donor cells to demonstrate efficacy of osteogenic growth factors other than FGF-2 in the induction of bone formation.

Transplantation Strategy

Sca-1+ cells are transduced with either the pY.Wnt1 vector or the pY.β-gal control vector. For comparison, the same Sca-1+ cells are also transduced with the pY.FGF2* vector. The transplantation procedure is identical to that described in Example 3. Blood is drawn at various time points. Engraftment is assessed by GFP production in peripheral cells of the transduced mouse. Bone formation effects can be analyzed by BMD measurements using pQCT, serum biochemical bone formation markers, and histological evaluations of bone formation as described in Example 3.

Results

The MLV-based vectors expressing the murine Wnt1a was generated and HT1080 cells were transduced with the vector. The relative levels of Wnt1 protein in the CMs and cell lysates, 72 hours after the transduction, were identified by Western immunoblots. HT1080 cells transduced with pY.β-gal showed undetectable levels of Wnt1 protein in CMs or in cell lysates. In contrast, there were high levels of immunoreactive Wnt1 proteins in both the CM and cell lysate of the pY.Wnt1 transduced cells, indicating that the pY.Wnt1 vector was capable of inducing Wnt1 protein synthesis.

To confirm that growth factors other than FGF-2 that satisfy the criteria of 1) promoting self-renewal of hematopoietic stem cells, and 2) inducing bone formation induce the formation of bone in vivo, the pY.Wnt1 vector, along with the pY.β-gal and pY.FGF2* vectors, are transduced into Sca-1+ cells as described in Example 3. Blood is drawn at various time points. Engraftment is assessed by the GFP production in peripheral cells of the transduced mouse. Bone formation effects can be analyzed by BMD measurements using pQCT, serum biochemical bone formation markers, and histological evaluations of bone formation as described in Example 3.

Results

Transplantation of pY.Wnt1 transduced Sca-1+ cells is predicted to produce massive new trabecular bone formation at endosteal bone sites. The bone formation is proportional to the serum levels of Wnt1.

Example 8

Transplantation of Hematopoietic Stem Cells and/or Progenitor Cells that Express FGF-2 Promotes Bone Formation is Broadly Applicable The effectiveness of hematopoietic stem/progenitor cell transplantation to induce bone formation in different animals can be confirmed using a larger, non-rodent animal, such as the beagle dog. Effective delivery of osteogenic growth factors using hematopoietic stem/progenitor cells to induce bone formation is not limited to small rodents, but also applies to higher mammals, such as cats, dogs, domesticated livestock (such as sheep, goats, pigs and cows), horses and captured wild-animals, as well as non-human primates and humans. In this experimental example, dogs are selected as the recipient because the bone metabolism of dogs closely resembles that of humans.

Materials and Methods

Animals

Eight month old normal beagle dogs weighing 12 kg are used as the transplantation recipient. To avoid the need for immunosuppressive therapy, autologous marrow transplantation is used.

Transplantation Strategy

Before the experiment, the dogs receive baseline measurements of bone (including a bone density test and blood and urine tests for bone metabolism) and hematology assessment. To prevent the calcium deficiency related to massive new bone formation, the dogs receive 200 mg of calcium supplementation along with 500 international units of vitamin D prior to and during the period of evaluation. In some cases, erythropoietin therapy is administered before the transplantation procedure to enhance bone formation in sites throughout the skeleton, including fatty marrow sites.

The recipient dogs receive five daily injections of GCSF (canine, from Amgen) at a dose of 10 mg per kilogram to enhance the number of bone marrow progenitor cells in the harvested marrow; this treatment also results in more rapid engraftment. The hematopoietic stem/progenitor cells are harvested by apheresis from the dog's blood. The leukocyte fraction is frozen until approximately 24 hours before transplantation. The harvested leukocytes are enriched for CD34+, lin− progenitor cells. Briefly, the leukocytes are labeled with biotinylated monoclonal antibody 1H6 (immunoglobulin G1 anti-canine CD 34) 40 μg per milliliter at 4° C. for 30 minutes. The cells are incubated with streptavidin-conjugated microbeads for 30 minutes and 4° C.; and then separated by using an immuno magnetic column technique (Miltenyi Biotech, Auburn Calif.). Depending upon the number of stem cells harvested by leukopheresis, the hematopoietic stem/precursor cells can be expanded by culturing the stem cells in serum-free medium containing stem cell factor, thrombopoietin, IGF-2, FGF-2, and angiopoietin 2. Transduction can be accomplished with the MLV.tet.FGF2* vector, which contains a tet-on regulatable promoter that allows regulation of the gene therapy.

Prior to transplantation, the recipient dogs are conditioned with nonmyeloablative total body irradiation of 200 to 300 cGy at 7 cGy/Min or Fludabarine (500 mg per meter squared) at five separate doses without the radiation. Four to 24 hours after the conditioning, the dogs receive the engineered hematopoietic bone marrow stem/precursor cells for transplantation by IV infusion of $4.0 \times 10^8$ cells per kilogram. Tetracycline (or an analog thereof) is administered orally to initiate the transgene expression. Transgene expression is maintained as long as the dogs are given the tetracycline. Once the tetracycline is stopped, expression of the introduced osteogenic growth factor is silenced. In this way, the dose of the gene therapy can be regulated.

The standard follow-up for marrow transplantation is provided, including monitoring of the peripheral white blood count. In addition, the recipients are monitored for calcium deficiency. Evidence of calcium deficiency includes low serum calcium and a serum PTH above the upper normal limit. This can be preceded by very large increases in serum alkaline phosphatase and osteocalcin. When evidence of calcium deficiency is detected, the tetracycline administration can be discontinued in order to silence expression of the growth factor gene for the period sufficient to correct the calcium deficiency, after which the gene therapy can be reinitiated. Optionally, calcium intake can be increased by 100 mg increments.

To enhance the effects of the osteogenic therapy, the dogs are trained for an exercise program. Such exercises are important to influence the amount and orientation of the new bone being deposited. During therapy as the bone density increases the dogs can be trained to increase the intensity of the exercise program.

Therapeutic efficacy is monitored primarily by bone density monitoring, which can be measured periodically during therapy. Blood samples can also be obtained for measurements of biochemical markers of bone turnover. To confirm the extent and quality of bone formation, a bone biopsy can be obtained and bone histology can be performed.

Results

Transplantation of hematopoietic stem cells that express osteogenic growth factors is predicted to result in increased bone formation in animals other than rodents, including humans. The newly formed bone is normal in microstructure and can be produced without inducing calcium deficiency or osteomalacia. Typically, bone formation is concentrated to the endosteal bone surfaces. The serum biochemical markers of bone formation (serum alkaline phosphatase and osteocalcin) increase substantially as compared to control subjects. Overall, it is predicted that bone density in treated subjects is predicted to increase by 25% or more compared to control subjects.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of identifying an agent that modulates bone growth, maintenance and repair, the method comprising:
harvesting at least one hematopoietic stem cell;
transducing and expressing in the at least one mouse hematopoietic stem cell at least one heterologous nucleic acid comprising a polynucleotide sequence that encodes an osteogenic growth factor comprising a secretable analog of human fibroblast growth factor-2 (FGF-2) encoded by a nucleic acid sequence comprising in a 5' to 3' direction: a polynucleotide sequence that encodes a bone morphogenetic protein 2/4 (BMP2/4) hybrid secretion signal peptide sequence and a polynucleotide sequence that encodes a mature human FGF-2 polypeptide comprising a mutation that results in the substitution of an alanine for a cysteine in amino acid position 70 of FGF-2 and a mutation that results in the substitution of an asparagine for a cysteine in amino acid position 88 of FGF-2;
introducing the at least one hematopoietic stem cell or a progeny thereof into an immunologically compatible mouse, wherein expression of the secretable analog of human FGF-2 produces an increase in serum level of FGF-2 as compared to immunologically compatible mice engrafted with hematopoietic stem cells transduced with the BMP2/4 hybrid secretion signal peptide sequence and a wild type FGF-2-control;
administering an agent to the mouse; and
screening for modulation of FGF-2 secretion, wherein an increase in FGF-2 secretion identifies an agent that increases bone growth.

2. The method of claim 1, wherein the hematopoietic stem cell is a pluripotent hematopoietic stem cell.

3. The method of claim 2, wherein the hematopoietic stem cell expresses CXCR4.

4. The method of claim 2, wherein the hematopoietic stem cell is a Sca-1$^+$ cell.

5. The method of claim 1, wherein the at least one heterologous nucleic acid comprising the polynucleotide sequence that encodes an osteogenic growth factor is introduced into the hematopoietic stem cell by electroporation, biolistic transformation, lipid mediated transformation, or transfection of the cell with a viral vector comprising the heterologous nucleic acid.

6. The method of claim 5, wherein the viral vector is an adenovirus vector, an adeno-associated virus vector, a murine leukemia virus vector or a lentivirus vector.

7. The method of claim 6, wherein the viral vector is a replication defective viral vector.

8. The method of claim 1, wherein the polynucleotide sequence that encodes an osteogenic growth factor is operably linked to a transcription control sequence comprising a regulatable promoter.

9. The method of claim 8, wherein the transcription control sequence comprises a tetracycline regulatable promoter.

* * * * *

```
                            SEQUENCE LISTING

<160> NUMBER OF SEQ ID NOS: 23

<210> SEQ ID NO 1
<211> LENGTH: 468
<212> TYPE: DNA
<213> ORGANISM: homo sapiens

<400> SEQUENCE: 1
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagaggga gttgtgtcta tcaaaggagt gtgtgctaac      240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468

<210> SEQ ID NO 2
<211> LENGTH: 155
<212> TYPE: PRT
<213> ORGANISM: homo sapiens

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125
```

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

<210> SEQ ID NO 3
<211> LENGTH: 1314
<212> TYPE: DNA
<213> ORGANISM: artificial sequence
<220> FEATURE:
<223> OTHER INFORMATION: recombinant FGF-2 analog

<400> SEQUENCE: 3

| | | | | | | |
|---|---|---|---|---|---|---|
| atggtggccg | ggacccgctg | tcttctagcg | ttgctgcttc | cccaggtcct | cctgggcggc | 60 |
| gcggctggcc | tcgttccgga | gctgggccgc | aggaagttcg | cggcggcgtc | gtcgggccgc | 120 |
| ccctcatccc | agccctctga | cgaggtcctg | agcgagttcg | agttgcggct | gctcagcatg | 180 |
| ttcggcctga | acagagacc | cacccccagc | agggacgccg | tggtgccccc | ctacatgcta | 240 |
| gacctgtatc | gcaggcactc | aggtcagccg | ggctcacccg | ccccagacca | ccggttggag | 300 |
| agggcagcca | gccgagccaa | cactgtgcgc | agcttccacc | atgaagaatc | tttggaagaa | 360 |
| ctaccagaaa | cgagtgggaa | acaacccgg | agattcttct | taatttaag | ttctatcccc | 420 |
| acggaggagt | ttatcacctc | agcagagctt | caggttttcc | gagaacagat | gcaagatgct | 480 |
| ttaggaaaca | atagcagttt | ccatcaccga | attaatattt | tgaaatcat | aaaacctgca | 540 |
| acagccaact | cgaaattccc | cgtgaccaga | cttttggaca | ccaggttggt | gaatcagaat | 600 |
| gcaagcaggt | gggaaagttt | tgatgtcacc | ccgctgtga | tgcggtggac | tgcacaggga | 660 |
| cacgccaacc | atggattcgt | ggtggaagtg | gcccacttgg | aggagaaaca | aggtgtctcc | 720 |
| aagagacatg | ttaggataag | caggtctttg | caccaagatg | aacacagctg | gtcacagata | 780 |
| aggccattgc | tagtaacttt | tggccatgat | ggccggggcc | atgccttgac | ccgacgccgg | 840 |
| agggccaagc | gtgcagccgg | gagcatcacc | acgctgcccg | ccttgcccga | ggatggcggc | 900 |
| agcggcgcct | tcccgcccgg | ccacttcaag | gaccccaagc | ggctgtactg | caaaaacggg | 960 |
| ggcttcttcc | tgcgcatcca | ccccgacggc | cgagttgacg | gggtccggga | gaagagcgac | 1020 |
| cctcacatca | agctacaact | tcaagcagaa | gagagaggag | ttgtgtctat | caaggagtg | 1080 |
| tctgctaacc | gttacctggc | tatgaaggaa | gatggaagat | tactggcttc | taaaaatgtt | 1140 |
| acggatgagt | gttctttttt | tgaacgattg | gaatctaata | actacaatac | ttaccggtca | 1200 |
| aggaaataca | ccagttggta | tgtggcactg | aaacgaactg | ggcagtataa | acttggatcc | 1260 |
| aaaacaggac | ctgggcagaa | agctatactt | tttcttccaa | tgtctgctaa | gagc | 1314 |

<210> SEQ ID NO 4
<211> LENGTH: 438
<212> TYPE: PRT
<213> ORGANISM: artificial sequence
<220> FEATURE:
<223> OTHER INFORMATION: recombinant FGF-2 analog

<400> SEQUENCE: 4

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
 50                  55                  60

Gln Arg Pro Thr Pro Ser Arg Asp Ala Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
            100                 105                 110

His His Glu Glu Ser Leu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Arg
            260                 265                 270

Gly His Ala Leu Thr Arg Arg Arg Ala Lys Arg Ala Ala Gly Ser
        275                 280                 285

Ile Thr Thr Leu Pro Ala Leu Pro Glu Asp Gly Ser Gly Ala Phe
        290                 295                 300

Pro Pro Gly His Phe Lys Asp Pro Lys Arg Leu Tyr Cys Lys Asn Gly
305                 310                 315                 320

Gly Phe Phe Leu Arg Ile His Pro Asp Gly Arg Val Asp Gly Val Arg
                325                 330                 335

Glu Lys Ser Asp Pro His Ile Lys Leu Gln Leu Gln Ala Glu Glu Arg
            340                 345                 350

Gly Val Val Ser Ile Lys Gly Val Ser Ala Asn Arg Tyr Leu Ala Met
        355                 360                 365

Lys Glu Asp Gly Arg Leu Leu Ala Ser Lys Asn Val Thr Asp Glu Cys
370                 375                 380

Phe Phe Phe Glu Arg Leu Glu Ser Asn Asn Tyr Asn Thr Tyr Arg Ser
385                 390                 395                 400

Arg Lys Tyr Thr Ser Trp Tyr Val Ala Leu Lys Arg Thr Gly Gln Tyr
                405                 410                 415

Lys Leu Gly Ser Lys Thr Gly Pro Gly Gln Lys Ala Ile Leu Phe Leu
            420                 425                 430

Pro Met Ser Ala Lys Ser
        435

<210> SEQ ID NO 5
<211> LENGTH: 852
<212> TYPE: DNA

<213> ORGANISM: artificial sequence
<220> FEATURE:
<223> OTHER INFORMATION: recombinant signal sequence

<400> SEQUENCE: 5

```
atggtggccg ggacccgctg tcttctagcg ttgctgcttc cccaggtcct cctgggcggc    60
gcggctggcc tcgttccgga gctgggccgc aggaagttcg cggcggcgtc gtcgggccgc   120
ccctcatccc agccctctga cgaggtcctg agcgagttcg agttgcggct gctcagcatg   180
ttcggcctga acagagacc caccccagc agggacgccg tggtgccccc ctacatgcta   240
gacctgtatc gcaggcactc aggtcagccg ggctcacccg ccccagacca ccggttggag   300
agggcagcca gccgagccaa cactgtgcgc agcttccacc atgaagaatc tttggaagaa   360
ctaccagaaa cgagtgggaa acaacccgg agattcttct ttaatttaag ttctatcccc   420
acggaggagt ttatcacctc agcagagctt caggttttcc gagaacagat gcaagatgct   480
ttaggaaaca atagcagttt ccatcaccga attaatattt atgaaatcat aaaacctgca   540
acagccaact cgaaattccc cgtgaccaga ctttttggaca ccaggttggt gaatcagaat   600
gcaagcaggt gggaaagttt tgatgtcacc cccgctgtga tgcggtggac tgcacaggga   660
cacgccaacc atggattcgt ggtggaagtg gcccacttgg aggagaaaca aggtgtctcc   720
aagagacatg ttaggataag caggtctttg caccaagatg aacacagctg gtcacagata   780
aggccattgc tagtaacttt tggccatgat ggccggggcc atgccttgac ccgacgccgg   840
agggccaagc gt                                                        852
```

<210> SEQ ID NO 6
<211> LENGTH: 284
<212> TYPE: PRT
<213> ORGANISM: artificial sequence
<220> FEATURE:
<223> OTHER INFORMATION: recombinant signal sequence

<400> SEQUENCE: 6

```
Met Val Ala Gly Thr Arg Cys Leu Leu Ala Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175
```

```
Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Arg
            260                 265                 270

Gly His Ala Leu Thr Arg Arg Arg Ala Lys Arg
        275                 280
```

<210> SEQ ID NO 7
<211> LENGTH: 32
<212> TYPE: DNA
<213> ORGANISM: artificial sequence
<220> FEATURE:
<223> OTHER INFORMATION: oligonucleotide primer

<400> SEQUENCE: 7
gcgcgcaagc ttgtggcagc cgggagcatc ac         32

<210> SEQ ID NO 8
<211> LENGTH: 29
<212> TYPE: DNA
<213> ORGANISM: artificial sequence
<220> FEATURE:
<223> OTHER INFORMATION: oligonucleotide primer

<400> SEQUENCE: 8
gcggctgacg gccattaaaa tcagctctt         29

<210> SEQ ID NO 9
<211> LENGTH: 53
<212> TYPE: DNA
<213> ORGANISM: artificial sequence
<220> FEATURE:
<223> OTHER INFORMATION: oligonucleotide primer

<400> SEQUENCE: 9
aaactgcagg ggatcccggc cgggccccgc aggatggcag ccgggagcat cac         53

<210> SEQ ID NO 10
<211> LENGTH: 29
<212> TYPE: DNA
<213> ORGANISM: artificial sequence
<220> FEATURE:
<223> OTHER INFORMATION: oligonucleotide primer

<400> SEQUENCE: 10
gcggctgacg gccattaaaa tcagctctt         29

<210> SEQ ID NO 11
<211> LENGTH: 33
<212> TYPE: DNA
<213> ORGANISM: artificial sequence
<220> FEATURE:
<223> OTHER INFORMATION: oligonucleotide primer

<400> SEQUENCE: 11
tctatcaaag gagtgtctgc taaccgttac ctg        33

<210> SEQ ID NO 12
<211> LENGTH: 33
<212> TYPE: DNA
<213> ORGANISM: artificial sequence
<220> FEATURE:
<223> OTHER INFORMATION: oligonucleotide primer

<400> SEQUENCE: 12
cgagtaacgg ttagcagaca ctcctttgat aga        33

<210> SEQ ID NO 13
<211> LENGTH: 33
<212> TYPE: DNA
<213> ORGANISM: artificial sequence
<220> FEATURE:
<223> OTHER INFORMATION: oligonucleotide primer

<400> SEQUENCE: 13
ttactggctt ctaaatctgt tacggatgag tgt        33

<210> SEQ ID NO 14
<211> LENGTH: 33
<212> TYPE: DNA
<213> ORGANISM: artificial sequence
<220> FEATURE:
<223> OTHER INFORMATION: oligonucleotide primer

<400> SEQUENCE: 14
acactcatcc gtaacagatt tagaagccag taa        33

<210> SEQ ID NO 15
<211> LENGTH: 33
<212> TYPE: DNA
<213> ORGANISM: artificial sequence
<220> FEATURE:
<223> OTHER INFORMATION: oligonucleotide primer

<400> SEQUENCE: 15
ttactggctt ctaaaaatgt tacggatgag tgt        33

<210> SEQ ID NO 16
<211> LENGTH: 33
<212> TYPE: DNA
<213> ORGANISM: artificial sequence
<220> FEATURE:
<223> OTHER INFORMATION: oligonucleotide primer

<400> SEQUENCE: 16
acactcatcc gtaacatttt tagaagccag taa        33

<210> SEQ ID NO 17
<211> LENGTH: 33
<212> TYPE: DNA
<213> ORGANISM: artificial sequence
<220> FEATURE:
<223> OTHER INFORMATION: oligonucleotide primer

<400> SEQUENCE: 17
tctatcaaag gagtggctgc taaccgttac ctg        33

<210> SEQ ID NO 18
<211> LENGTH: 33
<212> TYPE: DNA
<213> ORGANISM: artificial sequence

```
<220> FEATURE:
<223> OTHER INFORMATION: oligonucleotide primer

<400> SEQUENCE: 18
cgagtaacgg ttagccgaca ctcctttgat aga                                    33

<210> SEQ ID NO 19
<211> LENGTH: 33
<212> TYPE: DNA
<213> ORGANISM: artificial sequence
<220> FEATURE:
<223> OTHER INFORMATION: oligonucleotide primer

<400> SEQUENCE: 19
ttactggctt ctaaagctgt tacggatgag tgt                                    33

<210> SEQ ID NO 20
<211> LENGTH: 33
<212> TYPE: DNA
<213> ORGANISM: artificial sequence
<220> FEATURE:
<223> OTHER INFORMATION: oligonucleotide primer

<400> SEQUENCE: 20
acactcatcc gtaaccgatt tagaagccag taa                                    33

<210> SEQ ID NO 21
<211> LENGTH: 11
<212> TYPE: DNA
<213> ORGANISM: artificial sequence
<220> FEATURE:
<223> OTHER INFORMATION: artificial Kozak sequence

<400> SEQUENCE: 21
gcccaccatg g                                                            11

<210> SEQ ID NO 22
<211> LENGTH: 24
<212> TYPE: PRT
<213> ORGANISM: artificial sequence
<220> FEATURE:
<223> OTHER INFORMATION: recombinant BMP2/4 secretion signal sequence

<400> SEQUENCE: 22

Leu Val Thr Phe Gly His Asp Gly Arg Gly His Ala Leu Thr Arg Arg
1               5                   10                  15

Arg Arg Ala Lys Arg Ser Pro Lys
            20

<210> SEQ ID NO 23
<211> LENGTH: 34
<212> TYPE: PRT
<213> ORGANISM: artificial sequence
<220> FEATURE:
<223> OTHER INFORMATION: recombinant BMP2/4FGF secretion signal sequence

<400> SEQUENCE: 23

Leu Val Thr Phe Gly His Asp Gly Arg Gly His Ala Leu Thr Arg Arg
1               5                   10                  15

Arg Arg Ala Lys Arg Ala Ala Gly Ser Ile Thr Thr Leu Pro Ala Leu
            20                  25                  30

Pro Glu
```